(12) United States Patent
Senger et al.

(10) Patent No.: US 11,046,937 B2
(45) Date of Patent: *Jun. 29, 2021

(54) METHODS FOR CONVERSION OF THE SUBSTRATE SPECIFICITY OF DESATURASES

(71) Applicants: BASF PLANT SCIENCE COMPANY GMBH, Ludwigshafen (DE); Bioriginal Food & Science Corp., Saskatoon (CA)

(72) Inventors: Toralf Senger, Durham, NC (US); Patricia Vrinten, Saskatoon (CA); Ze Long Lim, Saskatoon (CA)

(73) Assignees: BASF PLANT SCIENCE COMPANY GMBH, Ludwigshafen (DE); Bioriginal Food & Science Corp., Saskatoon (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/414,150

(22) Filed: May 16, 2019

(65) Prior Publication Data
US 2019/0270972 A1 Sep. 5, 2019

Related U.S. Application Data

(62) Division of application No. 15/105,080, filed as application No. PCT/IB2014/067021 on Dec. 17, 2014, now Pat. No. 10,329,541.

(Continued)

(51) Int. Cl.
*C12N 9/02* (2006.01)
*C07K 14/46* (2006.01)
*C12P 7/64* (2006.01)

(52) U.S. Cl.
CPC .......... *C12N 9/0071* (2013.01); *C07K 14/461* (2013.01); *C12N 9/0083* (2013.01);
(Continued)

(58) Field of Classification Search
CPC .. C12N 9/0071; C12N 9/0083; C12Y 114/19; C12P 7/6427; C12P 7/6472; C07K 14/461
See application file for complete search history.

(56) References Cited

U.S. PATENT DOCUMENTS

| 7,087,432 B2 | 8/2006 | Qiu et al. |
| 7,554,008 B2 | 6/2009 | Napier et al. |

(Continued)

FOREIGN PATENT DOCUMENTS

| CN | 1922311 A | 2/2007 |
| WO | WO-02/26946 A2 | 4/2002 |

(Continued)

OTHER PUBLICATIONS

Zhang et al., Evolution-related Amino Acids Play Important Role in Determining Regioselectivity of Fatty Acid Desaturase From Pichia Pastoris, Mol. Biol. Rep., 36(3):567-73 (2009).

(Continued)

*Primary Examiner* — Richard G Hutson
(74) *Attorney, Agent, or Firm* — Marshall, Gerstein & Borun LLP

(57) ABSTRACT

The present invention relates to methods for the conversion of the substrate specificity of desaturases. Specifically, the present invention pertains to a method for the conversion of the substrate specificity of a Δ5 and/or Δ6 desaturase to the substrate specificity of a Δ4 desaturase, the method comprising: identifying regions and/or amino acid residues which control the substrate specificity of (i) the Δ5 and/or Δ6 desaturase and (ii) the Δ4 desaturase; and replacing in the (Continued)

Figure 2:
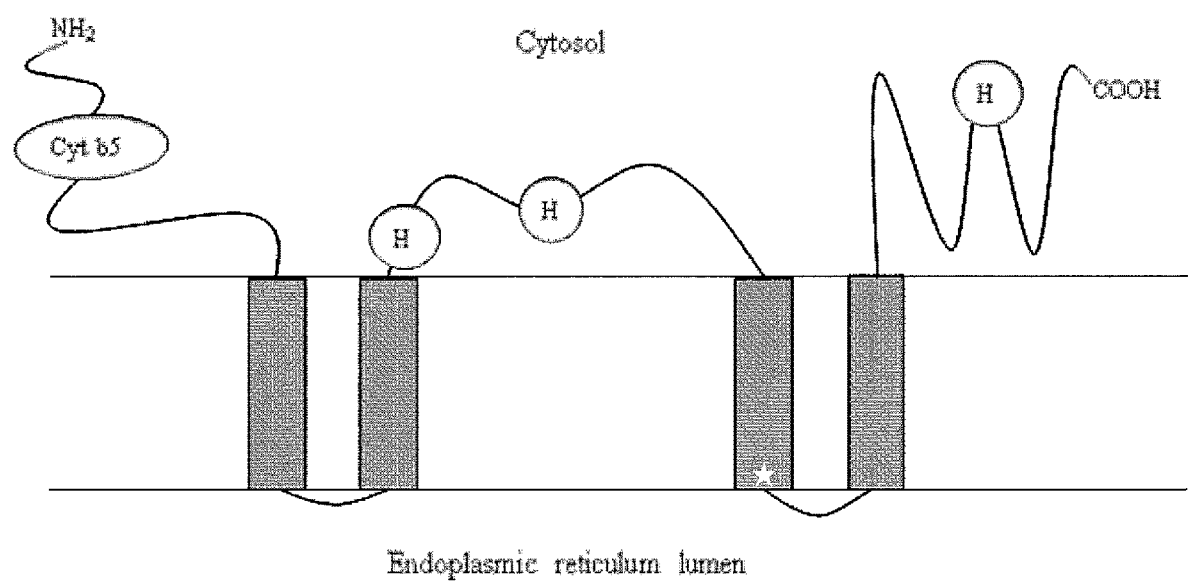

amino acid sequence of the mentioned Δ5 and/or Δ6 desaturase, the regions and/or amino acid residues which control the substrate specificity of the Δ5 and/or Δ6 desaturase, by the corresponding regions and/or amino acid residues which control the substrate specificity of the Δ4 desaturase, thereby converting the substrate specificity of the Δ5 and/or Δ6 desaturase to the substrate specificity of the Δ4 desaturase. The present invention further concerns a method for the conversion of the substrate specificity of a Δ4 desaturase to the substrate specificity of a Δ5 and/or Δ6 desaturase, the method comprising: identifying regions and/or amino acid residues which control the substrate specificity of (i) the Δ4 desaturase and (ii) the Δ5 and/or Δ6 desaturase; and replacing in the amino acid sequence of the indicated Δ4 desaturase, the regions and/or amino acid residues which control the substrate specificity of the Δ4 desaturase, by the corresponding regions and/or amino acid residues which control the substrate specificity of the Δ5 and/or Δ6 desaturase, thereby converting the substrate specificity of the Δ4 desaturase to the substrate specificity of the Δ5 and/or Δ6 desaturase. In addition, the invention encompasses desaturases with converted substrate specificity.

7 Claims, 12 Drawing Sheets

Specification includes a Sequence Listing.

Related U.S. Application Data

(60) Provisional application No. 61/916,825, filed on Dec. 17, 2013.

(52) U.S. Cl.
CPC ........... *C12P 7/6427* (2013.01); *C12P 7/6472* (2013.01); *C12Y 114/19* (2013.01)

(56) References Cited

U.S. PATENT DOCUMENTS

| | | |
|---|---|---|
| 7,629,503 B2 | 12/2009 | Cirpus et al. |
| 7,671,252 B2 | 3/2010 | Qiu et al. |
| 7,951,994 B2 | 5/2011 | Graham et al. |
| 7,977,469 B2 | 7/2011 | Qiu et al. |
| 8,088,906 B2 | 1/2012 | Qiu et al. |
| 8,329,993 B2 | 12/2012 | Napier et al. |
| 8,710,299 B2 | 4/2014 | Bauer et al. |
| 9,359,597 B2 | 6/2016 | Qiu et al. |
| 9,382,529 B2 | 7/2016 | Bauer et al. |
| 2012/0124705 A1 | 5/2012 | Bauer et al. |
| 2013/0291228 A1 | 10/2013 | Senger et al. |

FOREIGN PATENT DOCUMENTS

| | | |
|---|---|---|
| WO | WO-03/72784 A1 | 9/2003 |
| WO | WO-2004/090123 A2 | 10/2004 |
| WO | WO-2005/080578 A2 | 9/2005 |
| WO | WO-2005/083093 A2 | 9/2005 |
| WO | WO-2007/133425 A2 | 11/2007 |
| WO | WO-2008/040787 A2 | 4/2008 |
| WO | WO-2011/006948 A1 | 1/2011 |
| WO | WO-2012/052468 A2 | 4/2012 |

OTHER PUBLICATIONS

Ahmann et al., Identification of a Δ4-desaturase from the microalga Ostreococcus lucimarinus, Eur. J. Lipid Sci. Technol., 113:832-40 (2011).

Betts et al., Amino acid properties and consequences of substitutions, pp. 289-316 IN: Barnes et al. (eds.), Bioinformatics for Geneticists, John Wiley and Sons (2003).

Borngraber et al., Shape and specificity in mammalian 15-lipoxygenase active site. The functional interplay of sequence determinants for the reaction specificity, J. Biol. Chem., 274(52):37345-50 (1999).

Bowler et al., The Phaeodactylum genome reveals the evolutionary history of diatom genomes, Nature, 456(7219):239-44 (2008).

Broun et al., Catalytic plasticity of fatty acid modification enzymes underlying chemical diversity of plant lipids, Science, 282(5392):1315-7 (1998).

Cahoon et al., A determinant of substrate specificity predicted from the acyl-acyl carrier protein desaturase of developing cat's claw seed, Plant Physiol., 117(2):593-8 (1998).

Cahoon et al., Redesign of soluble fatty acid desaturases from plants for altered substrate specificity and double bond position, Proc. Natl. Acad. Sci. USA, 94(10):4872-7 (1997).

Crawford et al., The role of seminal plasma for improved outcomes during in vitro fertilization treatment: review of the literature and meta-analysis, Hum. Reprod. Update, 21(2):275-84 (2015).

Domergue et al., Cloning and functional characterization of Phaeodactylum tricornutum front-end desaturases involved in eicosapentaenoic acid biosynthesis, Eur. J. Biochem., 269(16):4105-13 (2002).

Extended European Search Report, European patent application No. 14872225.9, dated Apr. 12, 2017.

Gagne, Structure and function in plant Δ12 fatty acid desaturases and acetylenases, Masters Thesis University of Saskatchewan (2008).

Gerhardt, Fatty acid degradation in plants, Prog. Lipid Res., 31(4):417-46 (1992).

Guhnemann-Schafer et al., Fatty acid beta-oxidation in glyoxysomes. Characterization of a new tetrafunctional protein (MFP III), Biochim. Biophys. Acta, 1256(2):181-6 (1995).

Hastings et al., A vertebrate fatty acid desaturase with Delta 5 and Delta 6 activities, Proc. Natl. Acad. Sci. USA, 98(25):14304-9 (2001).

Hastings et al., Molecular cloning and functional characterization of fatty acyl desaturase and elongase cDNAs involved in the production of eicosapentaenoic and docosahexaenoic acids from alpha-linolenic acid in Atlantic salmon (*Salmo salar*), Mar. Biotechnol. (NY), 6(5):463-74 (2004).

International Preliminary Report, International Application No. PCT/IB2014/067021, dated Jun. 21, 2016.

Kinney, Genetic Engineering of Oilseeds for Desired Traits, pp. 149-66, IN: Setlow (ed.), Genetic Engineering, vol. 19, New York: Plenum Press (1997).

Kunau et al., beta-oxidation of fatty acids in mitochondria, peroxisomes, and bacteria: a century of continued progress, Prog. Lipid Res., 34(4):267-342 (1995).

Li et al., Vertebrate fatty acyl desaturase with ?4 activity, Proc. Natl. Acad. Sci. USA, 107(39):16840-5 (2010).

Libisch et al., Chimeras of Delta6-fatty acid and Delta8-sphingolipid desaturases, Biochem. Biophys. Res. Commun., 279(3):779-85 (2000).

Lim et al., Four amino acid residues influence the substrate chain-length and regioselectivity of Siganus canaliculatus Δ4 and Δ5/6 desaturases, Lipids, 49(4):357-67 (2014).

Meesapyodsuk et al., Primary structure, regioselectivity, and evolution of the membrane-bound fatty acid desaturases of Claviceps purpurea, J. Biol. Chem., 282(28):20191-9 (2007).

Meesapyodsuk et al., The front-end desaturase: structure, function, evolution and biotechnological use, Lipids, 47(3):227-37 (2012).

Meyer et al., Biosynthesis of docosahexaenoic acid in Euglena gracilis: biochemical and molecular evidence for the involvement of a Delta4-fatty acyl group desaturase, Biochemistry, 42(32):9779-88 (2003).

Murphy et al., Biosynthesis, targeting and processing of oleosin-like proteins, which are major pollen coat components in *Brassica napus*, 13(1):1-16 (1998).

Na-Ranong et al., Targeted mutagenesis of a fatty acid Delta6-desaturase from Mucor rouxii: role of amino acid residues adjacent to histidine-rich motif II, Biochem. Biophys. Res. Commun., 339(4):1029-34 (2006).

(56) References Cited

OTHER PUBLICATIONS

Napier et al., The production of very-long-chain PUFA biosynthesis in transgenic plants: towards a sustainable source of fish oils, Proc. Nutr. Soc., 64(3):387-93 (2005).

Napier et al., The role of cytochrome b5 fusion desaturases in the synthesis of polyunsaturated fatty acids, Prostaglandins Leukot. Essent. Fatty Acids, 68(2):135-43 (2003).

Ngo et al., Computational Complexity, Protein Structure Prediction, and the Levinthal Paradox, pp. 433 and 492-5, IN: Merz et al. (eds.), The Protein Folding Problem and Tertiary Structure Prediction, Birkhauser Boston (1994).

Ohlrogge et al., Lipid biosynthesis, The Plant Cell, 7:957-70 (1995).

Pereira et al., Recent advances in the study of fatty acid desaturases from animals and lower eukaryotes, Prostaglandins Leukot. Essent. Fatty Acids, 68(2):97-106 (2003).

Pollak et al., Isolation of a ?5 desaturase gene from Euglena gracilis and functional dissection of its HPGG and HDASH motifs, Lipids, 47(9):913-26 (2012).

Qiu et al., Identification of a Delta 4 fatty acid desaturase from *Thraustochytrium* sp. involved in the biosynthesis of docosahexanoic acid by heterologous expression in *Saccharomyces cerevisiae* and *Brassica juncea*, J. Biol. Chem., 276(34):31561-6 (2001).

Rapoport, Arachidonic acid and the brain, J. Nutr., 138(12):2515-20 (2008).

Sandberg et al., Engineering multiple properties of a protein by combinatorial mutagenesis, Proc. Natl. Acad. Sci. USA, 90(18):8367-71 (1993).

Sayanova et al., Mutagenesis and heterologous expression in yeast of a plant Delta6-fatty acid desaturase, J. Exp. Bot., 52(360):1581-5 (2001).

Shanklin et al., Desaturases: emerging models for understanding functional diversification of diiron-containing enzymes, J. Biol. Chem., 284(28):18559-63 (2009).

Shanklin et al., Desaturation and related modifications of fatty acids, Annu. Rev. Plant Physiol. Plant Mol., 49:611-41 (1998).

Shanklin et al., Eight histidine residues are catalytically essential in a membrane-associated iron enzyme, stearoyl-CoA desaturase, and are conserved in alkane hydroxylase and xylene monooxygenase, Biochemistry, 33(43):12787-94 (1994).

Sperling et al., Desaturases fused to their electron donor, Eur. J. Lipid Sci. Technol., 103:158-80 (2001).

Sprecher et al., Reevaluation of the pathways for the biosynthesis of polyunsaturated fatty acids, J. Lipid Res., 36(12):2471-7 (1995).

Sprecher, Metabolism of highly unsaturated n-3 and n-6 fatty acids, Biochim. Biophys. Acta, 1486(2-3):219-31 (2000).

Stymne, Biosynthesis of 'uncommon' fatty acids and their incorporation into triacylglycerols, pp. 150-158 IN: Murata et al., Biochemistry and Molecular Biology of Membrane and Storage Lipids of Plants (1993).

Thies et al., Association of n-3 polyunsaturated fatty acids with stability of atherosclerotic plaques: a randomised controlled trial, Lancet, 361(9356):477-85 (2003).

Tonon et al., Identification of a very long chain polyunsaturated fatty acid Delta4-desaturase from the microalga Pavlova lutheri, FEBS Lett., 553(3):440-4 (2003).

Tripodi et al., Functional characterization of front-end desaturases from trypanosomatids depicts the first polyunsaturated fatty acid biosynthetic pathway from a parasitic protozoan, FEBS J., 273(2):271-80 (2006).

Voelker, Plant acyl-ACP thioesterases: Chain-length determining enzymes in plant fatty acid biosynthesis, pp. 111-131, IN: Setlow (ed.): Genetic Engineering vol. 18, New York: Plenum Press (1996).

Yuan et al., Modification of the substrate specificity of an acyl-acyl carrier protein thioesterase by protein engineering, Proc. Natl. Acad. Sci. USA, 92(23):10639-43 (1995).

Zheng et al., Characterization and comparison of fatty acyl Delta6 desaturase cDNAs from freshwater and marine teleost fish species, Comp. Biochem. Physiol. B Biochem. Mol. Biol., 139(2):269-79 (2004).

Zheng et al., Highly unsaturated fatty acid synthesis in vertebrates: new insights with the cloning and characterization of a delta6 desaturase of Atlantic salmon, Lipids, 40(1):13-24 (2005).

Zhou et al., Isolation and characterization of genes from the marine microalga Pavlova salina encoding three front-end desaturases involved in docosahexaenoic acid biosynthesis, Phytochemistry, 68(6):785-96 (2007).

Fig. 1

```
Sc D4      (1)   MGGGGQLGESGENGCKSAAGVYTWEEVQHHSNRNDQWLVIDRKVYNVTQWAKRHPGGERV
Sc D5/6    (1)   MGGGGQPRESGE    GSSPAVYTWEEVQHHSSRNDQWLVIDRKVYNISQWAKRHPGGYRV

Sc D4     (61)   LNHYAGEDATEAFTAFHPDIKFVQKYMKPLLVGELAATEPSQDQDKNAALIQDFHTLRQQ
Sc D5/6   (59)   IGHYAGEDATEAFTAFHPDLKFVQKFLKPLLIGELAATEPSQDRNKNAALIQDFHTLRQQ

Sc D4    (121)   AESEGLFQARPLFFLLHLGHILLLEALALLMVWHWGTGWLQTLLCAVMLATAQSQAGWLQ
Sc D5/6  (119)   AESEGLFQARPLFFLLHLGHILLLEALALLMVWHWGTGWLQTLLCAVMLATAQSQAGWLQ

Sc D4    (181)   HDFGHLSVFKKSRWNHLVHKFVIGHLKGASANWWNHRHFQHHAKPNIFKKDPDINMVDLF
Sc D5/6  (179)   HDFGHLSVFKKSRWNHLVHHFVIGHLKGASANWWNHRHFQHHAKPNIFKKDPDINMVDLF

Sc D4    (241)   VLGETQPVEYGIKKIKNMPYNHQHKYFELVAPPLLIPVFYNYNIMMTMITRRDYVDLSWA
Sc D5/6  (239)   VLGETQPVEYGVKKIKLMPYNHQHQYFHLIGPPLLIPVFFHYQLLKIMISHRYWIDLVWC

Sc D4    (301)   MTFYIRYMLCYVPVYGLFGSIALMMFARFLESHWFVWVTQMSHLPMDIDNDKKRDWLSMQ
Sc D5/6  (299)   ISFYLRYMCCYVPVYGLFGSVVLIVFIRFLESHWFVWVTQMNHLPMDINYENENDWLSMQ

Sc D4    (361)   LQATCNIEKSFFNDWFSGHLNFQIEHHLFPRMPRHNYHLVAPQVQTLCEKHGIPYEVKTL
Sc D5/6  (359)   LQATCNVEQSLFNDWFSGHLNFQIEHHLFPTMPRHNYHLVVPBVRALCEKHEIPYQVKTL

Sc D4    (421)   WKGMVDVVRALKKSGDLWLDAYLHK
Sc D5/6  (419)   FQAFADIIRSLKNSGELWLDAYLHK
```

Sc D4 = SEQ ID NO: 174
Sc D5/D6 = SEQ ID NO: 172

Fig. 7

| Residue Position | 1 | 2 | 4 | 1 + 2 + 4 |
|---|---|---|---|---|
| Δ4 Desaturase | Y to F (SEQ ID NO: 18) | N to H | N to Q | Y to F<br>N to H<br>N to Q<br>(SEQ ID NO: 16) |
| Δ5/6 Desaturase | F to Y (SEQ ID NO: 24) | H to N (SEQ ID NO: 22) | Q to N | F to Y<br>H to N<br>Q to N<br>(SEQ ID NO: 8) |

Fig. 8

| SEQ ID NO. | Primers Used for Constructing Chimera Genes | SEQ ID NO. | Primers Used for Site-directed Mutagenesis |
|---|---|---|---|
| 27 | D4-FLF: AGTGAAGATGGGAGGTGGAGG | 51 | Sfhyqimmt-F: TTCCACTACCAGATAATGATGACCATGATT |
| 28 | D4-FLR: ATAGAGTTCATTTATGGAGATATGCATCA | 52 | Sfhyqimmt-R: GTCATCATTATCTGGTAGTGGAAAAAAACTG |
| 29 | D5/6-FLF: GTGAGGATGGGAGGTGGAGGT | 53 | Synynllki-F: AACTATAACTTGCTGAAAATCATGATT |
| 30 | D5/6-FLR: GGTCATTTATGGAGATATGCATCAAG | 54 | Synynllki-R: TTTTCAGCAAGTTATAGTTGTAGAAAACTGGA |
| 31 | D4-LIPV-F: CTTCTCATTCCAGTTTTCTACAACTATAAC | 55 | SAD4-YQI-F: CCAGTTTTCTACAACTATCAGATAATGATG |
| 32 | D4-LIPV-R: AAAAACTGGAATAAGAAGTGGTGGC | 56 | SAD4-YQI-R: CATCATTATCTGATAGTTGTAGAAAACTGG |
| 33 | D5/6-LIPV-F: CTTCTTATTCCAGTTTTTTTCCACTACCAG | | |
| 34 | D5/6-LIPV-R: GAAAACTGGAATGAGAAGCGGTGG | | |
| 35 | D45/6-PVYG-F: GCCGGTCTACGGCCTTTTG | 57 | SAD5/6-YNLL-F: TTTCCACTACAACTTGCTGAAAATCAT |
| 36 | D45/6-PVYG-R: CAAAAAGGCCGTAGACCGGC | 58 | SAD5/6-YNLL-R: ATGATTTTCAGCAAGTTGTAGTGGAAA |
| 37 | D45/6-MPRH-F: ATGCCGCGCCACAACTAC | 59 | SAD4-FHY-F: TCCAGTTTTCTACCACTATAACATAAT |
| 38 | D45/6-MPRH-R: GTAGTTGTGGCGCGGCAT | 60 | SAD4-FHY-R: ATTATGTTATAGTGGTAGAAAACTGGA |
| 39 | D5/6-WCLS-F: CTGTCTTGGTGCTTGTCCTTCTACCTT | 61 | SAD5/6-FNY-F: GTTTTTTTCAACTACCAGTTGCT |
| 40 | D4-WCLS-R: CAAGCACCAAGACAGATCCACATAG | 62 | SAD5/6-FNY-R: AGCAACTGGTAGTTGAAAAAAAC |
| 41 | D5/6-WAMT-F: CTGGTGTGGGCCATGACGTTTTACA | 63 | SAD4-FFN-F: TTCCAGTTTTCTTCAACTATAACATAATGA |
| 42 | D5/6-WAMT-R: CATGGCCCACACCAGATCCAGCCAG | 64 | SAD4-FFN-R: TCATTATGTTATAGTTGAAGAAAACTGGAA |
| 43 | Sad4-LIPV-F: TTCCAGTTTTCTACAACTATAACATAATGA | | |
| 44 | Sad4-LIPV-R: TCATTATGTTATAGTTGTAGAAAACTGGAA | | |
| 45 | Sad5/6-LIPV-F: ATTCCAGTTTTTTTCCACTACCAGT | 65 | SAD5/6-FYHY-F: CCAGTTTTTTACCACTACCAGTTGCT |
| 46 | Sad5/6-LIPV-R: ACTGGTAGTGGAAAAAAACTGGAAT | 66 | SAD5/6-FYHY-R: AGCAACTGGTAGTGGTAAAAAACTGG |
| 47 | D4-IMI-F: AAATCATGATTACTCGCCGTGACTA | 67 | SAD4-FHYN-F: CCAGTTTTCTTCCACTATAACATAATG |
| 48 | D5/6-IMI-R: GAGTAATCATGATTTTCAGCAACTGG | 68 | SAD4-FHYN-R: CATTATGTTATAGTGGAAGAAAACTGG |
| 49 | D5/6-TMI-F: CATGATTTCTCACCGCTACTG | 69 | SAD5/6-YNYQ-F: CCAGTTTTTTACAACTACCAGTTGC |
| 50 | D4-TMI-R: CGGTGAGAAATCATGGTCATCATTATGTTATAG | 70 | SAD5/6-YNYQ-R: GCAACTGGTAGTTGTAAAAAACTGG |

Fig. 9

| Chimeric protein | Nucleic acid sequence (SEQ ID NO.) | Amino acid sequence (SEQ ID NO.) |
|---|---|---|
| Sig-6C | 1 | 2 |
| Sig-8C | 3 | 4 |
| Sig-14C | 5 | 6 |
| Sig-18C | 7 | 8 |
| Sig-5C | 9 | 10 |
| Sig-7C | 11 | 12 |
| Sig-13C | 13 | 14 |
| Sig-17C | 15 | 16 |
| Sig-23C | 17 | 18 |
| Sig-25C | 19 | 20 |
| Sig-22C | 21 | 22 |
| Sig-24C | 23 | 24 |
| Sig-26C | 25 | 26 |

Fig. 10A

```
                        1                                                    50
Sig-13C protein    (1)  MGGGGQLGESGENGCKSAAGVYTWEEVQHHSNRNDQWLVIDRKVYNVTQW
Sig-17C protein    (1)  MGGGGQLGESGENGCKSAAGVYTWEEVQHHSNRNDQWLVIDRKVYNVTQW
Sig-25C protein    (1)  MGGCGQLGESGENGCKSAAGVYTWEEVQHHSNRNDQWLVIDRKVYNVTQW
Sig-23C protein    (1)  MGGGGQLGESGENGCKSAAGVYTWEEVQHHSNRNDQWLVIDRKVYNVTQW
 Sig-7C protein    (1)  MGGGGQLGESGENGCKSAAGVYTWEEVQHHSNRNDQWLVIDRKVYNVTQW
 Sig-6C protein    (1)  MGGGGQPRESGEP--GSSPAVYTWEEVQHHSSRNDQWLVIDRKVYNISQW
 Sig-5C protein    (1)  MGGCGQLGESGENGCKSAAGVYTWEEVQHHSNRNDQWLVIDRKVYNVTQW
 Sig-8C protein    (1)  MGGGGQPRESGEP--GSSPAVYTWEEVQHHSSRNDQWLVIDRKVYNISQW
Sig-14C protein    (1)  MGGGGQPRESGEP--GSSPAVYTWEEVQHHSSRNDQWLVIDRKVYNISQW
Sig-18C protein    (1)  MGGGGQPRESGEP--GSSPAVYTWEEVQHHSSRNDQWLVIDRKVYNISQW
Sig-22C protein    (1)  MGGGCQPRESGEP--GSSPAVYTWEEVQHHSSRNDQWLVIDRKVYNISQW
Sig-24C protein    (1)  MGGGGQPRESGEP--GSSPAVYTWEEVQHHSSRNDQWLVIDRKVYNISQW
Sig-26C protein    (1)  MGGGGQPRESGEP--GSSPAVYTWEEVQHHSSRNDQWLVIDRKVYNISQW
                        51                                                  100
Sig-13C protein   (51)  AKRHPGGFRVLNHYAGEDATEAFTAFHPDLKFVQKYMKPLLVGELAATEP
Sig-17C protein   (51)  AKRHPGGFRVLNHYAGEDATEAFTAFHPDLKFVQKYMKPLLVGELAATEP
Sig-25C protein   (51)  AKRHPGGFRVLNHYAGEDATEAFTAFHPDLKFVQKYMKPLLVGELAATEP
Sig-23C protein   (51)  AKRHPGCFRVLNHYAGEDATEAFTAFHPDLKFVQKYMKPLLVGELAATEP
 Sig-7C protein   (51)  AKRHPGGFRVLNHYAGEDATEAFTAFHPDLKFVQKYMKPLLVGELAATEP
 Sig-6C protein   (49)  AKRHPGGYRVIGHYAGEDATEAFTAFHPDLKFVQKFLKPLLIGELAATEP
 Sig-5C protein   (51)  AKRHPGGFRVLNHYAGEDATEAFTAFHPDLKFVQKYMKPLLVGELAATEP
 Sig-8C protein   (49)  AKRHPGGYRVIGHYAGEDATEAFTAFHPDLKFVQKFLKPLLIGELAATEP
Sig-14C protein   (49)  AKRHPGGYRVIGHYAGEDATEAFTAFHPDLKFVQKFLKPLLIGELAATEP
Sig-18C protein   (49)  AKRHPGGYRVIGHYAGEDATEAFTAFHPDLKFVQKFLKPLLIGELAATEP
Sig-22C protein   (49)  AKRHPGGYRVIGHYAGEDATEAFTAFHPDLKFVQKFLKPLLIGELAATEP
Sig-24C protein   (49)  AKRHPGGYRVIGHYAGEDATEAFTAFHPDLKFVQKFLKPLLIGELAATEP
Sig-26C protein   (49)  AKRHPGGYRVIGHYAGEDATEAFTAFHPDLKFVQKFLKPLLIGELAATEP
                        101                                                 150
Sig-13C protein  (101)  SQDQDKNAALIQDFHTLRQQAESEGLFQARPLFFLLHLGHILLLEALALL
Sig-17C protein  (101)  SQDQDKNAALIQDFHTLRQQAESEGLFQARPLFFLLHLGHILLLEALALL
Sig-25C protein  (101)  SQDQDKNAALIQDFHTLRQQAESEGLFQARPLFFLLHLGHILLLEALALL
Sig-23C protein  (101)  SQDQDKNAALIQDFHTLRQQAESEGLFQARPLFFLLHLGHILLLEALALL
 Sig-7C protein  (101)  SQDQDKNAALIQDFHTLRQQAESEGLFQARPLFFLLHLGHILLLEALALL
 Sig-6C protein   (99)  SQDRNKNAALIQDFHTLRQQAESEGLFQARPLFFLLHLGHILLLEALALL
 Sig-5C protein  (101)  SQDQDKNAALIQDFHTLRQQAESEGLFQARPLFFLLHLGHILLLEALALL
 Sig-8C protein   (99)  SQDRNKNAALIQDFHTLRQQAESEGLFQARPLFFLLHLGHILLLEALALL
Sig-14C protein   (99)  SQDRNKNAALIQDFHTLRQQAESEGLFQARPLFFLLHLGHILLLEALALL
Sig-18C protein   (99)  SQDRNKNAALIQDFHTLRQQAESEGLFQARPLFFLLHLGHILLLEALALL
Sig-22C protein   (99)  SQDRNKNAALIQDFHTLRQQAESEGLFQARPLFFLLHLGHILLLEALALL
Sig-24C protein   (99)  SQDRNKNAALIQDFHTLRQQAESEGLFQARPLFFLLHLGHILLLEALALL
Sig-26C protein   (99)  SQDRNKNAALIQDFHTLRQQAESEGLFQARPLFFLLHLGHILLLEALALL
```

Fig. 10B

```
                      151                                                200
Sig-13C protein (151) MVWHWGTGWLQTLLCAVMLATAQSQAGWLQHDFGHLSVFKKSRWNHLVHK
Sig-17C protein (151) MVWHWGTGWLQTLLCAVMLATAQSQAGWLQHDFGHLSVFKKSRWNHLVHK
Sig-25C protein (151) MVWHWGTGWLQTLLCAVMLATAQSQAGWLQHDFGHLSVFKKSRWNHLVHK
Sig-23C protein (151) MVWHWGTGWLQTLLCAVMLATAQSQAGWLQHDFGHLSVFKKSRWNHLVHK
 Sig-7C protein (151) MVWHWGTGWLQTLLCAVMLATAQSQAGWLQHDFGHLSVFKKSRWNHLVHK
 Sig-6C protein (149) MVWHWGTGWLQTLLCAVMLATAQSQAGWLQHDFGHLSVFKKSRWNHLVHH
 Sig-5C protein (151) MVWHWGTGWLQTLLCAVMLATAQSQAGWLQHDFGHLSVFKKSRWNHLVHK
 Sig-8C protein (149) MVWHWGTGWLQTLLCAVMLATAQSQAGWLQHDFGHLSVFKKSRWNHLVHH
Sig-14C protein (149) MVWHWGTGWLQTLLCAVMLATAQSQAGWLQHDFGHLSVFKKSRWNHLVHH
Sig-18C protein (149) MVWHWGTGWLQTLLCAVMLATAQSQAGWLQHDFGHLSVFKKSRWNHLVHH
Sig-22C protein (149) MVWHWGTGWLQTLLCAVMLATAQSQAGWLQHDFGHLSVFKKSRWNHLVHH
Sig-24C protein (149) MVWHWGTGWLQTLLCAVMLATAQSQAGWLQHDFGHLSVFKKSRWNHLVHH
Sig-26C protein (149) MVWHWGTGWLQTLLCAVMLATAQSQAGWLQHDFGHLSVFKKSRWNHLVHH 201                                                250
Sig-13C protein (201) FVIGHLKGASANWWNHRHFQHHAKPNIFKKDPDINMVDLFVLGETQPVEY
Sig-17C protein (201) FVIGHLKGASANWWNHRHFQHHAKPNIFKKDPDINMVDLFVLGETQPVEY
Sig-25C protein (201) FVIGHLKGASANWWNHRHFQHHAKPNIFKKDPDINMVDLFVLGETQPVEY
Sig-23C protein (201) FVIGHLKGASANWWNHRHFQHHAKPNIFKKDPDINMVDLFVLGETQPVEY
 Sig-7C protein (201) FVIGHLKGASANWWNHRHFQHHAKPNIFKKDPDINMVDLFVLGETQPVEY
 Sig-6C protein (199) FVIGHLKGASANWWNHRHFQHHAKPNIFKKDPDINMVDLFVLGETQPVEY
 Sig-5C protein (201) FVIGHLKGASANWWNHRHFQHHAKPNIFKKDPDINMVDLFVLGETQPVEY
 Sig-8C protein (199) FVIGHLKGASANWWNHRHFQHHAKPNIFKKDPDINMVDLFVLGETQPVEY
Sig-14C protein (199) FVIGHLKGASANWWNHRHFQHHAKPNIFKKDPDINMVDLFVLGETQPVEY
Sig-18C protein (199) FVIGHLKGASANWWNHRHFQHHAKPNIFKKDPDINMVDLFVLGETQPVEY
Sig-22C protein (199) FVIGHLKGASANWWNHRHFQHHAKPNIFKKDPDINMVDLFVLGETQPVEY
Sig-24C protein (199) FVIGHLKGASANWWNHRHFQHHAKPNIFKKDPDINMVDLFVLGETQPVEY
Sig-26C protein (199) FVIGHLKGASANWWNHRHFQHHAKPNIFKKDPDINMVDLFVLGETQPVEY 251                                                300
Sig-13C protein (251) GIKKIKNMPYNHQHKYFFLVAPPLLIPVFFHYQLLKIMIRRDYVDLSWA
Sig-17C protein (251) GIKKIKNMPYNHQHKYFFLVAPPLLIPVFFHYQIMMTMIRRDYVDLSWA
Sig-25C protein (251) GIKKIKNMPYNHQHKYFFLVAPPLLIPVFFHYNIMMTMIRRDYVDLSWA
Sig-23C protein (251) GIKKIKNMPYNHQHKYFFLVAPPLLIPVFFNYNIMMTMIRRDYVDLSWA
 Sig-7C protein (251) GIKKIKNMPYNHQHKYFFLVAPPLLIPVFFHYQLLKIMISHRYWLDLVWC
 Sig-6C protein (249) GVKKIKLMPYNHQHQYFHLIGPPLLIPVFYNYNIMMTMIRRDYVDLSWA
 Sig-5C protein (251) CIKKIKNMPYNHQHKYFFLVAPPLLIPVFFHYQLLKIMISHRYWLDLVWC
 Sig-8C protein (249) GVKKIKLMPYNHQHQYFHLIGPPLLIPVFYNYNIMMTMIRRDYVDLSWA
Sig-14C protein (249) GVKKIKLMPYNHQHQYFHLIGPPLLIPVFYNYNIMMTMISHRYWLDLVWC
Sig-18C protein (249) GVKKIKLMPYNHQHQYFHLIGPPLLIPVFFNYNLLKIMISHRYWLDLVWC
Sig-22C protein (249) GVKKIKLMPYNHQHQYFHLIGPPLLIPVFFNYQLLKIMISHRYWLDLVWC
Sig-24C protein (249) GVKKIKLMPYNHQHQYFHLIGPPLLIPVFYHYQLLKIMISHRYWLDLVWC
Sig-26C protein (249) GVKKIKLMPYNHQHQYFHLIGPPLLIPVFYNYQLLKIMISHRYWLDLVWC
```

Fig. 10C

```
                        301                                                       350
Sig-13C protein  (301)  MFFYLRYMLCYVPVYGLFGSLALMMFARFLESHWFVWVTQMSHLPMDIDN
Sig-17C protein  (301)  MFFYLRYMLCYVPVYGLFGSLALMMFARFLESHWFVWVTQMSHLPMDIDN
Sig-25C protein  (301)  MFFYLRYMLCYVPVYGLFGSLALMMFARFLESHWFVWVTQMSHLPMDIDN
Sig-23C protein  (301)  MFFYLRYMLCYVPVYGLFGSLALMMFARFLESHWFVWVTQMSHLPMDIDN
 Sig-7C protein  (301)  LSFYLRYMCCYVPVYGLFGSLALMMFARFLESHWFVWVTQMSHLPMDIDN
 Sig-6C protein  (299)  MFFYLRYMLCYVPVYGLFGSLALMMFARFLESHWFVWVTQMSHLPMDIDN
 Sig-5C protein  (301)  LSFYLRYMCCYVPVYGLFGSVVLIVFTRFLESHWFVWVTQMNHLPMDINY
 Sig-8C protein  (299)  MFFYLRYMLCYVPVYGLFGSVVLIVFTRFLESHWFVWVTQMNHLPMDINY
Sig-14C protein  (299)  LSFYLRYMCCYVPVYGLFGSVVLIVFTRFLESHWFVWVTQMNHLPMDINY
Sig-18C protein  (299)  LSFYLRYMCCYVPVYGLFGSVVLIVFTRFLESHWFVWVTQMNHLPMDINY
Sig-22C protein  (299)  LSFYLRYMCCYVPVYGLFGSVVLIVFTRFLESHWFVWVTQMNHLPMDINY
Sig-24C protein  (299)  LSFYLRYMCCYVPVYGLFGSVVLIVFTRFLESHWFVWVTQMNHLPMDINY
Sig-26C protein  (299)  LSFYLRYMCCYVPVYGLFGSVVLIVFTRFLESHWFVWVTQMNHLPMDINY
                        351                                                       400
Sig-13C protein  (351)  DKRRDWLSMQLQATCNIEKSFFNDWFSGHLNFQIEHHLFPRMPRHNYHLV
Sig-17C protein  (351)  DKRRDWLSMQLQATCNIEKSFFNDWFSGHLNFQIEHHLFPRMPRHNYHLV
Sig-25C protein  (351)  DKRRDWLSMQLQATCNIEKSFFNDWFSGHLNFQIEHHLFPRMPRHNYHLV
Sig-23C protein  (351)  DKRRDWLSMQLQATCNIEKSFFNDWFSGHLNFQIEHHLFPRMPRHNYHLV
 Sig-7C protein  (351)  DKRRDWLSMQLQATCNIEKSFFNDWFSGHLNFQIEHHLFPRMPRHNYHLV
 Sig-6C protein  (349)  DKRRDWLSMQLQATCNIEKSFFNDWFSGHLNFQIEHHLFPRMPRHNYHLV
 Sig-5C protein  (351)  ENHNDWLSMQLQATCNVEQSLFNDWFSGHLNFQIEHHLFPTMPRHNYHLV
 Sig-8C protein  (349)  ENHNDWLSMQLQATCNVEQSLFNDWFSGHLNFQIEHHLFPTMPRHNYHLV
Sig-14C protein  (349)  ENHNDWLSMQLQATCNVEQSLFNDWFSGHLNFQIEHHLFPTMPRHNYHLV
Sig-18C protein  (349)  ENHNDWLSMQLQATCNVEQSLFNDWFSGHLNFQIEHHLFPTMPRHNYHLV
Sig-22C protein  (349)  ENHNDWLSMQLQATCNVEQSLFNDWFSGHLNFQIEHHLFPTMPRHNYHLV
Sig-24C protein  (349)  ENHNDWLSMQLQATCNVEQSLFNDWFSGHLNFQIEHHLFPTMPRHNYHLV
Sig-26C protein  (349)  ENHNDWLSMQLQATCNVEQSLFNDWFSGHLNFQIEHHLFPTMPRHNYHLV
                        401                                                  445
Sig-13C protein  (401)  APQVQTLCEKHGIPYEVKTLWKGMVDVVRALKKSGDLWLDAYLHK
Sig-17C protein  (401)  APQVQTLCEKHGIPYEVKTLWKGMVDVVRALKKSGDLWLDAYLHK
Sig-25C protein  (401)  APQVQTLCEKHGIPYEVKTLWKGMVDVVRALKKSGDLWLDAYLHK
Sig-23C protein  (401)  APQVQTLCEKHGIPYEVKTLWKGMVDVVRALKKSGDLWLDAYLHK
 Sig-7C protein  (401)  APQVQTLCEKHGIPYEVKTLWKGMVDVVRALKKSGDLWLDAYLHK
 Sig-6C protein  (399)  APQVQTLCEKHGIPYEVKTLWKGMVDVVRALKKSGDLWLDAYLHK
 Sig-5C protein  (401)  VPRVRALCEKHEIPYQVKTLPQAFADIRSLKNSGELWLDAYLHK
 Sig-8C protein  (399)  VPRVRALCEKHEIPYQVKTLPQAFADIRSLKNSGELWLDAYLHK
Sig-14C protein  (399)  VPRVRALCEKHEIPYQVKTLPQAFADIRSLKNSGELWLDAYLHK
Sig-18C protein  (399)  VPRVRALCEKHEIPYQVKTLPQAFADIRSLKNSGELWLDAYLHK
Sig-22C protein  (399)  VPRVRALCEKHEIPYQVKTLPQAFADIRSLKNSGELWLDAYLHK
Sig-24C protein  (399)  VPRVRALCEKHEIPYQVKTLPQAFADIRSLKNSGELWLDAYLHK
Sig-26C protein  (399)  VPRVRALCEKHEIPYQVKTLPQAFADIRSLKNSGELWLDAYLHK
```

METHODS FOR CONVERSION OF THE SUBSTRATE SPECIFICITY OF DESATURASES

CROSS-REFERENCE TO RELATED APPLICATIONS

This application is a divisional of Ser. No. 15/105,080, which is a U.S. National Stage application of International Application No. PCT/IB2014/067021, filed Dec. 17, 2014, which claims the benefit of U.S. Provisional Application No. 61/916,825, filed Dec. 17, 2013; the aforementioned applications are hereby incorporated by reference herein in their entirety.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "H75716A_Seqlisting.txt", which was created on May 6, 2019 and is 114,844 bytes in size. The subject matter of the Sequence Listing is incorporated herein in its entirety by reference.

The present invention relates to methods for the conversion of the substrate specificity of desaturases. Specifically, the present invention pertains to a method for the conversion of the substrate specificity of a delta (Δ) 5 and/or Δ6 desaturase to the substrate specificity of a Δ4 desaturase, the method comprising: identifying regions and/or amino acid residues which control the substrate specificity of (i) the Δ5 and/or Δ6 desaturase and (ii) the Δ4 desaturase; and replacing in the amino acid sequence of the mentioned Δ5 and/or Δ6 desaturase, the regions and/or amino acid residues which control the substrate specificity of the Δ5 and/or Δ6 desaturase, by the corresponding regions and/or amino acid residues which control the substrate specificity of the Δ4 desaturase, thereby converting the substrate specificity of the Δ5 and/or Δ6 desaturase to the substrate specificity of the Δ4 desaturase. The present invention further concerns a method for the conversion of the substrate specificity of a Δ4 desaturase to the substrate specificity of a Δ5 and/or Δ6 desaturase, the method comprising: identifying regions and/or amino acid residues which control the substrate specificity of (i) the Δ4 desaturase and (ii) the Δ5 and/or Δ6 desaturase; and replacing in the amino acid sequence of the indicated Δ4 desaturase, the regions and/or amino acid residues which control the substrate specificity of the Δ4 desaturase, by the corresponding regions and/or amino acid residues which control the substrate specificity of the Δ5 and/or Δ6 desaturase, thereby converting the substrate specificity of the Δ4 desaturase to the substrate specificity of the Δ5 and/or Δ6 desaturase. In addition, the invention encompasses desaturases with converted substrate specificity.

Very long chain polyunsaturated fatty acids such as arachidonic acid (ARA, $20:4_{\omega 6}$), eicosapentaenoic acid (EPA, $20:5_{\omega 3}$), docosapentaenoic acid (DPA, $22:5_{\omega 3}$) and docosahexaenoic acid (DHA, $22:6_{\omega 3}$) are essential components of cell membranes, and are precursors for a group of hormone-like bioactive compounds (eicosanoids and docosanoids) involved in regulation of various physiological activities in animals and humans. The biosynthesis of these fatty acids involves an alternating process of fatty acid desaturation and elongation, mediated by fatty acid desaturases and elongases, respectively.

Fatty acid desaturases act by removing two hydrogen atoms from the fatty acid hydrocarbon chain, resulting in the formation of a double bond (Shanklin et al., 2009; Meesapyodsuk and Qiu, 2012). Three conserved histidine boxes, generally containing the consensus sequences H-X[3-4]-H, H-X[2-3]-H-H and H-X[2]-H-H, are found in almost all fatty acid desaturases (Pereira et al., 2003). These three histidine boxes form the active site of desaturases, and are involved in the formation of a di-iron complex (Sperling et al., 2001; Shanklin et al., 2009). By using site-directed mutagenesis, Shanklin and colleagues (1994) showed that each of the eight histidine residues in these boxes is essential for the catalytic function of the stearoyl-CoA Δ9 desaturase from rat liver. In addition, Broun et al. (1998) modified amino acids in close proximity to the histidine boxes and were able to convert an oleate 12-desaturase to a hydroxylase and vice versa. Similarly, amino acid modifications close to the histidine boxes of *Claviceps purpurea* Δ12 and 15 desaturases also affected the catalytic properties and regioselectivity of the enzymes (Meesapyodsuk et al., 2007).

Several pathways have been suggested for the formation of very long chain Δ4-desaturated fatty acids such as DHA. One route for DHA synthesis uses $18:3_{\omega 3}$ as a substrate, which under-goes a Δ6 desaturation and a Δ6 elongation to produce $20:4_{\omega 3}$, followed by a Δ5 desaturation step and a Δ5 elongation to form $22:5_{\omega 3}$ (Napier et al., 2003; Napier and Sayanova, 2005). Traditionally, due to the lack of observed Δ4 desaturase activity in mammals (Zheng et al., 2004), the main route for production of $22:6_{\omega 3}$ from $22:5_{\omega 3}$ was thought to proceed via a Δ7 elongation and a Δ6 desaturation, producing $24:6_{\omega 3}$, followed by a β-oxidation reaction to remove two carbon units from the fatty acid (Sprecher et al., 1995; Sprecher, 2000). A simpler route for the production of $22:6_{\omega 3}$ from $22:5_{\omega 3}$ is via Δ4 desaturation, and it is noteworthy that the first Δ4 desaturase was cloned in 2001 from the marine protist *Thraustochytrium* (Qiu et al., 2001). Since then, several other groups have identified Δ4 desaturases from protists and microalgae (Meyer et al., 2003; Tonon, 2003; Tripodi et al., 2006; Zhou et al., 2007; Ahmann et al., 2011). Recently, the first vertebrate Δ4 desaturase gene was isolated from the marine teleost fish *Siganus canaliculatus* (*S. canaliculatus*) (Li et al., 2010), which suggests that there might be a more straightforward mechanism available for DHA biosynthesis in vertebrates as well.

To date, the only fish species with demonstrated Δ5 and Δ6 fatty acid desaturation activity are Atlantic salmon, zebrafish and *Siganus canaliculatus* (Hastings et al., 2001; Hastings et al., 2005; Zheng et al., 2005; Li et al., 2010). Atlantic salmon has separate genes encoding Δ5 and Δ6 desaturation activities, whereas zebrafish and *S. canaliculatus* possess bi-functional Δ5/Δ6 fatty acid desaturase genes.

A better understanding of the structure, function and evolution of desaturases, as well as their roles in the biosynthesis of very long chain polyunsaturated fatty acids offers the opportunity to engineer production of these fatty acids, e.g., in transgenic oilseed plants for nutraceutical markets. Polyunsaturated fatty acids (PUFAs) cannot be synthesized de novo by vertebrates and so must be obtained in the diet. To make possible the fortification of food and of feed with polyunsaturated fatty acids, there is therefore a great need for means and methods for the production of these polyunsaturated fatty acids.

The object on which the present invention is based is the provision of such means and measures. This object is achieved by the embodiments which are described in the claims and herein below.

The present invention thus relates to a method for the conversion of the substrate specificity of a delta (Δ) 5 and/or Δ6 desaturase to the substrate specificity of a Δ4 desaturase, the method comprising:
  a) identifying regions and/or amino acid residues which control the substrate specificity of (i) the Δ5 and/or Δ6 desaturase and (ii) the Δ4 desaturase; and
  b) replacing in the amino acid sequence of the Δ5 and/or Δ6 desaturase referred to in step a), the regions and/or amino acid residues which control the substrate specificity of the Δ5 and/or Δ6 desaturase, by the corresponding regions and/or amino acid residues which control the substrate specificity of the Δ4 desaturase, thereby converting the substrate specificity of the Δ5 and/or Δ6 desaturase to the substrate specificity of the Δ4 desaturase.

The present invention further pertains to a method for the conversion of the substrate specificity of a Δ4 desaturase to the substrate specificity of a Δ5 and/or Δ6 desaturase, the method comprising:
  a) identifying regions and/or amino acid residues which control the substrate specificity of (i) the Δ4 desaturase and (ii) the Δ5 and/or Δ6 desaturase; and
  b) replacing in the amino acid sequence of the Δ4 desaturase referred to in step a), the regions and/or amino acid residues which control the substrate specificity of the Δ4 desaturase, by the corresponding regions and/or amino acid residues which control the substrate specificity of the Δ5 and/or Δ6 desaturase, thereby converting the substrate specificity of the Δ4 desaturase to the substrate specificity of the Δ5 and/or Δ6 desaturase.

Although ω3- and ω6-desaturases have been well studied in terms of substrate preference and regiospecificity, relatively little is known about the membrane-bound, "front-end" long chain fatty acid desaturases, such as Δ4-, Δ5- or Δ6 desaturases. For example, the first vertebrate Δ4 desaturase was only recently identified in the marine teleost fish *Siganus canaliculatus* (*S. canaliculatus*), which also possesses a bi-functional Δ5/Δ6 desaturase. *S. canaliculatus* Δ4 and Δ5/Δ6 desaturases are active with both ω3 and ω6 substrates: the Δ4 desaturase acts on 22:5ω3 and 22:4ω6 and the Δ5/Δ6 desaturase on 18:3ω3, 18:2ω6, 20:4ω3, and 20:3ω6 (Li et al., 2010). For instance, the *S. canaliculatus* Δ4 desaturase introduces a double bond at the Δ4 position of DPAω3, thereby producing DHAω3, whereas the *S. canaliculatus* Δ5/Δ6 desaturase introduces a double bond at the Δ6 position of alpha (α)-linolenic acid (ALA, 18:3ω3) to produce stearidonic acid (SDAω3, 18:4ω3). Both enzymes were shown to have a preference for ω3 fatty acids, in the yeast expression system (Li et al., 2010). Although *S. canaliculatus* Δ4 and Δ5/Δ6 desaturases are functionally different in terms of specificity for substrate chain-length and regioselectivity, these enzymes share a high degree of amino acid identity (83%).

As demonstrated in the following Examples, the inventors were able to identify specific regions and amino acid residues in the amino acid sequences of the *S. canaliculatus* Δ4 and Δ5/Δ6 desaturases which cause the functional divergence between these two highly similar desaturases. To this end, a series of chimeric Δ4 and Δ5/Δ6 desaturases of *S. canaliculatus* has been designed, in which regions of one enzyme have been replaced by the corresponding regions of the other, based on amino acid sequence comparisons between the Δ4 and Δ5/Δ6 genes. The inventors have then analyzed the effects of these mutations on the substrate specificity and regioselectivity of the enzymes by functional characterization, in yeast. Surprisingly, heterologous expression of the *S. canaliculatus* Δ4 and Δ5/Δ6 desaturase chimeric polypeptides in yeast indicated that the substitution of a four amino acid region was sufficient to convert a Δ5/6 desaturase to an enzyme with only Δ4 desaturase activity, and vice versa. Specifically, the inventors were able to identify a discrete protein region containing "YNYN" corresponding to position 280-283 in the amino acid sequence of the *S. canaliculatus* Δ4 desaturase (SEQ ID NO: 174), and the corresponding amino acid residues "FHYQ" at position 278-281 in the amino acid sequence of the *S. canaliculatus* Δ5/6-desaturase (SEQ ID NO: 172) which is responsible for both the substrate chain-length specificity and the regioselectivity of the *S. canaliculatus* Δ 4 and Δ 5/6 desaturases. Unexpectedly, the four critical amino acids influencing the substrate specificity and regioselectivity of the *S. canaliculatus* desaturases are predicted to be located in the third putative transmembrane domain. In addition, the inventors were able to produce enzymes having both Δ4- and Δ6 desaturase activity, by single or double amino acid substitutions within the mentioned four amino acid region.

As further illustrated in the following examples, the methods for the conversion of the substrate specificity of a desaturase provided by the present invention are not only limited to the *S. canaliculatus* desaturases but can be used for the conversion of the substrate specificity of any other Δ4, Δ5 and/or Δ6 desaturase as well, especially of "front-end" desaturases as defined herein. Accordingly, said methods of the invention can be used for rationally engineering the substrate specificity and regioselectivity of any desired Δ4, Δ5 and/or Δ6 desaturase, as appreciated by those skilled in the art.

In addition, the invention makes available Δ4, Δ5 and/or Δ6 desaturases with converted substrate specificity, i.e. engineered substrate specificity. Preferably, said desaturases are "front-end" desaturases, as defined elsewhere herein. Such enzymes are particularly appropriate for the production of very long chain polyunsaturated fatty acids (VLCPUFAs), including, for example, DHA, arachidonic acid (ARA), eicosapentaenoic acid (EPA), gamma-linolenic acid (GLA) and stearidonic acid (SDA). These VLCPUFAs have profound effects on the structural function of membranes, and also have important health effects in humans. DHA and ARA are considered crucial in the development of the brain and central nervous system, and deficiencies of DHA and ARA may adversely affect pre- and postnatal development (Crawfort 2000; Rapoport, 2008; Ahmann et al., 2011). VLCPUFAs also induce broad anti-inflammatory responses (Ahmann et al., 2011; Pollak et al., 2012) and consumption of EPA and DHA leads to a reduction in nonfatal and fatal cardiovascular disease events (Thies et al., 2003). Thus, the health benefits provided by these fatty acids make them important products for nutraceutical and pharmaceutical industries.

The term "polypeptide" or "protein" as used herein refers to any chain of amino acids regardless of length or post-translational modification such as glycosylation, palmitoylation, myristoylation or phosphorylation. Considerations for choosing a specific polypeptide having an engineered substrate specificity include, but are not limited to, the pH optimum of the polypeptide, whether the polypeptide is a rate-limiting enzyme or a component thereof, whether the polypeptide used is essential for synthesis of a desired PUFA, and/or whether a co-factor is required by the polypeptide. The expressed polypeptide preferably has characteristics that are compatible with the biochemical environment of its location in the host cell. For example, the polypeptide may have to compete for substrate(s). Analysis of the $K_m$ and specific activity or substrate specificity of a polypeptide in question may be considered in determining the suitability of a given polypeptide for modifying PUFA(s) production, level or profile in a given host cell referred to elsewhere herein. A polypeptide used in a particular situation is one which typically can function under the conditions present in the intended host cell, but otherwise may be any polypeptide with an engineered substrate specificity as described herein and/or being capable of modifying the relative production, level or profile of a/the desired PUFA(s) or any other desired characteristics as discussed herein. The substrate may be naturally or recombinantly produced by the host cell or may be exogenously supplied.

A "desaturase" as referred to herein is a special type of oxygenase that can remove two hydrogens from a hydrocarbon chain, especially from a fatty acyl chain, catalyzing the formation of a double bond in the substrate. Unlike normal oxygenases which directly transfer molecular oxygen to a substrate, a desaturase uses activated molecular oxygen to abstract hydrogens from the substrate creating a carbon/carbon double bond in a fatty acid and a molecule of water. According to their regioselectivity, desaturases are typically categorized as delta (Δ)x desaturase that introduces a double bond at position "x" referred to from the carboxyl end of a fatty acid; or ωy desaturase that introduces a double bond at position "y" referred to from the methyl end. In addition, desaturases can additionally be labelled as v+z or v−z desaturases. The v+z desaturase introduces a double bond at "z" carbons after the pre-existing double bond v, i.e. towards the methyl end, while the v-z desaturase can introduce a double bond at "z" carbons before the pre-existing double bond v, i.e. towards the carboxyl end. An example of a Δx desaturase is the acyl-ACP Δ9 desaturase from plants, a soluble enzyme introducing a first Δ9 double bond into saturated palmitoyl-ACP or stearoyl-ACP. The membrane-bound ω3 desaturase from nematode *Caenorhabditis elegans* is an example of an ωy desaturase that inserts an ω3 double bond into a polyunsaturated fatty acid. An example of v+3 desaturase is the *Claviceps purpurea* Δ12 desaturase that has a preference for introducing double bonds at the Δ12 position, three carbons after the pre-existing double bond at the ninth position, while the Δ4 desaturase from *Thraustochytrium* is catalytically a v−3 desaturase and can only introduce a double bond at position 4 which is three carbons before the pre-existing double bond at the seventh position.

Based on the position of the double bond insertion relative to a pre-existing double bond in a fatty acyl chain, desaturases can also be referred to as "front-end" desaturases or methyl-end desaturases. Unsaturated fatty acids are essential for all living species in which the initial de novo fatty acid synthesis generally results in production of saturated fatty acids with 18 carbons or 16 carbons in length. The first double bond is often inserted at approximately the middle position of a fatty acid chain. Fatty acids with different chain length and double bond position are generated later by various fatty acid modifying enzymes, such as elongases and desaturases. A methyl-end desaturase introduces a double bond between the pre-existing double bond and the methyl-end, while a front-end desaturase inserts a double bond between the pre-existing double bond and the carboxyl end of a fatty acid. Commonly-found membrane-bound ωy and v+z desaturases such as Δ12, Δ15 and ω3 desaturases in plants are examples of methyl-end desaturases, while widely spread v-z desaturases in microorganisms such as Δ4, Δ5, Δ6 and Δ8 desaturases belong to "front-end" desaturases.

Although both methyl-end desaturases and "front-end" desaturases are involved in the biosynthesis of very long chain polyunsaturated fatty acids, their occurrence in living species is not identical. The former is widely present in plants and microorganisms, while the latter mostly occur in animals and microorganisms, although certain types of "front-end" desaturases have been identified in a small number of higher plants, such as borage, echium and conifers. Higher animals including humans lack the methyl-end desaturase such as Δ12, Δ15 and ω3 desaturase. Consequently, they cannot synthesize linoleic acid (LA, 18:2d9,12 or synonymously 18:2Δ9,12) and alpha-linolenic acid (ALA, 18:3d9,12,15) from oleic acid (OA, 18:1d9), the two essential fatty acids that have to be acquired from the diet. LA and ALA are precursors for the biosynthesis of very long chain polyunsaturated fatty acids such as arachidonic acid (20:4n-6, ARA), eicosapentaenoic acid (20:5n-3, EPA) and docosahexaenoic acid (22:6n-3, DHA). To synthesize these fatty acids, LA and ALA are desaturated by a first front-end desaturase—the Δ6 desaturase, introducing a Δ6 double bond into the substrates giving gamma-linolenic acid (GLA, 18:3d6,9,12), in the ω6 pathway, and stearidonic acid (SDA, 18:4d6,9,12,15) in the ω3 pathway, respectively. GLA and SDA are elongated by a Δ6 elongase to dihomo-gamma-linolenic acid (DGLA, 20:3d8,11,14) and eicosatetraenoic acid (ETA, 20:4d8,11,14,17), which are then desaturated by a second front-end desaturase—the Δ5 desaturase, giving rise to arachidonic acid (ARA, 20:4d5,8,11,14) and eicosapentaenoic acid (EPA, 20:5d5,8,11,14,17), respectively. EPA is elongated to docosapentaenoic acid (DPA, 22:5d7,10,13,16,19) which is then desaturated by a third front-end desaturase—the Δ4 desaturase, giving docosahexaenoic acid (DHA, 22:6d4,7,10,13,16,19), in the ω3 pathway. However, mammals including humans lack the Δ4 desaturase. Biosynthesis of DHA in mammals takes "the retro-conversion pathway" which involves two rounds of chain elongation of EPA and another Δ6 desaturation on the elongated product, followed by a single 2-carbon chain shortening of the Δ6 desaturated product in the peroxisome, giving DHA. The Δ8 desaturase is another front-end desaturase involved in the biosynthesis of very long chain polyunsaturated fatty acids. This desaturase works on a branching pathway of the biosynthesis, introducing a Δ8 double bond into elongated products LA or ALA, i.e. 20:2d11,14 or 20:3d11,14,17, giving rise to DGLA and ETA, respectively, which can then be desaturated by a Δ5 desaturase, giving ARA and EPA, as described above (see, e.g., Meesapyodsuk and Qiu, 2012).

Accordingly, the term "Δ5 desaturase" as used herein denotes a fatty acid desaturase which creates a double bond at the $5^{th}$ position from the carboxyl group of a fatty acid. The term "Δ6 desaturase" means a desaturase which desaturates at the $6^{th}$ position from the carboxyl group of a fatty acid, and the term "Δ4 desaturase" denotes a desaturase which desaturates at the $4^{th}$ position from the carboxyl group of a fatty acid. The term "Δ5 and Δ6 desaturase" as referred to herein refers to a bi-functional delta-5/delta-6 desaturase, i.e. an enzyme which is capable of desaturating both at the $5^{th}$ position and the $6^{th}$ position from the carboxyl group of a fatty acid. The term "Δ4 and Δ6 desaturase" as referred to herein refers to a bi-functional delta-4/delta-6 desaturase, i.e. an enzyme which is capable of desaturating both at the $4^{th}$ position and the 6th position from the carboxyl group of a fatty acid.

The term "desaturase activity" or "catalytic activity of a desaturase" as used in the present application refers to the enzymatic activity of a fatty acid desaturase that can catalyze the formation of a double bond between consecutive carbons of one or more fatty acids to produce a mono- or polyunsaturated fatty acid or precursor thereof, including enzymatic activity which desaturates at position 4 (i.e. Δ4 desaturase activity), position 5 (i.e. Δ5 desaturase activity), position 6 (i.e. Δ6 desaturase activity), positions 5 and 6 (i.e. Δ5/Δ6 desaturase activity), or positions 4 and 6 (i.e. Δ4/Δ6 desaturase activity), from the carboxyl group of a fatty acid. The enzymatic or catalytic activity (both terms are interchangeable) of a desaturase can be measured by methods described in the art; see, e.g., Hastings et al., 2001; Hastings et al., 2005; Zheng et al., 2005; Li et al., 2010.

The fatty acid desaturase can be derived from an animal, such as a vertebrate or a mammal, a plant, e.g. a higher plant such as borage, echium and conifers, or a microorganism, including prokaryotes, namely bacteria and archaea and various forms of eukaryotes, comprising the protozoa, fungi, algae, and microscopic plants (green algae). Further organisms from which the fatty acid desaturases referred to herein can be derived from are indicated in the following examples. The term "derived from" as used herein, means that the desaturase can be isolated, e.g., from an animal, plant or microorganism, by cloning methods known in the art and also described elsewhere herein and in the following examples. Alternatively, the sequences of the desaturases can be synthesized by chemical methods known in the art. By using sequence comparisons with known desaturase sequences and/or the identification of conserved domains of desaturases such as the His boxes and/or the cytochrome $b_5$-like domain, further homolog desaturases can be isolated from any desired species or organism, using the mentioned methods. The desaturase activity can be tested by methods described in the art. The corresponding nucleic acid or amino acid sequences of said isolated or synthesized desaturases can be used to engineer the substrate specificity by the methods of the invention. For instance, chimeric polypeptides of different desaturases can be generated, optionally in combination with mutagenesis methods, in order to convert the substrate specificity of any desired desaturase.

The term "substrate" as used herein means one or more fatty acids on which a desaturase acts. Since the fatty acid substrate must fit into the active site of the desaturase before catalysis can occur, only properly designed fatty acids can serve as substrates for a specific desaturase, as known in the art. As set forth above, a fatty acid desaturase introduces double bonds at specific positions in fatty acids of defined chain lengths. Substrates of a respective desaturase in question are well described in the literature (see, e.g., Meesapyodsuk and Qiu, 2007; 2012; Li et al., 2010) and also referred to herein.

The term "substrate specificity" as used herein denotes the specificity of a desaturase (for example, a Δ4 desaturase) for one or more fatty acids (for example, DPA) of defined chain lengths (for example, C22) in which the formation of a double bond between consecutive carbons at specific positions (for example, position 4 or delta-4 or d4 as defined herein) is catalyzed in order to produce a mono- or polyunsaturated fatty acid or precursor thereof (for example, DHA. The term "regioselectivity" or "regiospecificity" of a desaturase as used herein means the selective insertion of a double bond at a specific position in the fatty acyl chain and, thus, can be considered as a particular aspect of the substrate specificity. For instance, the "regioselectivity" or "regiospecificity" of a Δ4 desaturase denotes the selective insertion of a double bond at position 4, in the fatty acyl chain. The term "fatty acid substrate specificity" or "specificity" of a desaturase as used herein refers to the type of fatty acid for which a desaturase shows highest activity in in vivo or in vitro enzymatic assays, when each tested fatty acid substrate is investigated individually in different assays. The term "fatty acid substrate selectivity", or "selectivity" of a desaturase as used herein refers to the type of fatty acid for which a desaturase shows highest activity in in vivo or in vitro enzymatic assays, when all tested fatty acid substrates are investigated together in the same assays. The fatty acid substrate specificity and/or fatty acid substrate selectivity and/or, the fatty acid regioselectivity and/or fatty acid regioselectivity of a desaturase can be determined by methods known in the art (e.g. Domergue et al, 2002) and also shown in the following Examples. For instance, mutagenesis studies such as site-directed mutagenesis can be conducted to determine the structural basis for the substrate and double bond positional specificities displayed by a particular desaturase. Thereafter, functional expression of the mutated desaturase can be carried out, e.g., in yeast, in the presence of exogenously supplied fatty acids. The analysis of the desaturated fatty acids can be carried out, e.g., by gas chromatography.

Δ4, Δ5 and/or Δ6 desaturases can be active with both ω3 and ω6 fatty acid substrates, or can show preferred substrate specificity for either the ω3 or the ω6 fatty acid substrates. A Δ4 desaturase can act, e.g., on 22:5ω3 or 22:4ω6, a Δ5 desaturase on 20:4ω3 or 20:3ω6, a Δ6 desaturase on 18:3ω3 or 18:2ω6, and a Δ5/Δ6 desaturase on 20:4ω3, 20:3ω6, 18:3ω3 or 18:2ω6.

For example, LA and/or ALA can be desaturated by a Δ6 desaturase, introducing a Δ6 double bond into the substrates giving gamma-linolenic acid (GLA, 18:3d6,9,12), in the ω6 pathway, and stearidonic acid (SDA, 18:4d6,9,12,15) in the ω3 pathway, respectively. GLA and/or SDA can be elongated by a Δ6 elongase to dihomo-gamma-linolenic acid (DGLA, 20:3d8,11,14) in the ω6 pathway and/or eicosatetraenoic acid (ETA, 20:4d8,11,14,17) in the ω3 pathway, respectively. DGLA and/or ETA can then be desaturated by a Δ5 desaturase, giving rise to arachidonic acid (ARA, 20:4d5,8,11,14) in the ω6 pathway, and/or eicosapentaenoic acid (EPA, 20:5d5,8,11,14,17) in the ω3 pathway, respectively. ARA and/or EPA can then be elongated to docosatetraenoic acid (DTA, 22:5d7,10,13,16) in the ω6 pathway and/or omega-3 docosapentaenoic acid (DPA, 22:5d7,10,13, 16,19) in the ω3 pathway, respectively. DTA and/or DPA can then be desaturated by a Δ4 desaturase, giving omega-3 docosapentaenoic acid (DPAn-3, 22:5d4,7,10,13,16), in the ω6 pathway, and/or docosahexaenoic acid (DHA, 22:6d4,7, 10,13,16,19), in the ω3 pathway, respectively. Of particular interest in the context of the present invention, are polypeptides with converted, i.e. engineered, substrate specificity, which allow the conversion of the respective substrate to produce very long chain polyunsaturated fatty acids, such as gamma-linolenic acid (GLA, 18:3d6,9,12), stearidonic acid (SDA, 18:4d6,9,12,15), arachidonic acid (20:4n-6, ARA), eicosapentaenoic acid (20:5n-3, EPA) and/or docosahexaenoic acid (22:6n-3, DHA).

The term "identifying regions and/or amino acid residues which control the substrate specificity of a desaturase" referred to herein means to determine the specific parts or fragments of the amino acid sequence and/or specific amino acid residues of a desaturase which are mediating the specificity of said desaturase for (a) distinct fatty acid substrate(s). The determination of regions and/or amino acid residues which control the substrate specificity of a desaturase can be carried out by methods known in the art and include, for example, the generation of chimeric polypeptides, site-directed mutagenesis, crystal structure analysis, 3-D modeling, FIND technology (Alligator Bioscience) or DNA shuffling in directed evolution experiments, Structure-Based Combinatorial Protein Engineering (SCOPE, WO 2005/118861), staggered extension process, overlap extension PCR ('sewing' PCR) etc. For example, for the identification of regions that determine the differences in substrate specificity, a series of chimeric Δ4 and Δ5 and/or Δ6 desaturases can be produced in which regions of one enzyme are substituted by the corresponding regions of the other, based, for instance, on amino acid sequence comparisons between the Δ4 and Δ5 and/or Δ6 desaturases. Then, the effects of these mutations on the substrate specificity and/or catalytic activity of the enzymes can be determined by functional characterization of said chimeric polypeptides, e.g., in yeast, in comparison to the non-mutated enzymes. Upon heterologous expression of the chimeric series, e.g., in yeast, amino acid regions can be identified which are sufficient to convert, e.g., a Δ5 and/or Δ6 desaturase to an enzyme with only Δ4 desaturase activity, and vice versa. In addition, site-directed mutagenesis can be performed to identify specific amino acid residues within the mentioned regions which are relevant for the substrate specificity of a particular desaturase, as shown in the following Examples.

Thereafter, regions and/or amino acid residues which control the substrate specificity of, e.g., a Δ5 and/or Δ6 desaturase can be replaced in the amino acid sequence of said Δ5 and/or Δ6 desaturase, by the corresponding regions and/or amino acid residues which control the substrate specificity of a Δ4 desaturase, thereby converting completely or at least partially the substrate specificity of the Δ5 and/or Δ6 desaturase to the substrate specificity of a Δ4 desaturase. For example, a "complete conversion" of the substrate specificity of the Δ5 and/or Δ6 desaturase to the substrate specificity of a Δ4 desaturase means that such an enzyme exhibits only substrate specificity of the Δ4 desaturase, after replacement of the mentioned regions and/or amino acid residues which control the substrate specificity. Said enzyme is then no longer able to desaturate substrates of the Δ5 and/or Δ6 desaturase. Envisaged by the present application is also a "partial conversion" of the substrate specificity of the Δ5 and/or Δ6 desaturase to the substrate specificity of a Δ4 desaturase which means that such an enzyme exhibits both Δ4 desaturase substrate specificity and Δ5 and/or Δ6 desaturase substrate specificity, after replacement of the mentioned regions and/or amino acid residues that control the substrate specificity.

Alternatively, the regions and/or amino acid residues which control the substrate specificity of the Δ4 desaturase can be replaced in the amino acid sequence of the Δ4 desaturase, by the corresponding regions and/or amino acid residues which control the substrate specificity of the Δ5 and/or Δ6 desaturase, thereby converting the substrate specificity of the Δ4 desaturase to the substrate specificity of the Δ5 and/or Δ6 desaturase.

Alternatively, the regions and/or amino acid residues which control the substrate specificity of the Δ5 desaturase can be replaced in the amino acid sequence of the Δ5 desaturase, by the corresponding regions and/or amino acid residues which control the substrate specificity of the Δ6 desaturase, thereby converting the substrate specificity of the Δ5 desaturase to the substrate specificity of the Δ6 desaturase. Vice versa, the regions and/or amino acid residues which control the substrate specificity of the Δ6 desaturase can be replaced in the amino acid sequence of the Δ6 desaturase, by the corresponding regions and/or amino acid residues which control the substrate specificity of the Δ5 desaturase, thereby converting the substrate specificity of the Δ6 desaturase to the substrate specificity of the Δ5 desaturase.

Methods for this conversion of the substrate specificity of a particular Δ4, Δ5 and/or Δ6 desaturases include conventional cloning methods known in the art, as described, e.g., in Sambrook et al., Molecular cloning. A Laboratory Manual (2001); or Ausubel, Current protocols in molecular biology (2003). Further methods such as "sewing" PCR are described in the following Examples. Accordingly, the term "conversion of substrate specificity" as used herein means altering the substrate specificity of a desaturase for one or more fatty acids of defined chain lengths in which the formation of a double bond between consecutive carbons at specific positions is being catalyzed, to one or more other, i.e. different fatty acids of defined chain lengths in which the formation of a double bond between consecutive carbons at other, i.e. different specific positions, is being catalyzed. The conversion of substrate specificity can concern the change of the substrate specificity of a particular desaturase for a distinct fatty acid substrate, the specific length of a fatty acid and/or the regioselectivity of the desaturase, i.e. the selective insertion of a double bond at a specific position in the fatty acyl chain. For example, a Δ4 desaturase can desaturate the fatty acid substrates 22:5ω3 and 22:4ω6 at position 4, whereas a Δ5 desaturase can act on 20:4ω3 and 20:3ω6 at position 5. Conversion of the substrate specificity of a Δ4 desaturase to the substrate specificity of a Δ5 desaturase means that the Δ4 desaturase is no longer able to desaturate the fatty acid substrates 22:5ω3 and 22:4ω6 at position 4, but instead is capable of desaturating the fatty acid substrates 20:4ω3 and 20:3ω6 at position 5. It is also envisaged by the invention that said Δ4 desaturase with converted substrate specificity is still able to desaturate the fatty acid substrates 22:5ω3 and 22:4ω6 at position 4, but is also capable of desaturating the fatty acid substrates 20:4ω3 and 20:3ω6 at position 5. The conversion of substrate specificity of a desaturase can be performed by methods known in the art, e.g., by designing a series of chimeric polypeptides of the Δ4 desaturase and the Δ5 desaturase, appropriately in combination with site-directed mutagenesis, as described in the following Exampies and in the literature; see, e.g., Cahoon et al., 1997; 1998.

In one aspect of the methods of the invention, the desaturase is an integral membrane fatty acid desaturase. In certain aspects, the desaturase is a microsomal fatty acid desaturase. In a specific aspect of the methods of the invention, the Δ4, Δ5 and/or Δ6 desaturase is a "front-end" desaturase which has high regioselectivity and substrate specificity, due to their structure (Meesapyodsuk and Qiu, 2012). For example, for the front-end borage Δ6 and Δ8 desaturases, the transmembrane domains and carboxyl termini were shown to play a major role in determining substrate specificity and regioselectivity, possibly by contributing to the formation of the substrate binding site (Libisch et al., 2000). "Front-end" desaturases characteristically contain a cytochrome $b_5$-like domain at the N-terminus of the protein, and introduce a double bond between the carboxyl-end of the fatty acid and a pre-existing double bond. Three conserved histidine boxes, generally containing the consensus sequences H-X[3-4]-H, H-X[2-3]-H-H and H-X[2]-H-H, are found in almost all fatty acid desaturases (Pereira et al., 2003). These three histidine boxes form the active site of desaturases, and are involved in the formation of a di-iron complex (Sperling et al., 2001; Shanklin et al., 2009). In "front-end" desaturases, the first histidine residue in the third histidine box is usually replaced by glutamine. This glutamine residue appears to be essential for enzyme activity, since substituting glutamine in this position in a borage Δ6 desaturase with histidine, resulted in enzymatic activity being abolished (Sayanova et al., 2001).

In a more specific aspect of the methods of the invention, the "front-end" desaturase is derived from a plant, animal or microorganism. The animal can be a vertebrate such as a fish, for example *Siganus canaliculatus*, Atlantic salmon, or zebrafish; a mammal such as baboon or human; a plant, e.g. an oil crop, borage, echium or conifers; or a microorganism, including prokaryotes, namely bacteria and archaea and various forms of eukaryotes, comprising the protozoa, fungi, algae, and microscopic plants (green algae).

For example, the Δ4 desaturases can be derived from *Monosiga brevicollis* (SEQ ID NO: 129 of WO 2012/052468, XP_001749702.1), *Euglena gracilis* (SEQ ID NO: 2 of WO 2004/090123), *Emiliana huxleyi* (SEQ ID NO: 6 of WO 2011/006948), *Pavlova lutheri* (AAQ98793.1), *Pavlova salina* or *Rebecca salina* (AAY15136.1), *Sphaeroforma arctica* (AGN91198.1), *Siganus canaliculatus* (SEQ ID NO: 174), *Thalassiosira pseudonana* (SEQ ID NO: 13 of WO 2005/080578), or *Thraustochytrium* sp. (SEQ ID NO: 2 of WO 2002/026946, AAM09688.1).

The Δ6 desaturases can be derived from Atlantic salmon (ADA56788.1, ADA56789.1, NP_001165251.1, NP_001165752.1), *Pythium irregulare* (SEQ ID NO: 8 of WO 2002/026946, AAL13310.1), *Mortierella alpina* (AAL73947.1), *Ostreococcus lucimarinus* (SEQ ID NO: 14 of WO 2008/040787, DAA34893.1), *Ostreococcus tauri* (SEQ ID NO: 90 of WO 2005/083093, XP_003082578.1), *Siganus canaliculatus* (SEQ-ID NO: 172) or *Primula farinosa* (SEQ ID NO: 2 of WO 2003/072784).

The Δ5 desaturase can be derived from *Thraustochytrium* sp. (SEQ-ID NO: 4 of WO 2002/026946, AAM09687.1), *Pavlova salina* or *Rebecca salina* (ABL96295.1), *Mortierella alpina* AAC72755.1), Atlantic salmon (AAL82631.2) or *Siganus canaliculatus* (SEQ-ID NO: 172).

The Δ5/Δ6 desaturase can be derived from *Siganus canaliculatus* (SEQ-ID NO: 172) or zebrafish (*Danio rerio*: Q9DEX7.1).

Further "front-end" desaturases which can be used in the methods of the invention are described, e.g., in Meesapyodsuk and Qiu, 2012.

The nucleic acid molecules of the mentioned desaturases or of a part thereof can be isolated using molecular-biological standard techniques and the sequence information provided herein. Also, for example a homologous sequence or homologous, conserved sequence regions can be identified at the DNA or amino acid level with the aid of comparative algorithms. They can be used as hybridization probe and standard hybridization techniques (such as, for example, those described in Sambrook et al., Molecular Cloning: A Laboratory Manual. 2nd ed., Cold Spring Harbor Laboratory, Cold Spring Harbor Laboratory Press, Cold Spring Harbor, N.Y., 1989), preferably stringent hybridization conditions, for isolating further nucleic acid sequences which can be used in the methods of the invention. Moreover, nucleic acid molecules of the mentioned desaturases or of a part thereof can be isolated by polymerase chain reaction, where oligonucleotide primers which are used on the basis of this sequence or parts thereof (for example a nucleic acid molecule comprising the complete sequence or part thereof can be isolated by polymerase chain reaction using oligonucleotide primers which have been generated based on this same sequence). For example, mRNA can be isolated from cells (for example by means of the guanidinium thiocyanate extraction method of Chirgwin et al. (1979) Biochemistry 18:5294-5299) and cDNA by means of reverse transcriptase (for example Moloney MLV reverse transcriptase, available from Gibco/BRL, Bethesda, Md., or AMV reverse transcriptase, available from Seikagaku America, Inc., St. Petersburg, Fla.). Synthetic oligonucleotide primers for the amplification by means of polymerase chain reaction can be generated based on one of the sequences shown in the indicated accession numbers, the description, the references cited herein, the Examples or the sequence listing. A nucleic acid can be amplified by standard PCR amplification techniques using cDNA or, alternatively, genomic DNA as template and suitable oligonucleotide primers. The nucleic acid amplified thus can be cloned into a suitable vector and characterized by means of DNA sequence analysis. Oligonucleotides which correspond to a desaturase nucleotide sequence can be generated by standard synthetic methods, for example using an automatic DNA synthesizer.

In a further aspect of the methods of the invention, the Δ4, Δ5 and/or Δ6 desaturase have substrate specificity for both ω3 and ω6 substrates, preferably for ω3 substrates.

In certain aspects of the methods of the invention, the substrate specificity of the desaturase is as follows:

The substrate specificity of the Δ4 desaturase is for 22:5ω3 and 22:4ω6. If the substrate 22:5ω3 is desaturared by the Δ4 desaturase, the corresponding product is 22:6ω3. If the substrate 22:4ω6 is used as a substrate by the Δ4 desaturase, the corresponding product is 22:5ω6.

The substrate specificity of the Δ5 desaturase is for 20:4ω3 and 20:3ω6. If the substrate for the Δ5 desaturase is 20:4ω3, the corresponding product is 20:5ω3. If the substrate for the Δ5 desaturase is 20:3ω6, the corresponding product is 20:4ω6.

The substrate specificity of the Δ6 desaturase is for 18:3ω3 and 18:2ω6. If the substrate for the Δ6 desaturase is 18:3ω3, the corresponding product is 18:4ω3. If the substrate for the Δ6 desaturase is 18:2ω6, the corresponding product is 18:3ω6.

The substrate specificity of the Δ5 and/or Δ6 desaturase is for 20:4ω3, 20:3ω6, 18:3ω3 and 18:2ω6. The corresponding products generated by such a bi-functional desaturase have already been indicated when specifying the respective substrates and products of Δ5 desaturase and Δ6 desaturases.

In a specific aspect of the methods of the invention, the Δ4, Δ5 and/or Δ6 desaturase is a fish Δ4, Δ5 and/or Δ6 desaturase, for example, derived from Atlantic salmon, zebrafish *Danio rerio* or *Siganus canaliculatus*. In a more specific aspect, the Δ4, Δ5 and/or Δ6 desaturase is a *Siganus canaliculatus* Δ4, Δ5 and/or Δ6 desaturase. The corresponding sequences of the *S. canaliculatus* Δ4 desaturase is shown in GenBank accession no. GU594278.1. Further, the corresponding sequence of the Δ5/Δ6 desaturase of *S. canaliculatus* is shown in GenBank accession no. EF424276.2. The cDNA of the Δ4 desaturase of *S. canaliculatus* is 1831 bp in length (excluding polyA tail) and contains a 1338 bp open-reading frame (ORF). The deduced protein has 445 amino acids and is 82.7% identical to the Δ5/Δ6 desaturase of *S. canaliculatus*, and 67.8%, 57.8% and 63.6% identical to *Danio rerio* Δ6/Δ5 (AF309556), *Homo sapiens* Δ5 (AF199596) and Δ6 (AF126799), respectively. The deduced polypeptide sequence of the Δ4 desaturase of *S. canaliculatus* has a number of characteristic features of microsomal fatty acyl desaturases (Fad) proteins, including three histidine boxes, an N-terminal cytochrome b5 domain containing the heme-binding motif, and two transmembrane regions. Phylogenetic analysis of fatty acyl desaturases with a variety of fatty acyl desaturases of other species shows that *S. canaliculatus* desaturases are most closely related to marine teleost Δ6 fatty acyl desaturases, and more distantly from lower eukaryotes Δ4 and Δ5 fatty acyl desaturases; Li et al., 2010.

In a still further aspect of the methods of the invention, the regions and/or amino acid residues which control the substrate specificity of the Δ4, Δ5 and/or Δ6 desaturase are localized within a transmembrane domain. Preferably, the transmembrane domain is the third transmembrane domain.

Unexpectedly, the regions and/or amino acid residues which control the substrate specificity of the Δ4, Δ5 and/or Δ6 desaturase of S. canaliculatus are predicted to be localized in the third putative transmembrane domain.

The putative protein topology of a Δ4, Δ5 and/or Δ6 desaturase can be determined by appropriate software known in the art and/or topology prediction methods such as TMHMM, HMMTOP, MEMSAT, TOPPRED, PHD, DAS-TMfilter, Phobius, PredictProtein, SOSUI, TMPred, or TOP-CONS membrane topology prediction software.

In a specific aspect of the invention, the regions and/or amino acid residues which control the substrate specificity of the Δ4 desaturase comprises the amino acid sequence "YNYN" and the regions and/or amino acid residues which control the substrate specificity of the Δ5 and/or Δ6 desaturase comprise the amino acid sequence "FHYQ".

In specific aspects of the methods of the invention, the amino acid sequences of the Δ5 desaturase and/or Δ6 desaturase and the Δ4 desaturase, have a sequence identity of at least 40%, at least 50%, at least 60%, at least 70%, at least 75%, at least 80%, at least 83%, at least 85%, or even at least 90%.

A number of Δ4 and Δ6 desaturases from non-vertebrate sources have previously been identified, including enzymes from Thraustochytrium sp., P. lutheri, T. pseudonana and E. gracilis (Qiu et al., 2001; Meyer et al., 2003; Tonon et al., 2003; Bowler et al., 2008). However, the amino acid sequence similarity among these "front-end" desaturases tends to be low. For example, Thraustochytrium sp. Δ4 (AF 489589) and Δ5 (AF489588) desaturases share only 19% identity, and Mortierella alpina Δ5 (AF054824) and Δ6 desaturases (AF110510) have only 23% identity in the amino acid sequence. Thus, in order to localise regions affecting substrate specificity (including regiospecificity) in the amino acid sequences of desaturases, preferably "front-end" desaturases, which show only low sequence similarity, the analysis of the crystal structure and 3-D modeling can be required to localize the critical regions and/or amino acid residues necessary for interaction with and desaturation of the substrate. For understanding the molecular basis for chain-length recognition and positional placement of double bonds into fatty acids, chimeric and/or mutant enzymes can be designed based on amino acid sequence comparisons of homologous desaturases or on three-dimensional information from the crystal structure of a desaturase to be further analysed. With more closely related enzymes, construction of chimeric or mutant proteins can be sufficient, possibly in combination with site-directed mutagenesis, as demonstrated in the following examples. There, it is shown that the substrate and regiospecifities of fatty acid desaturases as exemplified for the Siganus canaliculatus Δ4 and Δ5/Δ6 desaturases can be modified by the replacement of specific amino acid residues.

The present invention pertains also to a Δ4 desaturase, Δ5 desaturase, Δ6 desaturase, or Δ5/Δ6 desaturase (i.e. bi-functional desaturase) in which the substrate specificity has been converted to the substrate specificity of another desaturase. More specifically, the present invention concerns a Δ5 and/or Δ6 desaturase in which the substrate specificity of the Δ5 and/or Δ6 desaturase has been converted to the substrate specificity of a Δ4 desaturase. In addition, the invention relates to a Δ4 desaturase in which the substrate specificity of the Δ4 desaturase has been converted to the substrate specificity of a Δ5 and/or Δ6 desaturase. For example, in order to generate a Δ4 desaturase in which the substrate specificity of the Δ4 desaturase is converted to the substrate specificity of a Δ5 and/or Δ6 desaturase, the regions and/or amino acid residues which control the substrate specificity of the Δ4 desaturase are being first identified, by methods described elsewhere herein. In addition, the regions and/or amino acid residues which control the substrate specificity of the Δ5 and/or Δ6 desaturase are being determined. Subsequently, the regions and/or amino acid residues which control the substrate specificity of the Δ4 desaturase are replaced by the corresponding regions and/or amino acid residues which control the substrate specificity of the Δ5 and/or Δ6 desaturase, in the amino acid sequence of the Δ4 desaturase. This replacement can be carried out, e.g., by recombinant DNA technology or chemical synthesis. Thereby, the substrate specificity of the Δ4 desaturase can be converted to the substrate specificity of the Δ5 and/or Δ6 desaturase. By using this strategy, it is possible to rationally engineer the substrate specificity and regioselectivity of any desired Δ4, Δ5 and/or Δ6 desaturase, preferably a "front-end" Δ4, Δ5 and/or Δ6 desaturase.

The conversion of the substrate specificity of a desaturase in question can be completely or at least partially. For instance, a complete conversion of the substrate specificity of the Δ4 desaturase to the substrate specificity of a Δ5 and/or Δ6 desaturase can mean that such an enzyme exhibits the substrate specificity of the 5 and/or Δ6 desaturase only, after replacement of the corresponding regions and/or amino acid residues which control the substrate specificity. Such an enzyme is then no longer able to desaturate substrates of the Δ4 desaturase and exhibits Δ5 and/or Δ6 desaturase activity merely, i.e. desaturates substrates of the Δ5 and/or Δ6 desaturase. Envisaged by the present application is also a partial conversion of the substrate specificity of the Δ4 desaturase to the substrate specificity of a Δ5 and/or Δ6 desaturase. This means that such an enzyme exhibits both Δ4 desaturase substrate specificity and Δ5 and/or Δ6 desaturase substrate specificity, after replacement of the mentioned regions and/or amino acid residues that control the substrate specificity.

In certain aspects, the desaturases with converted substrate specificity of the invention are obtainable or obtained by the methods of the invention.

Figure 6:
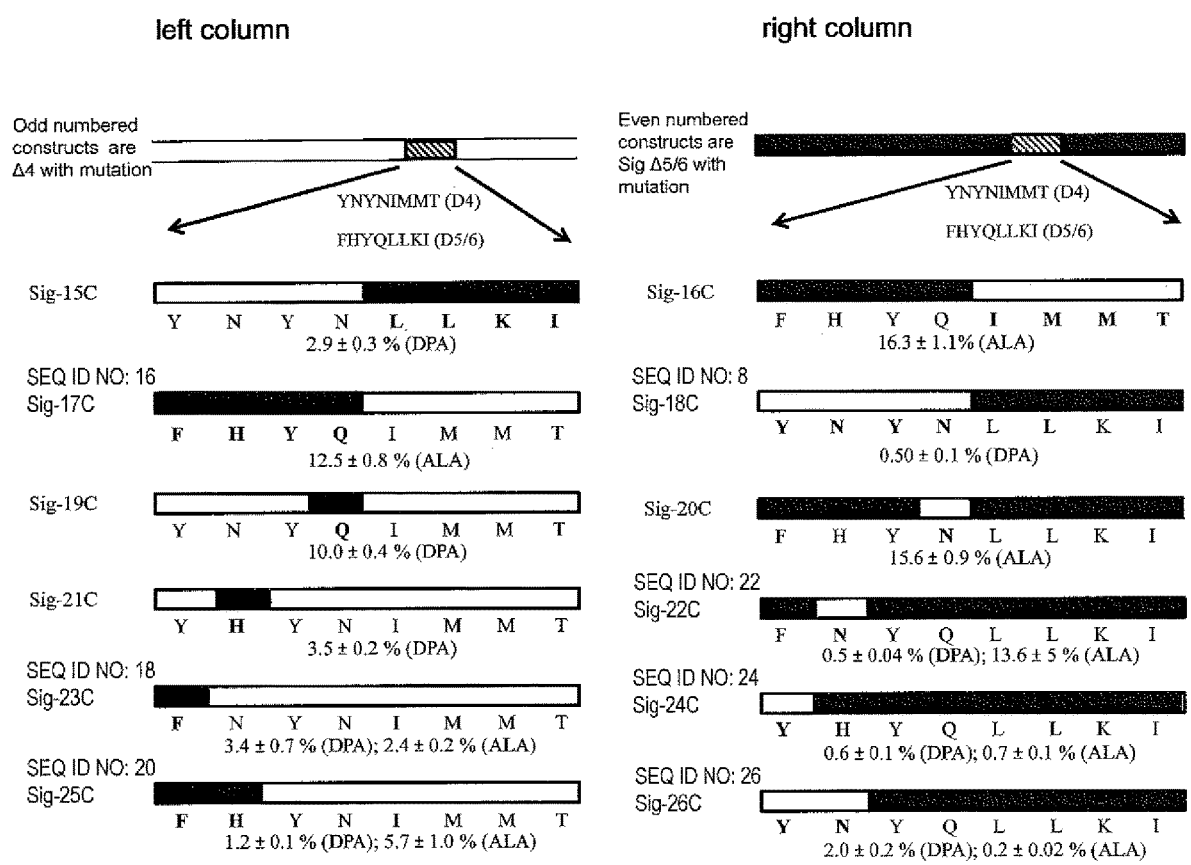

As shown in the following Examples, the present inventors have found that the substitution of a four amino acid region was sufficient to convert a Δ5/6 desaturase to a Δ4 desaturase, and vice versa. A discrete protein region containing the four amino acid residues "YNYN" corresponding to position 280-283 in the amino acid sequence of the S. canaliculatus Δ4 desaturase (SEQ ID NO: 174) has been found to control the substrate specificity of said Δ4 desaturase. The corresponding amino acid residues "FHYQ" at position 278-281 in the amino acid sequence of the S. canaliculatus Δ5/6-desaturase (SEQ ID NO: 172) regulate both the substrate chain-length specificity and the regioselectivity, i.e. the substrate specificity, of the S. canaliculatus Δ 5/6 desaturase. Substitution of the Δ4 desaturase amino acid sequence "YNYN" to the Δ5/Δ6 desaturase sequence "FHYQ" at the same location (Sig-17C; SEQ ID NO: 16; FIG. 6 left column) changed the substrate specificity from the Δ4 desaturase to the Δ5/Δ6 desaturase, $DPA_{\omega 3}$ to ALA (12.5±0.8%). Likewise, altering the S. canaliculatus Δ5/Δ6 desaturase sequence from "FHYQ" to the corresponding "YNYN" sequence (Sig-18C; SEQ ID NO: 8; FIG. 6 right column) resulted in a loss of Δ5/Δ6 desaturase activity but a gain in Δ4 desaturase activity (0.5±0.1%, DPA$_{ω3}$). Thus, the four amino acids that regulate the substrate specificity of *S. canaliculatus* and Δ5/Δ6 desaturases are "YNYN" and the corresponding sequence "FHYQ"; see Example 2. Based on sequence alignments and topology predictions, the corresponding amino acid regions controlling the substrate specificity could be identified, in Δ4, Δ5 and/or Δ6 desaturases of other organisms as well, as illustrated in Example 3. By exchanging the corresponding amino acid regions regulating the substrate specificity shown in said Example, the substrate specificity could also be switched in said Δ4, Δ5 and/or Δ6 desaturases, indicating that the teaching from the *S. canaliculatus* Δ4 and Δ 5/6 desaturases could be readily transferred to other "front-end" desaturases. In particular, this has been exemplified for the Δ6 desaturases of *Ostreococcus tauri* and *Pythium* irregular, and the delta-5 desaturase of *Thraustochytrium* sp.

In one aspect, the present invention concerns a Δ5 and/or Δ6 desaturase in which the substrate specificity of the Δ5 and/or Δ6 desaturase has been converted to the substrate specificity of a desaturase, comprising an amino acid sequence selected from the group consisting of:
  a) an amino acid sequence as shown in SEQ ID NO: 2, 4, 6, or 8; and
  b) an amino acid sequence at least 50% identical to SEQ ID NO: 2, 4, 6, or 8 which is capable of desaturating docosapentaenoic acid (DPA) at position Δ4.

In another aspect, the amino acid sequence referred to in b) has at least 50%, at least 60% and preferably at least 70%, 80%, or 90%, and more preferably at least 85%, 86%, 87%, 88%, 89%, 90%, 91%, 92%, 93%, 94%, 95%, 96%, 97%, 98%, 99% or more sequence identity to the amino acid sequences of SEQ ID NO: 2, 4, 6, or 8 and is capable of desaturating docosapentaenoic acid (DPA) at position Δ4.

In a further aspect, the invention relates to a Δ4 desaturase in which the substrate specificity of the Δ4 desaturase has been converted to the substrate specificity of a Δ5 and/or Δ6 desaturase, comprising the amino acid sequence selected form the group consisting of:
  a) an amino acid sequence as shown in SEQ ID NO: 10, 12, 14, or 16; and
  b) an amino acid sequence at least 50% identical to SEQ ID NO: 10, 12, 14, or 16, and capable of desaturating alpha-linolenic acid (ALA) at position Δ6.

In one aspect, the amino acid sequence referred to in b) has at least 50%, at least 60% and more preferably at least 70%, 80%, or 90%, and most preferably at least 85%, 86%, 87%, 88%, 89%, 90%, 91%, 92%, 93%, 94%, 95%, 96%, 97%, 98%, 99% or more sequence identity to the amino acid sequences of SEQ ID NO: 10, 12, 14, or 16, and is capable of desaturating alpha-linolenic acid (ALA) at position Δ6.

In a specific aspect, the desaturase with converted substrate specificity is a chimeric polypeptide. Preferably, said chimeric polypeptide is artificial and not found in nature.

A Δ4 desaturase in which the substrate specificity is converted to the substrate specificity of a Δ5 and/or Δ6 desaturase, can comprise the complete or partial amino acid sequence of the Δ4 desaturase, except for the regions and/or amino acid residues which control the substrate specificity of the Δ4 desaturase which have been replaced by the corresponding regions and/or amino acid residues which control the substrate specificity of the Δ5 and/or Δ6 desaturase. Alternatively, a Δ5 and/or Δ6 desaturase in which the substrate specificity is converted to the substrate specificity of a Δ4 desaturase, comprises the amino acid sequence of the Δ5 and/or Δ6 desaturase, except for the regions and/or amino acid residues which control the substrate specificity of the Δ5 and/or Δ6 desaturase which have been replaced by the corresponding regions and/or amino acid residues which control the substrate specificity of the Δ4 desaturase. Accordingly, the desaturase with converted substrate specificity is a chimeric polypeptide in that it comprises the above mentioned amino acid sequences of at least two, three or even more different fatty acid desaturases, for example, of a Δ4 desaturase and a Δ5 desaturase, a Δ4 desaturase and a Δ6 desaturase, a Δ5 desaturase and Δ6 desaturase, or a Δ5/Δ6 (bi-functional) desaturase and a Δ4 desaturase. By using this strategy, it is possible to rationally engineer the substrate specificity and regioselectivity of any desired Δ4, Δ5 and/or Δ6 desaturase, preferably a "front-end" Δ4, Δ5 and/or Δ6 desaturase.

Desaturases which can be used for the generation of the chimeric polypeptides of the invention are described elsewhere herein. Said fatty acid desaturases can originate from the same organism or genetically different organisms, for example, the fatty acid desaturases can be derived from the same or different species. For instance, the Δ5 and/or Δ6 desaturase and the Δ4 desaturase can originate from the same species, such as *Siganus canaliculatus*. Alternatively, the Δ5 and/or Δ6 desaturase and the Δ4 desaturase can be derived from different species, for example, the Δ4 desaturase can be a *Siganus canaliculatus* Δ4 desaturase and the Δ5 and/or Δ6 desaturase can be a zebrafish Δ5 and/or Δ6 desaturase. The amino acid sequence of the desaturase in question can be the complete amino acid sequence (except for the region and/or amino acid residues controlling the substrate specificity) or parts thereof. Parts thereof comprise fragments of at least 20, 25, 30, 35, 40, 45, 50, 60, 70, 80, 90, 100, 150, 200, 250 or even more amino acid residues.

The region(s) and/or amino acid residue(s) which control(s) the substrate specificity comprises or consists of at least one, two, three, four, five, six, seven, eight, nine, ten, 11, 12, 13, 14, 15, 20, 25, 30, 35, 40, 45, 50, 60, 70, 80, 90, 100, 150, 200, 250 or even more amino acid residues. For instance, four amino acid residues regulate the substrate specificity of *S. canaliculatus* Δ4 and Δ5/Δ6 desaturases; see Example 2. As acknowledged by those skilled in the art, said four amino acids can be also comprised in longer fragments. Methods for identifying said region(s) and/or amino acid residue(s) which control(s) the substrate specificity are described elsewhere herein.

In order to generate, for example, chimeric polypeptides of a Δ4 desaturase in which the substrate specificity of said Δ4 desaturase is converted to the substrate specificity of a Δ5 and/or Δ6 desaturase, the regions and/or amino acid residues which control the substrate specificity of the Δ4 desaturase are being first identified by methods described elsewhere herein. In addition, the regions and/or amino acid residues which control the substrate specificity of the Δ5 and/or Δ6 desaturase is determined. Subsequently, the regions and/or amino acid residues which control the substrate specificity of the Δ4 desaturase are replaced by the corresponding regions and/or amino acid residues which control the substrate specificity of the Δ5 and/or Δ6 desaturase, in the amino acid sequence of the Δ4 desaturase, e.g., by recombinant DNA technology or chemical synthesis. Thereby, the substrate specificity of the Δ4 desaturase is converted to the substrate specificity of the Δ5 and/or Δ6 desaturase. This process can also be carried out vice versa. By using this strategy, it is possible to rationally engineer the substrate specificity and regioselectivity of any desired Δ4, Δ5 and/or Δ6 desaturase, preferably "front-end" desaturases.

In a still further aspect, the invention relates to a chimeric polypeptide having substrate specificity of a Δ4 desaturase and a Δ6 desaturase, comprising an amino acid sequence selected from the group consisting of:
a) an amino acid sequence as shown in SEQ ID NO: 18, 20, 22, 24 or 26; and
b) an amino acid sequence at least 50% identical to SEQ ID NO: SEQ ID NO: 18, 20, 22, 24 or 26 and comprising the amino acid sequence capable of desaturating docosapentaenoic acid (DPA) at position Δ4 and capable of desaturating alpha-linolenic acid (ALA) at position Δ6.

In one aspect, the amino acid sequence referred to in b) has at least 60% and more preferably at least 70%, 80%, or 90%, and most preferably at least 85%, 86%, 87%, 88%, 89%, 90%, 91%, 92%, 93%, 94%, 95%, 96%, 97%, 98%, 99% or more sequence identity to the amino acid sequences of SEQ ID NO: 18, 20, 22, 24 or 26 and is capable of desaturating docosapentaenoic acid (DPA) at position Δ4 and capable of desaturating alpha-linolenic acid (ALA) at position Δ6.

Surprisingly, bi-functional chimeric polypeptides having substrate specificity of a Δ4 desaturase and a Δ6 desaturase could be generated by the methods of the invention, as shown in the following Examples and in FIG. 6 (see chimeric constructs Sig-22C to Sig-26C). Said bi-functional desaturases are able to desaturate the substrates ALA ω3 and DPA ω3 to produce SDA ω3 and DHA ω3, respectively.

In a specific aspect, the chimeric polypeptide is able to convert at least the substrates ALA ω3 and DPA ω3. Desaturation of these substrates by the novel desaturases of the invention having substrate specificity of a Δ4 desaturase and a Δ6 desaturase produces SDA ω3 and DHA ω3.

The definitions and embodiments presented with respect to the methods of the invention apply mutatis mutandis to the desaturases with converted substrate specificity of the invention, and vice versa.

Further, the present invention relates to the nucleic acid sequences encoding the amino acid sequences of the desaturases with converted substrate specificity, provided by the present invention. Further encompassed by the present invention are derivatives of said nucleic acid sequences having at least 50%, 60%, 70%, 75%, 80%, 85%, 90%, 95%, preferably at least 85%, 86%, 87%, 88%, 89%, 90%, 91%, 92%, 93%, 94%, 95%, 96%, 97%, 98%, 99% or 100% sequence identity or homology with a nucleic acid sequence encoding the desaturases with converted substrate specificity, of the invention. Such derivatives can comprise also functional variants which can be obtained by deletion, insertion, or substitution of nucleotides from/into the sequence. Said variants, however, maintain the desired (i.e. engineered) substrate specificity of the encoded polypeptide. Such variants can be generated by mutagenesis methods known in the art (see, e.g., Sambrook; Ausubel, loc. cit).

"Homologues" means bacterial, fungal, plant or or animal homologues, as indicated elsewhere herein, truncated sequences, single-stranded DNA or RNA of the coding and non-coding DNA sequence and derivatives thereof. In order to determine the percentage of homology (=sequence identity of two amino acid sequences or nucleic acid sequences), the sequences are written one under the other for an optimal comparison (for example, gaps may be introduced into the sequence of a protein or of a nucleic acid in order to generate an optimal alignment with the other protein or the other nucleic acid). Then, the amino acid residues or nucleotides at the corresponding amino acid positions or nucleotide positions are compared. If a position in a sequence is occupied by the same amino acid residue or the same nucleotide as the corresponding position in the other sequence, then the molecules are homologous at this position, i.e. amino acid or nucleic acid "homology" as used in the present context corresponds to amino acid or nucleic acid "identity". The percentage of homology or sequence identity between the two sequences is a function of the number of positions which the sequences share (i.e. percent homology=number of identical positions/total number of positions×100). The terms "homology" and "sequence identity" are therefore considered as synonymous.

The homology or sequence identity is preferably calculated over the entire amino acid or nucleic acid sequence region. The skilled worker has available a series of programs which are based on various algorithms for the comparison of various sequences. Here, the algorithms of Needleman and Wunsch or Smith and Waterman give particularly reliable results. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], can be used for the sequence alignment. The sequence homology values which are indicated above as a percentage can be determined over the entire sequence region using the program GAP and the following settings: Gap Weight: 50, Length Weight: 3, Average Match: 10.000 and Average Mismatch: 0.000. These settings can be used as standard settings for the sequence alignments.

The nucleic acid sequences of the invention which encodes a desaturase with converted substrate specificity provided by the invention, are advantageously introduced into an expression cassette which makes possible the expression of the nucleic acids in organisms such as microorganisms, animals or plants.

Therefore, in another aspect of the invention, there is provided a gene construct comprising a nucleic acid sequence which encodes a desaturase with converted substrate specificity of the invention, operably linked with one or more regulatory sequences.

In the expression cassette, the nucleic acid sequence which encodes a desaturase with converted substrate specificity, is linked operably with one or more regulatory sequences, advantageously for enhancing gene expression. These regulatory sequences are intended to make possible the specific expression of the genes and proteins. Depending on the host organism, this may mean, for example, that the gene is expressed and/or overexpressed only after induction has taken place, or else that it is expressed and/or overexpressed immediately.

For example, these regulatory sequences take the form of sequences to which inductors or repressors bind, thus controlling the expression of the nucleic acid. In addition to these novel regulatory sequences, or instead of these sequences, the natural regulatory elements of these sequences may still be present before the actual structural genes and, if appropriate, may have been genetically modified in such a way that their natural regulation is eliminated and the expression of the genes is enhanced. However, the expression cassette (=expression construct=gene construct) can also be simpler in construction, that is to say no additional regulatory signals have been inserted before the nucleic acid sequence or its derivatives, and the natural promoter together with its regulation was not removed. Instead, the natural regulatory sequence has been mutated in such a way that regulation no longer takes place and/or gene expression is enhanced. These modified promoters can also be positioned on their own before the natural gene in the form of part-sequences (=promoter with parts of the nucleic acid sequences used in accordance with the invention) in order to enhance the activity. Moreover, the gene construct may advantageously also comprise one or more what are known as enhancer sequences in operable linkage with the promoter, which make possible an enhanced expression of the nucleic acid sequence. Additional advantageous sequences such as further regulatory elements or terminator sequences may also be inserted at the 3' end of the DNA sequences. The genes may be present in one or more copies of the expression cassette (=gene construct). Preferably, only one copy of the genes is present in each expression cassette. This gene construct or the gene constructs can be expressed together in the host organism. In this context, the gene construct(s) can be inserted in one or more vectors and be present in the cell in free form, or else be inserted in the genome. It is advantageous for the insertion of further genes in the genome when the genes to be expressed are present together in one gene construct.

In this context, the regulatory sequences or factors can, as described above, preferably have a positive effect on the gene expression of the genes introduced, thus enhancing it. Thus, an enhancement of the regulatory elements, advantageously at the transcriptional level, may take place by using strong transcription signals such as promoters and/or enhancers. In addition, however, enhanced translation is also possible, for example by improving the stability of the mRNA.

The regulatory sequences include, in particular, plant sequences such as promoter and terminator sequences. The constructs can advantageously be stably propagated in microorganisms, in particular in *E. coli* and *Agrobacterium tumefaciens*, under selective conditions and make possible the transfer of heterologous DNA into plants or microorganisms. Useful regulatory sequences are present, for example, in promoters such as the cos, tac, trp, tet, trp-tet, lpp, lac, lpp-lac, laclq, T7, T5, T3, gal, trc, ara, SP6, λ-PR or λ-PL promoter and are advantageously employed in Gram-negative bacteria. Further advantageous regulatory sequences are, for example, present in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzenesulfonamide-inducible), Plant J. 2, 1992:397-404 (Gatz et al., tetracycline-inducible), EP-A-0 335 528 (abscissic acid-inducible) or WO 93/21334 (ethanol- or cyclohexenol-inducible) promoters. Further suitable plant promoters are the cytosolic FBPase promoter or the ST-LSI promoter of potato (Stockhaus et al., EMBO J. 8, 1989, 2445), the *glycine max* phosphoribosyl pyrophosphate amidotransferase promoter (Genbank Accession No. U87999) or the node-specific promoter described in EP-A-0 249 676. Especially advantageous promoters are promoters which make possible the expression in tissues which are involved in the biosynthesis of fatty acids. Very especially advantageous are seed-specific promoters, such as the USP promoter as described, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (*Arabidopsis* oleosin promoter), U.S. Pat. No. 5,504,200 (*Phaseolus vulgaris* phaseolin promoter), WO 91/13980 (*Brassica* Bce4 promoter), by Baeumlein et al., Plant J., 2, 2, 1992:233-239 (LeB4 promoter from a legume), these promoters being suitable for dicots. Examples of promoters which are suitable for monocots are the barley lpt-2 or lpt-1 promoter (WO 95/15389 and WO 95/23230), the barley hordein promoter and other suitable promoters described in WO 99/16890.

In principle, it is possible to use all natural promoters together with their regulatory sequences, such as those mentioned above. It is also possible and advantageous to use synthetic promoters, either in addition or alone, in particular when they mediate seed-specific expression, such as those described in WO 99/16890.

In order to achieve a particular high unsaturated fatty acid content, especially in transgenic plants, the nucleic acid sequences encoding the desaturases with converted substrate specificity of the invention should advantageously be expressed in oil crops, in a seed-specific manner. To this end, seed-specific promoters can be used, or those promoters which are active in the embryo and/or in the endosperm. In principle, seed-specific promoters can be isolated both from dicotyledonous and from monocotyledonous plants. Preferred promoters are listed hereinbelow: USP (=unknown seed protein) and vicilin (*Vicia faba*) [Bäumlein et al., Mol. Gen Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumines B4 (LegB4 promoter) [Bäumlein et al., Plant J., 2, 2, 1992], Lpt2 and lpt1 (barley) [WO 95/15389 and WO95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic-acid-inducible promoter (WO 95/19443), a tetracycline-inducible promoter (Gatz et al. (1992) Plant J. 2, 397-404) and an ethanol-inducible promoter.

To ensure the stable integration of the genes into the transgenic plant over a plurality of generations, each of the nucleic acids which encode the desaturase with converted substrate specificity, optionally in combination with a Δ12 desaturase, ω3 desaturase, Δ9 elongase, Δ6 desaturase, Δ8 desaturase, Δ6 elongase, Δ5 desaturase, Δ5 elongase and/or M desaturase and which are used in the process should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site, advantageously in a polylinker, for insertion of the nucleic acid to be expressed and, if appropriate, a terminator sequence is positioned behind the polylinker. This sequence is repeated several times, preferably three, four or five times, so that up to five genes can be combined in one construct and introduced into the transgenic plant in order to be expressed. Advantageously, the sequence is repeated up to three times. To express the nucleic acid sequences, the latter are inserted behind the promoter via a suitable cleavage site, for example in the polylinker. Advantageously, each nucleic acid sequence has its own promoter and, if appropriate, its own terminator sequence. Such advantageous constructs are disclosed, for example, in DE 101 02 337 or DE 101 02 338. However, it is also possible to insert a plurality of nucleic acid sequences behind a promoter and, if appropriate, before a terminator sequence. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoter, and different terminator sequences can be used in the expression cassette. However, it is also possible to use only one type of promoter in the cassette. This, however, may lead to undesired recombination events.

As described above, the transcription of the genes which have been introduced should advantageously be terminated by suitable terminator sequences at the 3' end of the biosynthesis genes which have been introduced (behind the stop codon). An example of a sequence which can be used in this context is the OCS 1 terminator sequence. As is the case with the promoters, different terminator sequences should be used for each gene.

The gene construct of the present invention may also comprise biosynthesis genes of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA: lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s) and desaturase(s) such as M desaturase, Δ5 desaturase, Δ6 desaturase, Δ8 desaturase, Δ9 desaturase, Δ12 desaturase or Δ6 elongase.

These additional nucleic acids or genes can be cloned into the expression cassettes, which are then used for transforming plants with the aid of vectors such as *Agrobacterium*.

Here, the regulatory sequences or factors can, as described above, preferably have a positive effect on, and thus enhance, the expression genes which have been introduced. Thus, enhancement of the regulatory elements can advantageously take place at the transcriptional level by using strong transcription signals such as promoters and/or enhancers. However, an enhanced translation is also possible, for example by improving the stability of the mRNA. In principle, the expression cassettes can be used directly for introduction into the plants or else be introduced into a vector.

Therefore, in yet another aspect of the invention, there is provided a vector comprising a nucleic acid or a gene construct encoding the desaturase with converted substrate specificity in any of the aspects of the invention described above.

In one embodiment, the vector may be a cloning vector.

The nucleic acid sequences encoding the desaturases with converted substrate specificity of the invention may be introduced alone, or preferably, in combination with an expression cassette (nucleic acid construct) into an organism. To introduce the nucleic acids, the latter are advantageously amplified and ligated in the known manner. Preferably, a procedure following the protocol for Pfu DNA polymerase or a Pfu/Taq DNA polymerase mixture is followed. The primers are selected taking into consideration the sequence to be amplified. The primers should advantageously be chosen in such a way that the amplificate comprises the entire codogenic sequence from the start codon to the stop codon. After the amplification, the amplificate is expediently analyzed. For example, a gel-electrophoretic separation can be carried out, which is followed by a quantitative and a qualitative analysis. Thereafter, the amplificate can be purified following a standard protocol (for example Qiagen). An aliquot of the purified amplificate is then available for the subsequent cloning step.

Suitable cloning vectors are generally known to the skilled worker. These include, in particular, vectors which are capable of replication in microbial systems, that is to say mainly vectors which ensure efficient cloning in yeasts or fungi and which make possible the stable transformation of plants. Those which must be mentioned in particular are various binary and cointegrated vector systems which are suitable for the T-DNA-mediated transformation. Such vector systems are, as a rule, characterized in that they comprise at least the vir genes required for the *Agrobacterium*-mediated transformation and the T-DNA-delimiting sequences (T-DNA border). These vector systems advantageously also comprise further cis-regulatory regions such as promoters and terminator sequences and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, while a second one bears T-DNA, but no vir gene. Owing to this fact, the last-mentioned vectors are relatively small, easy to manipulate and to replicate both in *E. coli* and in *Agrobacterium*. These binary vectors include vectors from the series pBIB-HYG, pPZP, pBecks, pGreen. In accordance with the invention, Bin19, pB1101, pBinAR, pGPTV and pCAMBIA are used by preference. An overview of the binary vectors and their use is found in Hellens et al, Trends in Plant Science (2000) 5, 446-451. In order to prepare the vectors, the vectors can first be linearized with restriction endonuclease(s) and then modified enzymatically in a suitable manner. Thereafter, the vector is purified, and an aliquot is employed for the cloning step. In the cloning step, the enzymatically cleaved and, if appropriate, purified amplificate is cloned with vector fragments which have been prepared, in a similar manner using ligase. In this context, a particular nucleic acid construct, or vector or plasmid construct, can have one or else more than one codogenic gene segment. The codogenic gene segments in these constructs are preferably linked operably with regulatory sequences. The regulatory sequences include, in particular, plant sequences such as the above-described promoters and terminator sequences. The constructs can advantageously be stably propagated in microorganisms, in particular in *E. coli* and *Agrobacterium tumefaciens*, under selective conditions and make possible the transfer of heterologous DNA into plants or microorganisms.

The nucleic acids used in the process, the inventive nucleic acids and nucleic acid constructs, can be introduced into organisms such as microorganisms or advantageously plants, advantageously using cloning vectors, and thus be used in the transformation of plants such as those which are published and cited in: Plant Molecular Biology and Biotechnology (CRC Press, Boca Raton, Fla.), Chapter 6/7, p. 71-119 (1993); F. F. White, Vectors for Gene Transfer in Higher Plants; in: Transgenic Plants, Vol. 1, Engineering and Utilization, Ed.: Kung and R. Wu, Academic Press, 1993, 15-38; B. Jenes et al., Techniques for Gene Transfer, in: Transgenic Plants, Vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Thus, the nucleic acids, the inventive nucleic acids and nucleic acid constructs, and/or vectors used in the process can be used for the recombinant modification of a broad spectrum of organisms, advantageously plants, so that the latter become better and/or more efficient producers of unsaturated fatty acids, as referred to herein.

A series of mechanisms exist by which a modification of the desaturase with converted substrate specificity is possible, so that the yield, production and/or production efficiency of the advantageous unsaturated fatty acids in a plant, preferably in an oil crop plant or a microorganism, can be influenced directly owing to this modified desaturase protein. The number or activity of the proteins or genes can be increased, so that greater amounts of the gene products and, ultimately, greater amounts of the unsaturated fatty acids as referred to herein are produced. A de novo synthesis in an organism which has lacked the activity and ability to biosynthesize the fatty acids prior to introduction of the corresponding gene(s) is also possible. This applies analogously to the combination with further desaturases or elongases or further enzymes of the fatty acid and lipid metabolism. The use of various divergent sequences, i.e. sequences which differ at the DNA sequence level, may also be advantageous in this context, or else the use of promoters for gene expression which make possible a different gene expression in the course of time, for example as a function of the degree of maturity of a seed or an oil-storing tissue.

Owing to the introduction of a gene or nucleic acid coding for a desaturase with converted substrate specificity into an organism, alone or in combination with other genes in a cell, it is not only possible to increase biosynthesis flux towards the end product, but also to increase, or to create de novo the corresponding triacylglycerol composition. Likewise, the number or activity of other genes which are involved in the import of nutrients which are required for the biosynthesis of one or more fatty acids, oils, polar and/or neutral lipids, can be increased, so that the concentration of these precursors, cofactors or intermediates within the cells or within the storage compartment is increased, whereby the ability of the cells to produce unsaturated fatty acids as described below is enhanced further. By optimizing the activity or increasing the number of one or more genes which are involved in the biosynthesis of these compounds, or by destroying the activity of one or more genes which are involved in the degradation of these compounds, an enhanced yield, production and/or efficiency of production of fatty acid and lipid molecules in organisms, advantageously in plants, is made possible.

In an alternative embodiment, the vector may be an expression vector designed to transform an organism in which the nucleic acid is to be expressed and the unsaturated fatty acid as referred to herein is synthesized.

These advantageous vectors, preferably expression vectors, comprise the nucleic acids which encode the desaturase with converted substrate specificity.

As used in the present context, the term "vector" refers to a nucleic acid molecule which is capable of transporting another nucleic acid to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as "expression vectors". Usually, expression vectors which are suitable for DNA recombination techniques take the form of plasmids.

In the present description, where the term "plasmid" is used, it should be understood that plasmids can be substituted for other types of expression vector, such as viral vectors, which exert similar functions. Furthermore, the term "vector" is also intended to comprise other vectors with which the skilled worker is familiar, such as phages, viruses such as SV40, CMV, TMV, transposons, IS elements, phasmids, phagemids, cosmids, linear or circular DNA.

The recombinant expression vectors advantageously used in the process of producing PUFAs comprise the nucleic acids or gene construct of the invention in a form which is suitable for expressing the nucleic acids used in a host cell, which means that the recombinant expression vectors comprise one or more regulatory sequences, selected on the basis of the host cells used for the expression, which regulatory sequence(s) is/are linked operably with the nucleic acid sequence to be expressed. In a recombinant expression vector, "linked operably" means that the nucleotide sequence of interest is bound to the regulatory sequence(s) in such a way that the expression of the nucleotide sequence is possible and they are bound to each other in such a way that both sequences carry out the predicted function which is ascribed to the sequence (for example in an in-vitro transcription/translation system, or in a host cell if the vector is introduced into the host cell). The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnolgy, CRC Press, Boca Raton, Fla., Ed.: Glick and Thompson, Chapter 7, 89-108, including the references cited therein. Regulatory sequences comprise those which govern the constitutive expression of a nucleotide sequence in many types of host cell and those which govern the direct expression of the nucleotide sequence only in specific host cells under specific conditions. The skilled worker knows that the design of the expression vector can depend on factors such as the choice of host cell to be transformed, the desired expression level of the protein and the like.

The recombinant expression vectors used can be designed for the expression of the desaturase with converted substrate specificity of the invention, in prokaryotic or eukaryotic cells. This is advantageous since intermediate steps of the vector construction are frequently carried out in microorganisms for the sake of simplicity. For example, the gene or nucleic acid coding for the desaturase with converted substrate specificity of the invention, can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., pp. 1-28, Cambridge University Press: Cambridge), algae (Falciatore et al., 1999, Marine Biotechnology.1, 3:239-251), ciliates of the types: Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella and Stylonychia, in particular of the genus Stylonychia lemnae, using vectors in a transformation method as described in WO 98/01572 and, preferably, in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or nonfusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose-E binding protein and protein A, respectively, is fused with the recombinant target protein.

Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the pTrc vector is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophage which harbors a T7 gn1 gene under the transcriptional control of the lacUV 5 promoter.

Other vectors which are suitable for prokaryotic organisms are known to the skilled worker, these vectors are, for example in *E. coli* pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667.

In a further aspect, the expression vector is a yeast expression vector. Examples for vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable yeast vectors are, for example, pAG-1, YEp6, YEp13 or pEMBLYe23.

As an alternative, the desaturase with converted substrate specificity of the invention can be expressed in insect cells using Baculovirus vectors. Baculovirus expression vectors which are available for the expression of proteins in cultured insect cells (for example Sf9 cells) comprise the pAc series (Smith et al. (1983) Mol. Cell Biol. 3:2156-2165) and the pVL series (Lucklow and Summers (1989) Virology 170: 31-39).

The abovementioned vectors are only a small overview over suitable vectors which are possible. Further plasmids are known to the skilled worker and are described, for example, in: Cloning Vectors (Ed. Pouwels, P. H., et al., Elsevier, Amsterdam-New York-Oxford, 1985, ISBN 0 444 904018). For further suitable expression systems for prokaryotic and eukaryotic cells, see the Chapters 16 and 17 in Sambrook, J., Fritsch, E. F., and Maniatis, T., Molecular Cloning: A Laboratory Manual, 2. edition, Cold Spring Harbor Laboratory, Cold Spring Harbor Laboratory Press, Cold Spring Harbor, N.Y., 1989.

In a further embodiment of the process, the desaturase with converted substrate specificity of the invention can be expressed in single-celled plant cells (such as algae), see Falciatore et al., 1999, Marine Biotechnology 1 (3):239-251 and references cited therein, and in plant cells from higher plants (for example spermatophytes such as arable crops). Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38.

A plant expression cassette preferably comprises regulatory sequences which are capable of governing the expression of genes in plant cells and which are linked operably so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH5 (Gielen et al., EMBO J.

3 (1984) 835 et seq.), which is known as octopine synthase, or functional equivalents thereof, but all other terminator sequences which are functionally active in plants are also suitable.

Since plant gene expression is very often not limited to the transcriptional level, a plant expression cassette preferably comprises other sequences which are linked operably, such as translation enhancers, for example the overdrive sequence, which enhances the tobacco mosaic virus 5'-untranslated leader sequence, which increases the protein/RNA ratio (Gallie et al., 1987, Nucl. Acids Research 15:8693-8711).

As described above, plant gene expression must be linked operably with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CaMV (Franck et al., Cell 21 (1980) 285-294), 19S CaMV (see also U.S. Pat. No. 5,352,605 and WO 84/02913), or plant promoters, such as the promoter of the Rubisco subunit, which is described in U.S. Pat. No. 4,962,028.

Other preferred sequences for use in operable linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmid reticulum, elaioplasts, peroxisomes and other compartments of plant cells.

As described above, plant gene expression can also be achieved via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylicacid-inducible promoter (WO 95/19443), a tetracyclin-inducible promoter (Gatz et al. (1992) Plant J. 2, 397-404) and an ethanol-inducible promoter.

Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as cells of the endosperm and of the developing embryo. Suitable promoters are the oilseed rape napin promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley Ipt2 or Ipt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the sorghum kasirin gene or the rye secalin gene, which are described in WO 99/16890.

Other promoters which are likewise especially suitable are those which bring about a plastidspecific expression, since plastids constitute the compartment in which the precursors and some end products of lipid biosynthesis are synthesized. Suitable promoters, such as the viral RNA polymerase promoter, are described in WO 95/16783 and WO 97/06250, and the clpP promoter from *Arabidopsis*, described in WO 99/46394.

Vector DNA can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

In a further aspect of the invention there is provided a transgenic non human organism comprising at least one nucleic acid, gene construct or vector according to a previous aspect of the invention.

The transgenic nonhuman organism may be a microorganism, a nonhuman animal or a plant.

Host cells which are suitable in principle for taking up the nucleic acid encoding the desaturase with converted substrate specificity of the invention, the gene product according to the invention or the vector according to the invention are all prokaryotic or eukaryotic organisms. The host organisms which are advantageously used are microorganisms such as fungi or yeasts, or plant cells, preferably plants or parts thereof. Fungi, yeasts or plants are preferably used, especially plants, for example plants such as oil crops, which are high in lipid compounds, such as oilseed rape, evening primrose, hemp, thistle, peanut, canola, linseed, soybean, safflower, sunflower, borage, or plants such as maize, wheat, rye, oats, triticale, rice, barley, cotton, cassava, pepper, *Tagetes*, Solanacea plants such as potato, tobacco, eggplant and tomato, *Vicia* species, pea, alfalfa, bushy plants (coffee, cacao, tea), *Salix* species, trees (oil palm, coconut), and perennial grasses and fodder crops. Especially preferred plants according to the invention are oil crops such as soybean, peanut, oilseed rape, canola, linseed, hemp, evening primrose, sunflower, safflower, trees (oil palm, coconut).

The abovementioned nucleic acids encoding the desaturases with converted substrate specificity and desaturases with converted substrate specificity provided by the present invention can be used in a process for the modulation of the production of $\Delta 4$, $\Delta 5$, and/or $\Delta 6$ unsaturated fatty acids in transgenic organisms, advantageously in plants, such as maize, wheat, rye, oats, triticale, rice, barley, soybean, peanut, cotton, *Linum* species such as linseed or flax, *Brassica* species such as oilseed rape, canola and turnip rape, pepper, sunflower, borage, evening primrose and *Tagetes*, Solanaceae plants such as potato, tobacco, eggplant and tomato, *Vicia* species, pea, cassava, alfalfa, bushy plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an enhanced yield, production and/or production efficiency of the Δ4, Δ5, and/or Δ6 unsaturated fatty acids or a reduction of undesired compounds (for example when the modulation of the metabolism of lipids and fatty acids, cofactors and enzymes lead to modifications of the yield, production and/or production efficiency or the composition of the desired compounds within the cells, which, in turn, can affect the production of one or more fatty acids as referred to herein).

The combination of various precursor molecules and biosynthesis enzymes leads to the production of various fatty acid molecules, which has a decisive effect on lipid composition, since Δ4, Δ5, and/or Δ6 unsaturated fatty acids are not only incorporated into triacylglycerol but also into membrane lipids.

Brassicaceae, Boraginaceae, Primulaceae, or Linaceae are particularly suitable for the production of PUFAs, for example stearidonic acid, eicosapentaenoic acid and docosahexaenoic acid. Linseed (*Linum usitatissimum*) is especially advantageously suitable for the production of PUFAs with the nucleic acid sequences encoding desaturases with converted substrate specificity according to the invention, advantageously, as described, in combination with further desaturases and elongases.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonylCoA by acetyl-CoA carboxylase or into acetyl-ACP by acetyl transacylase. After condensation reaction, these two product molecules together form acetoacetyl-ACP, which is converted via a series of condensation, reduction and dehydratization reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., pp. 612-636 and references cited therein; Lengeler et al. (Ed.) (1999) Biology of Procaryotes. Thieme: Stuttgart, N.Y., and the references therein, and Magnuson, K., et al. (1993) Microbiological Reviews 57:522-542 and the references therein). To undergo the further elongation steps, the resulting phospholipid-bound fatty acids must be returned to the fatty acid CoA ester pool. This is made possible by acyl-CoA:lysophospholipid acyltransferases. Moreover, these enzymes are capable of transferring the elongated fatty acids from the CoA esters back to the phospholipids. If appropriate, this reaction sequence can be followed repeatedly.

The synthesized Δ4, Δ5, and/or Δ6 unsaturated fatty acids can be obtained in the form of the free fatty acid or in the form of their esters, for example in the form of their glycerides.

The term "glyceride" is understood as meaning glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances.

For the purposes of the invention, a "glyceride" is furthermore understood as meaning glycerol derivatives. In addition to the above-described fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

Publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engeneering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engeneering, Ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

Phospholipids for the purposes of the invention are understood as meaning phosphatidylcholine, phosphatidylethanolamine, phosphatidylserine, phosphatidylglycerol and/or phosphatidylinositol, advantageously phosphatidylcholine. The terms "production" or "productivity" are known in the art and comprise the concentration of the fermentation product which is formed within a specific period of time and in a specific fermentation volume (for example kg of product per hour per liter). It also comprises the productivity within a plant cell or a plant, that is to say the content of the desired fatty acids produced in the process relative to the content of all fatty acids in this cell or plant. The term "production efficiency" comprises the time required for obtaining a specific production quantity (for example the time required by the cell to establish a certain throughput rate of a fine chemical). The term yield or product/carbon yield is known in the art and comprises the efficiency of the conversion of the carbon source into the product (i.e. the fine chemical). This is usually expressed for example as kg of product per kg of carbon source. By increasing the yield or production of the compound, the amount of the molecules obtained of this compound, or of the suitable molecules of this compound obtained in a specific culture quantity over a specified period of time is increased. The terms biosynthesis or biosynthetic pathway are known in the art and comprise the synthesis of a compound, preferably an organic compound, by a cell from intermediates, for example in a multi-step and strongly regulated process. The terms "catabolism" or "catabolic pathway" are known in the art and comprise the cleavage of a compound, preferably of an organic compound, by a cell to give catabolites (in more general terms, smaller or less complex molecules), for example in a multi-step and strongly regulated process. The term "metabolism" is known in the art and comprises the totality of the biochemical reactions which take place in an organism. The metabolism of a certain compound (for example the metabolism of a fatty acid) thus comprises the totality of the biosynthetic pathways, modification pathways and catabolic pathways of this compound in the cell which relate to this compound.

The invention further relates to a process for the production of a substance which has the structure shown in the general formula I hereinbelow

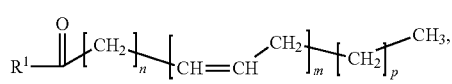

wherein the variables and substituents are as follows:
R$^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

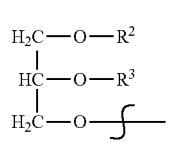

R$^2$=hydrogen, phosphatidylcholine, phosphatidylethanolamine, phosphatidylserine, phosphatidylinositol or a saturated or unsaturated $C_2$ to $C_{24}$-alkylcarbonyl,
R$^3$=hydrogen, a saturated or unsaturated $C_2$ to $C_{24}$-alkylcarbonyl, or R$^2$ and R$^3$ independently of one another are a radical of the formula Ia:

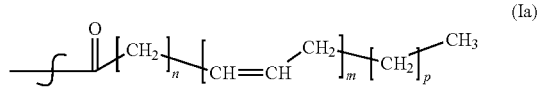

in which
n=2, 3, 4, 5, 6, 7 or 9, m=2, 3, 4, 5 or 6 and p=0 or 3;
and wherein the process comprises the cultivation of (i) a host cell expressing at least one desaturase with converted substrate specificity of the invention or (ii) of a transgenic, nonhuman organism expressing at least one desaturase with converted substrate specificity of the invention under conditions which permit the biosynthesis of the substance. Preferably, the abovementioned substance is provided in an amount of at least 1% by weight based on the total lipid content in the host cell or the transgenic organism. Further, the host cell or transgenic, nonhuman organism used in this process of the invention, can express two, three, four, five, six or more desaturases with converted substrate specificity of the invention.

Preferred alkyl radicals R$^2$ which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These preferred radicals can comprise two, three, four, five or six double bonds. The especially preferred radicals with 20 or 22 carbon atoms in the fatty acid chain comprise up to six double bonds, preferably three, four, five or six double bonds, especially preferably five or six double bonds. All the abovementioned radicals are derived from the corresponding fatty acids.

Preferred alkyl radicals R$^3$ which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These preferred radicals can comprise two, three, four, five or six double bonds. The especially preferred radicals with 20 or 22 carbon atoms in the fatty acid chain comprise up to six double bonds, preferably three, four, five or six double bonds, especially preferably five or six double bonds. All the abovementioned radicals are derived from the corresponding fatty acids.

The abovementioned radicals of R$^1$, R$^2$ and R$^3$ can be substituted by hydroxyl and/or epoxy groups and/or can comprise triple bonds.

The polyunsaturated fatty acids produced in the process according to the invention advantageously comprise at least two, advantageously three, four, five or six, double bonds. The fatty acids especially advantageously comprise four, five or six double bonds. Fatty acids produced in the process advantageously have 18, 20 or 22 C atoms in the fatty acid chain; the fatty acids preferably comprise 20 or 22 carbon atoms in the fatty acid chain. Saturated fatty acids are advantageously reacted to a minor degree, or not at all, with the nucleic acids used in the process. To a minor degree is to be understood as meaning that the saturated fatty acids are reacted with less than 5% of the activity, advantageously less than 3%, especially advantageously with less than 2%, very especially preferably with less than 1, 0.5, 0.25 or 0.125% in comparison with polyunsaturated fatty acids. These fatty acids which have been produced can be produced in the process as a single product or be present in a fatty acid mixture.

The radicals $R^2$ or $R^3$ in the general formulae II may be identical or non-identical, R2 and R3 preferably being a saturated or unsaturated $C_{18}$-$C_{22}$-alkylcarbonyl, especially preferably an unsaturated $C_{18}$-, $C_{20}$- or $C_{22}$-alkylcarbonyl with at least two double bonds.

The polyunsaturated fatty acids produced in the process are advantageously bound in membrane lipids and/or triacylglycerides, but may also occur in the organisms as free fatty acids or else bound in the form of other fatty acid esters. In this context, they may be present as "pure products" or else advantageously in the form of mixtures of various fatty acids or mixtures of different glycerides. The various fatty acids which are bound in the triacylglycerides can be derived from short-chain fatty acids with 4 to 6 C atoms, medium-chain fatty acids with 8 to 12 C atoms or long-chain fatty acids with 14 to 24 C atoms; preferred are long-chain fatty acids, more preferably long-chain fatty acids LCPUFAs of $C_{18}$-, $C_{20}$- and/or $C_{22}$-fatty acids.

The process according to the invention advantageously yields fatty acid esters with polyunsaturated $C_{18}$-, $C_{20}$- and/or $C_{22}$-fatty acid molecules with at least two double bonds in the fatty acid ester, advantageously with at least three, four, five or six double bonds in the fatty acid ester, especially advantageously with at least five or six double bonds in the fatty acid ester and advantageously leads to the synthesis of linoleic acid (=LA, C18:2$^{\Delta9,12}$), γ-linolenic acid (=GLA, C18:3$^{\Delta6,9,12}$), stearidonic acid (=SDA, C18:4$^{\Delta6,9,12,15}$), dihomo-γ-linolenic acid (=DGLA, 20:3$^{\Delta8,11,14}$), ω3-eicosatetraenoic acid (=ETA, C20:4$^{\Delta5,8,11,14}$), arachidonic acid (ARA, C20:4$^{\Delta5,8,11,14}$), eicosapentaenoic acid (EPA, C20:5$^{\Delta5,8,11,14,17}$), ω6-docosapentaenoic acid (C22:5$^{\Delta7,10,13,16}$), ω6-docosatetraenoic acid (C22:4$^{\Delta7,10,13,16}$), ω3-docosapentaenoic acid (=DPA, C22:5$^{\Delta7,10,13,16,19}$), docosahexaenoic acid (=DHA, C22:6$^{\Delta4,7,10,13,16,19}$) or mixtures of these, preferably ARA, EPA and/or DHA. ω3-Fatty acids such as EPA and/or DHA are very especially preferably produced.

The fatty acid esters with polyunsaturated $C_{18}$-, $C_{20}$- and/or $C_{22}$-fatty acid molecules can be isolated in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acylcoenzyme A esters which comprise the polyunsaturated fatty acids with at least two, three, four, five or six, preferably five or six double bonds, from the organisms which have been used for the preparation of the fatty acid esters; advantageously, they are isolated in the form of their diacylglycerides, triacylglycerides and/or in the form of phosphatidylcholine, especially preferably in the form of the triacylglycerides. In addition to these esters, the polyunsaturated fatty acids are also present in the organisms, advantageously the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

The process according to the invention yields the LCPUFAs produced in a content of at least 3% by weight, advantageously at least 5% by weight, preferably at least 8% by weight, especially preferably at least 10% by weight, most preferably at least 15% by weight, based on the total fatty acids in the transgenic organisms, advantageously in a transgenic plant. In this context, it is advantageous to convert $C_{18}$- and/or $C_{20}$-fatty acids which are present in the host organisms to at least 10%, advantageously to at least 20%, especially advantageously to at least 30%, most advantageously to at least 40% to give the corresponding products such as DPA or DHA, to mention just two examples. The fatty acids are advantageously produced in bound form. These unsaturated fatty acids can, with the aid of the nucleic acids used in the process according to the invention, be positioned at the sn1, sn2 and/or sn3 position of the advantageously produced triglycerides. Since a plurality of reaction steps are performed by the starting compounds linoleic acid (C18:2) and linolenic acid (C18:3) in the process according to the invention, the end products of the process such as, for example, arachidonic acid (ARA), eicosapentaenoic acid (EPA), ω6-docosapentaenoic acid or DHA are not obtained as absolutely pure products; minor traces of the precursors are always present in the end product. If, for example, both linoleic acid and linolenic acid are present in the starting organism and the starting plant, the end products such as ARA, EPA or DHA are present as mixtures. The precursors should advantageously not amount to more than 20% by weight, preferably not to more than 15% by weight, especially preferably not to more than 10% by weight, most preferably not to more than 5% by weight, based on the amount of the end product in question. Advantageously, only ARA, EPA or only DHA, bound or as free acids, are produced as end products in a transgenic plant in the process according to the invention. If the compounds ARA, EPA and DHA are produced simultaneously, they are advantageously produced in a ratio of at least 3:2:1 (EPA:ARA:DHA).

Fatty acid esters or fatty acid mixtures produced by the process according to the invention advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acid which is present in the fatty acid esters or fatty acid mixtures is preferably eicosapentaenoic acid. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9- methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tarinic acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselinic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. The fatty acid esters or fatty acid mixtures produced by the process according to the invention advantageously comprise less than 0.1%, based on the total fatty acids, or no butyric acid, no cholesterol, no clupanodonic acid (=docosapentaenoic acid, $C22:5^{\Delta4,8,12,15,21}$) and no nisinic acid (tetracosahexaenoic acid, $C23:6^{\Delta3,8,12,15,18,21}$).

Chemically pure polyunsaturated fatty acids or fatty acid compositions can also be prepared by the processes described above. To this end, the fatty acids or the fatty acid compositions are isolated from the organism, such as the microorganisms or the plants or the culture medium in or on which the organisms have been grown, or from the organism and the culture medium, in a known manner, for example via extraction, distillation, crystallization, chromatography or combinations of these methods. These chemically pure fatty acids or fatty acid compositions are advantageous for applications in the food industry sector, the cosmetic industry sector and especially the pharmacological industry sector.

Vegetable oils rich in mono- or polyunsaturated fatty acids are important in human nutrition and can be used as renewable sources of industrial chemicals. The ability to manipulate carbon chain lengths and double bond positions of mono- or polyunsaturated fatty acids by the desaturases with converted substrate specificity of the invention offers advantageously a way of altering the physical properties (e.g., melting points) and commercial uses of conventional plant oils. Accordingly, the present invention provides methods and compositions for creation of transgenic organisms, such as transgenic plants, with improved or altered PUFA content. PUFA as used herein means polyunsaturated fatty acids which are also referred to as PUFAs, LCPUFA or LCPUFAs (polyunsaturated fatty acids, PUFA, long-chain polyunsaturated fatty acids, LCPUFA). The modification of the fatty acid content of an organism such as a plant presents many advantages including improved nutrition and health benefits. Modification of the fatty acid content can be used to achieve beneficial levels of profiles of desired PUFAs in plant, plant parts and plant products including plant seed oils. For example, when the desired PUFAs are produced in the seed tissue of a plant, the oil may be isolated from the seeds typically resulting in an oil high in desired PUFAs or an oil having a desired fatty acid content or profile, which may in turn be used to provide beneficial characteristics in food stuffs and other products. The desaturases having engineered substrate specificity of a Δ4, Δ5 and/or Δ6 desaturase generated by the methods of the invention and/or provided by the present invention can be advantageously used for the modification of the PUFA content of a cell, for example, modification of the PUFA content of a plant cell or plant cells.

The content of all the references, patent applications, patents and published patent applications cited in the present patent application is hereby incorporated by reference to the respective specific disclosure.

The Figures show:

FIG. 1: Alignment of deduced amino acid sequences of *S. canaliculatus* Δ4 desaturase (GenBank accession number: GU594278.1; SEQ ID NO: 174) and Δ5/Δ6 desaturase (GenBank accession number: EF424276.2; SEQ ID NO: 172) generated by VectorNTI software. Non-identical residues are highlighted in grey. The cytochrome $b_5$-like domain is underlined by a waved line. The four amino acid residues that determine the functional divergence between the two genes are shown in bold. Histidine boxes are underlined by dotted lines and the putative transmembrane domains are underlined with solid lines.

FIG. 2: Putative protein topology of *S. canaliculatus* Δ4 and Δ5/Δ6 desaturases, based on TOPCONS membrane topology prediction software. The membrane topology was generated by restraining N- and C-terminal regions to the inside (cytoplasmic) area. H denotes histidine box. Stars indicate the approximate location of the four amino acid residues involved in substrate chain-length specificity and regiospecificity.

Figure 3:
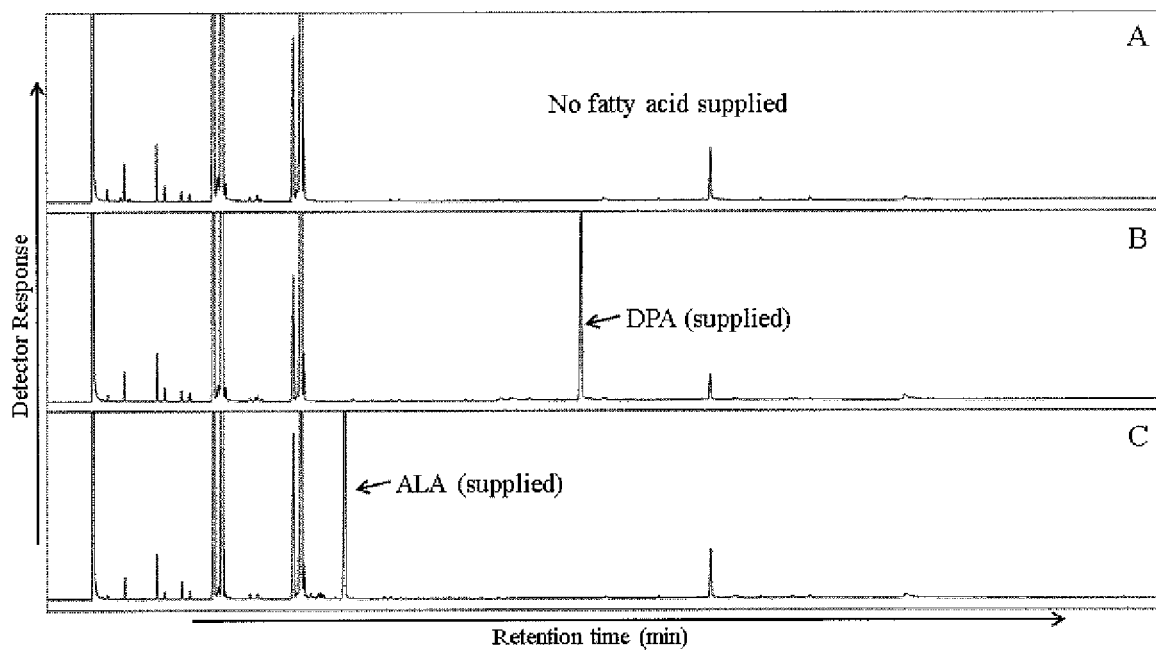

FIG. 3: Gas chromatograms of yeast cells containing an empty pYES2.1/V5-His-TOPO vector. A, no fatty acid supplied; B, DPA supplied exogenously; C, ALA supplied exogenously.

Figure 4:
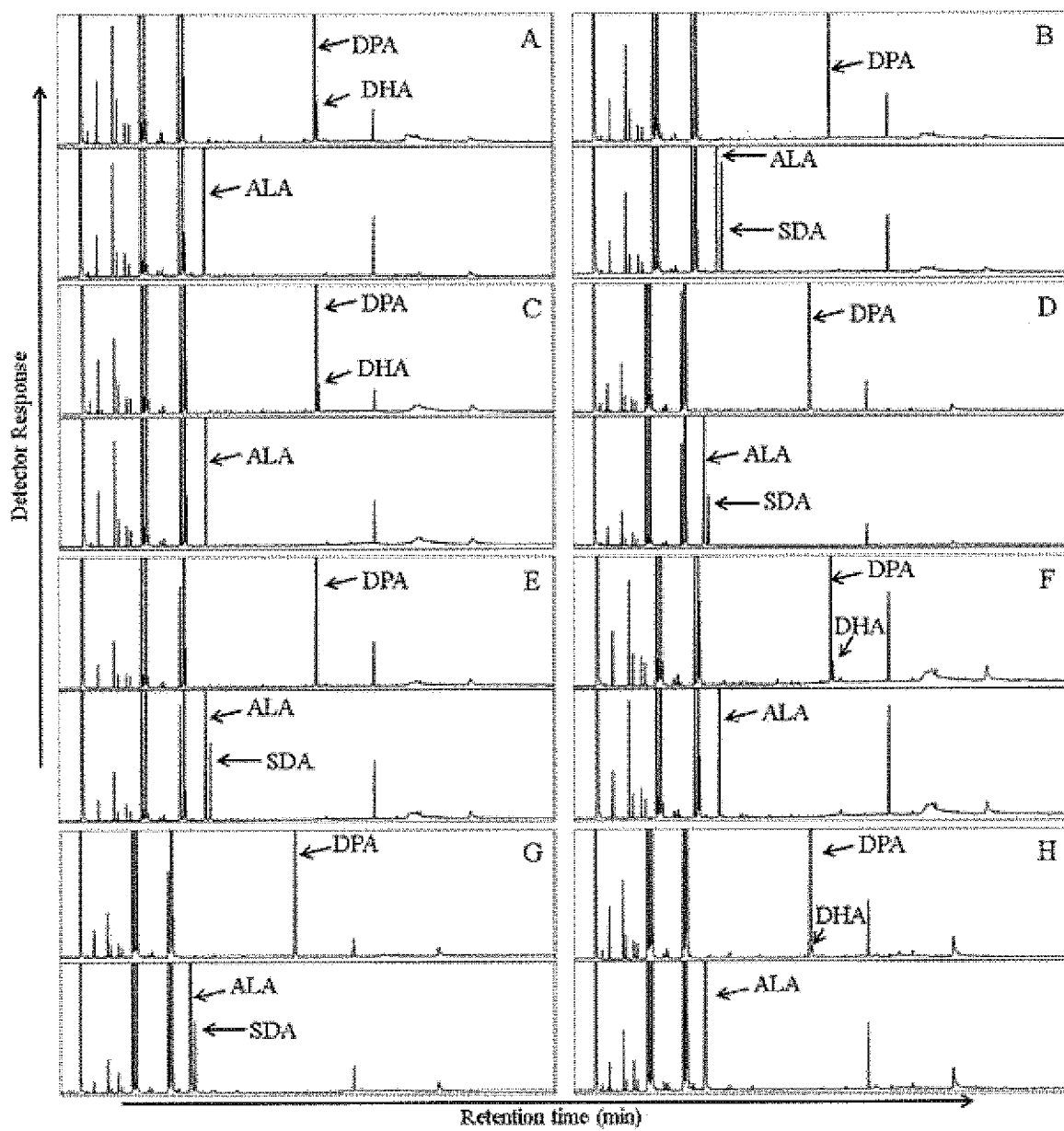

FIG. 4: Gas chromatograms of yeast cells expressing *S. canaliculatus* wild-type and mutated desaturases. A, *S. canaliculatus* Δ4 desaturase (SEQ ID NO: 174); B, *S. canaliculatus* Δ5/Δ6 desaturase (SEQ ID NO: 172); C, chimeric *S. canaliculatus* desaturase Sig-3C; D, chimeric *S. canaliculatus* desaturase Sig-4C; E, chimeric *S. canaliculatus* desaturase Sig-5C (SEQ ID NO: 10); F, chimeric *S. canaliculatus* desaturase Sig-6C (SEQ ID NO: 2); G, chimeric *S. canaliculatus* desaturase Sig-17C (SEQ ID NO: 16) H, chimeric *S. canaliculatus* desaturase Sig-18C (SEQ ID NO: 8). Top and bottom panels show results from cultures supplied with DPA and ALA respectively.

Figure 5:
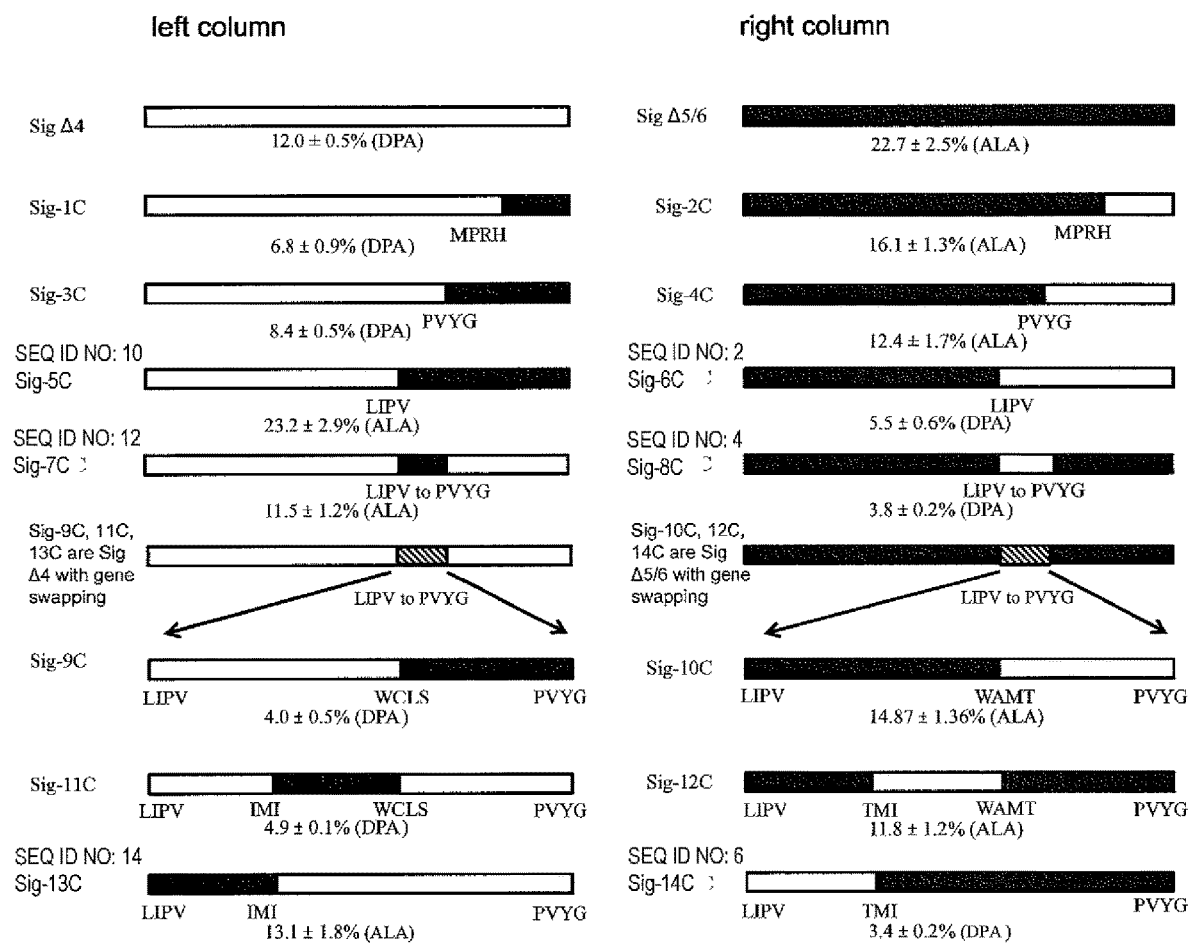

FIGS. 5 and 6: Schematic representation of *S. canaliculatus* Δ4 and Δ5/Δ6 chimeric gene constructs with associated conversion percentages. Substitution of domains within enzymes. FIG. 5: *S. canaliculatus* Δ4 sequence (SEQ ID NO: 174) is represented as a white bar (left) and *S. canaliculatus* Δ5/Δ6 sequence (SEQ ID NO: 172) is represented as a black bar (right).

FIG. 6: Substitutions within a critical eight amino acid region. The amino acid residues shown in each chimeric gene represent the start and end of the domain substitution. The conversion percentages are the mean of three individual assays ±SD. *S. canaliculatus* Δ4 sequence (SEQ ID NO: 174) is represented as a white bar and *S. canaliculatus* Δ5/Δ6 sequence (SEQ ID NO: 172) is represented as a black bar. The bold amino acid residues denote the residues which were changed. The conversion rates are the mean of three individual assays ±SD.

FIG. 7: Amino acid substitutions introduced into the region of Δ4 and Δ5/Δ6 desaturases critical for substrate specificity. Residue numbering is based on the Δ4 and Δ5/Δ6 desaturase amino acid sequences "YNYN" and "FHYQ", respectively. Residues from the Δ4 desaturase were substituted into the corresponding position of the Δ5/Δ6 sequence, and vice versa.

FIG. 8: Primers used in this study for constructing the chimeric proteins of S. canaliculatus Δ4 and Δ5/Δ6 desaturases and site-directed mutagenesis. F: forward primer; R: reverse primer.

FIG. 9: Allocation of the nucleic acid sequences and amino acid sequences of the chimeric S. canaliculatus proteins to the corresponding SEQ ID NOs.

FIG. 10: Alignment of the amino acid sequences of the chimeric S. canaliculatus proteins indicated in FIG. 9.

The invention will now be illustrated by the following Examples which shall, however, not be construed as limiting the scope of the invention.

EXAMPLES

Example 1

Growth and induction media for yeast expression were purchased from MP Biologicals (Solon, Ohio). Fatty acid (DPA$_{ω3}$ and ALA) substrates were purchased from Nu-Chek Prep Inc (Elysian, Minn.). Phusion high fidelity DNA polymerase was from New England Biolabs (Ipswich, Mass.). Taq polymerase was from Invitrogen (Burlington, ON). All HPLC grade solvents were purchased from EMD Inc. (Mississauga, ON) and Fisher Scientific (Ottawa, ON). All chemicals if not mentioned otherwise, were purchased from Sigma-Aldrich (Oakville, ON).

1.1 S. canaliculatus Δ4 and Δ5/Δ6 Desaturases

Sequences encoding the S. canaliculatus Δ4 desaturase (GenBank accession number: GU594278.1; nucleic acid sequence shown in SEQ ID NO: 173 and amino acid sequence shown in SEQ ID NO: 174) and the Δ5/Δ6 desaturase (GenBank accession number: EF424276.2; nucleic acid sequence shown in SEQ ID NO: 171 and amino acid sequence shown in SEQ ID NO: 172) were synthesized by Life Technologies Corporation (Burlington, ON), based on the GenBank database sequences. Synthetic genes were cloned into pYES2.1/V5-His-TOPO (Invitrogen) and sequenced, prior to being used in further experiments.

1.2 Construction of Vectors

Chimeric enzymes were constructed from Δ4 and Δ5/Δ6 fatty acid desaturases by overlap extension PCR ('sewing' PCR), targeting regions in the open reading frame (ORF) of the desaturases. The positions for substitutions were rationally chosen by aligning S. canaliculatus Δ4 and Δ5/Δ6 desaturases to locate the areas with differences in amino acid composition. After regions of interest were identified, overlapping synthetic primers were designed so that fragments from different portions of the genes could be amplified then 'sewn' together to form a chimera gene or gene containing a specific site-directed mutation. The initial chimeric genes were constructed using the synthesized S. canaliculatus Δ4 and Δ5/Δ6 desaturases (Life Technologies) as the DNA template for PCR. Subsequent chimeric genes were constructed using either the S. canaliculatus Δ4 and Δ5/Δ6 desaturases or chimeric genes constructed in this study. The overlap extension PCR was performed using Phusion high fidelity DNA polymerase, a proofreading polymerase which produces blunt-ended DNA products. PCR parameters were as follows: initial denaturation for 2 min at 98° C., followed by 30 cycles of 98° C. denaturation for 30 s, 60° C. annealing for 30 s, and 72° C. extension for 90 s. After amplification, PCR products were subjected to electrophoresis on a 0.8% agarose gel. The DNA band with the appropriate size was cut from the gel and purified using an EZ-10 Spin Column DNA Gel Extraction Kit (Bio Basic Inc., Markham, ON), according to the manufacturer's instructions. Before cloning the purified DNA product into the pYES2.1/V5-His-TOPO yeast expression vector (Invitrogen), an additional post-amplification step using Taq polymerase was performed. This step added 3' A-overhangs to the amplified DNA, which is necessary for TA cloning into the pYES2.1/V5-His-TOPO vector. The addition of a 3' A-overhang was performed by adding 20 μL of gel purified DNA, 2.5 pL 10×PCR buffer minus Mg$^{2+}$, 1.5 μL of 50 mM MgCl$_2$, 0.2 mM dNTP and 2.5 units of Taq polymerase, followed by incubation at 72° C. for 10 min. The amplified DNA fragment was cloned into the pYES2.1/V5-His-TOPO vector according to the manufacturer's instructions, and the plasmid DNA was isolated using an EZ-10 spin column plasmid DNA miniprep kit (Bio Basic Inc.). After sequencing, plasmids were transformed into the S. cerevisiae yeast strain INVSc1 (Invitrogen) using the EasyComp transformation kit (Invitrogen).

1.3 Expression in Yeast

For functional expression of the desaturases, yeast cultures were grown overnight at 30° C. in DOB-URA (yeast synthetic complete media devoid of uracil) containing 2% glucose. The OD600 of the overnight yeast cultures were measured and standardized between samples. The samples were washed with DOB-URA containing 2% galactose and expression was induced with the same media. Expression was carried out for 3 days at 20° C. in the presence of exogenousiy supplied fatty acids (250 μM DPA$_{ω3}$ or ALA depending on the yeast construct).

1.4 Fatty Acid Analysis

After 3 days of growth in the presence of exogenousiy supplied fatty acids, the yeast cells were collected by centrifugation at 2,800 rpm for 3 min and washed once with induction buffer (2% galactose) and washed again with sterile distilled water. Two mL of 3N-methanolic HCl was added to each sample and the samples were heated at 80° C. for 40 min, cooled at room temperature, and the hexane phase containing the fatty acid methyl esters was partitioned from the aqueous phase by the addition of 1 mL 0.9% NaCl and 2 mL hexane, followed by centrifugation. The hexane phase was transferred to glass vials and air-dried under a gentle stream of liquid nitrogen gas and was resuspended in 100 μL of hexane before being analyzed by gas chromatography (GC) from Agilent Technologies Inc. (model: 6890N, Integrated peaks calculated by Agilent ChemStation Software). Desaturation percent was calculated as:

$$100/(product/(substrate+product)).$$

Example 2

2.1 S. canaliculatus Δ4 and Δ5/Δ6 Desaturases have Similar Sequences and Structures The deduced proteins of the Δ4 desaturase (SEQ ID NO: 174) and Δ5/Δ6 desaturase (SEQ ID NO: 174) genes of S. canaliculatus have 445 and 443 amino acids respectively, with the two amino acid gap located in the N-terminal region of the alignment (FIG. 1). Based on membrane topology analysis (TOPCONS; restraining N- and C-terminal inside cytoplasmic area; FIG. 2), both the S. canaliculatus Δ4 and Δ5/Δ6 genes have four predicted transmembrane domains with two linker regions. Both desaturases have three conserved histidine boxes, and an N-terminal cytochrome $b_5$-like domain, which are the characteristic features of a front-end microsomal desaturase (Li et al., 2010). Due to the high similarity in amino acid sequence between the two desaturases, the inventors were able to rationally design primers to produce chimeras based on aligning the open reading frame (ORF) of the S. canaliculatus genes (FIG. 1). Specific corresponding regions were selected and exchanged between the two desaturases to form chimeric proteins. Regions that were quite highly conserved, as well as less conserved regions were substituted.

FIG. 8 lists the primers and corresponding SEQ ID NOs. used for constructing the chimeras and for performing site-directed mutagenesis to identify the roles of specific amino acid residues. This set of primers allowed the inventors to perform substitutions of domains distributed in the hydrophobic transmembrane domains, C-terminal and N-terminal regions and linkers between transmembrane domains, based on the topology analysis shown in FIG. 2.

2.2 A Four Amino Acid Region within the S. canaliculatus Δ4 and Δ5/Δ6 Desaturases Controls Substrate Length and Regiospecificity Both S. canaliculatus desaturases show a preference for ω3 fatty acids (Li et al., 2010). Therefore, the ω3 fatty acids DPA and ALA, which are substrates for the native Δ4- and Δ5/Δ6-desaturases respectively, were used throughout this study. As a negative control, S. ceriviseae INVSc1 cells were transformed with the empty pYES2.1/V5-His-TOPO vector. The fatty acids observed in the control included 14:0, 16:0, 16:1ω7, 18:0 and 18:1ω9 and 26:0, but neither Δ4 nor $DPA_{\omega3}$ activity was observed (FIG. 3). Expression of wild-type S. canaliculatus Δ4 (SEQ ID NO: 174) and Δ5/Δ6 desaturases (SEQ ID NO: 172) in yeast showed desaturase activities of 12.0±0.5% ($DPA_{\omega3}$) and 22.7±2.5% (ALA), respectively (FIGS. 4 and 5; Table 1). The Δ5/Δ6 desaturase did not show activity with $DPA_{\omega3}$, nor did the Δ4 desaturase show activity with ALA (FIGS. 4 and 5; Table 1).

When the S. canaliculatus Δ4 desaturase sequence from the amino acid sequence "MPRH" onward, representing approximately the last one-tenth of the enzyme, was replaced with the Δ5/Δ6 sequence, the enzyme maintained the same substrate specificity but the conversion level dropped by approximately 40% (Sig-1C; FIG. 5 left column). The reverse construct (Sig-2C; FIG. 5 right column) maintained the substrate specificity of the Δ5/Δ6 enzyme but fatty acid conversion was reduced by approximately 30%. Since the last tenth of the enzymes do not appear to contribute to substrate specificity, chimeric proteins with domain swapping from the "PVYG" amino acid location onward, representing approximately the last third of the enzyme, were constructed (Sig-3C; FIG. 5 left column, and Sig-4C; FIG. 5 right column). No change in substrate specificities was observed between the two chimeras but the enzyme activities of Sig-3C and 4C were reduced by approximately 30% and 45%, respectively, compared to wild-type (see also Table 1).

The regions from "LIPV" onward, representing approximately the last 40% of the coding regions, were exchanged in the corresponding chimeric constructs Sig-5C (SEQ ID NO: 10; FIG. 5 left column) and Sig-6C (SEQ ID NO: 2; FIG. 5 right column). The switch from Δ4 to Δ5/Δ6 sequence at "LIPV" caused Sig-5C to lose Δ4 activity but gain Δ6 activity, showing a conversion level of approximately 23% with ALA (Sig-5C; SEQ ID NO: 10; FIG. 5 left column; Table 1). Conversely, the reverse construct lost 46 activity but gained activity with DPA (Sig-6C; SEQ ID NO: 2; FIG. 5 right column; Table 1). Thus, the region responsible for substrate specificity appears to be located between the "LIPV" and "PVYG" regions (amino acid residues position: Δ4, 275-316; Δ5/Δ6, 273-314) of these enzymes, as shown in FIG. 3A.

To confirm that the residues between "LIPV" to "PVYG" alone were responsible for substrate specificity, a pair of chimeric genes (Sig-7C; SEQ ID NO: 12; FIG. 5 left column, and Sig-8C; SEQ ID NO: 4; FIG. 5 right column) substituting only this region were constructed by PCR.

The gene containing the Δ5/Δ6 desaturase sequence in this area and the Δ4 desaturase sequence throughout the rest of the construct desaturated only ALA (11.5±1.2%) while the reverse construct had activity only with DPA (3.8±0.2%), demonstrating that the region between amino acids "LIPV" and "PVYG" controls substrate specificity. This area includes part of the $3^{rd}$ and $4^{th}$ predicted transmembrane domains along with the linker region (FIG. 2).

To further dissect this region, chimeric genes were constructed that divided the region between "LIPV" and "PVYG" of the S. canaliculatus Δ4 and Δ5/Δ6 desaturase into 3 fractions (end of linker to $4^{th}$ transmembrane domain: "WAMT/WCLS" to "PVYG", linker region between $3^{rd}$ and $4^{th}$ transmembrane domain: "TMI/IMI" to "WAMT/WCLS" and $3^{rd}$ transmembrane domain to start of linker region: "LIPVF" to "TMI/IMI").

When expressed in yeast cells, Sig-9C, which is an S. canaliculatus Δ4 desaturase gene with the region encoding the amino acids from "WCLS" to "PVYG" substituted with the corresponding Δ5/Δ6 desaturase sequence (FIG. 5 left column), converted 4.0±0.5% of $DPA_{\omega3}$ to $DHA_{\omega3}$, while the reverse construct (Sig-10C; FIG. 5 right column) converted ALA to SDA at a level of 14.9±1.4%, indicating that the 4th transmembrane domain is not relevant in substrate specificity but has an effect on the catalytic activities of the enzymes.

Moreover, Sig-11C (FIG. 5 left column) and its reverse gene construct (Sig-12C; FIG. 5 right column) which have sequence exchanges between the linker region of $3^{rd}$ and 4th transmembrane domains (sequence from "TMI/IMI" to "WAMT/WCLS"), also retained their original substrate specificity although enzyme activity was reduced to about half of the respective wild-type genes (FIG. 5). These data suggest that the linker region between $3^{rd}$ and 4th transmembrane domain ("TMI/IMI" to "WAMT/WCLS") on the S. canaliculatus Δ4 and Δ5/Δ6 desaturases are not the critical regions for substrate specificity although sequence switching in these regions greatly reduces catalytic activities.

However, when the region between the $3^{rd}$ transmembrane domain and the start of linker region involving the sequence from "LIPV" to "IMI/TMI" (Sig-13C; SEQ ID NO: 14; FIG. 5 left column, and Sig-14C; SEQ ID NO: 6; FIG. 5 right column) were substituted, there was a shift in substrate specificity. The mutated S. canaliculatus Δ4 (Sig-13C; SEQ ID NO: 14; FIG. 5 left column) desaturates only ALA (13.1±1.8%) but no longer desaturates $DPA_{\omega3}$. Therefore this mutation allowed the gene to gain Δ5/Δ6 activity but completely abolished the Δ4 activity. In contrast, the reverse construct (Sig-14C; SEQ ID NO: 6; FIG. 5 right column) gained Δ4 activity as demonstrated by $DPA_{\omega3}$ desaturation (3.4±0.2%) but completely lost its original Δ5/Δ6 activity. Thus, a region that appears to be within the $3^{rd}$ transmembrane domain critically affects substrate specificity.

To examine whether the eight amino acids (S. canaliculatus Δ4 desaturase: LIPVFYNY-NIMMTMI; S.

canaliculatus Δ5/Δ6 desaturase: LIPVFFHYQLLKIMI) between the "LIPVF" to "TMI/IMI" region were all required for substrate specificity or if only specific amino acids were critical, the inventors made constructs with alterations in this region by dividing the 8 amino acid region into two portions. Altering the "IMMT" amino acid sequence of the S. canaliculatus Δ4 desaturase gene to "LLKI" (Sig-15C; FIG. 6 left column) did not alter the substrate specificity of the Δ4 desaturase gene, as it desaturated DPA$_{ω3}$(2.9±0.3%) to generate DHA$_{ω3}$ and had no activity on ALA. Similarly, the reverse gene construct with alteration of the S. canaliculatus Δ5/Δ6 desaturase (Sig-16C; FIG. 6 right column) from "LLKI" to "IMMT" (corresponding residues in S. canaliculatus Δ4 desaturase) did not affect substrate specificity (16.3±1.1%, ALA). However, substitution of the Δ4 desaturase amino acid sequence "YNYN" to the Δ5/Δ6 desaturase sequence "FHYQ" at the same location (Sig-17C; SEQ ID NO: 16; FIG. 6 left column; Table 1) changed the substrate specificity from DPA$_{ω3}$ to ALA (12.5±0.8%). Likewise, altering the S. canaliculatus Δ5/Δ6 desaturase sequence from "FHYQ" to the corresponding "YNYN" sequence (Sig-18C; SEQ ID NO: 8; FIG. 6 right column; Table 1) resulted in a loss of Δ5/Δ6 desaturase activity but a gain in Δ4 desaturase activity (0.5±0.1%, DPA$_{ω3}$). Thus, the four amino acids that regulate the substrate specificity of S. canaliculatus Δ4 and Δ5/Δ6 desaturases are "YNYN" and the corresponding sequence "FHYQ".

TABLE 1

Fatty acid desaturation by yeast expressing S. canaliculatus Δ 4-desaturase, Δ5/6-desaturase and chimera constructs.

| | Desaturation of substrates | | | | | |
|---|---|---|---|---|---|---|
| | DPA (mol %) | DHA (mol %) | Conversion % | ALA (mol %) | SDA (mol %) | Conversion % |
| Δ4 Desaturase | 5.20 ± 0.34 | 0.72 ± 0.01 | 12.12 | 12.01 ± 2.44 | 0 | 0 |
| Δ5/6 Desaturase | 6.88 ± 0.95 | 0 | 0 | 9.88 ± 1.13 | 2.94 ± 0.66 | 22.96 |
| Sig-3C | 7.81 ± 0.62 | 0.72 ± 0.08 | 8.48 | 14.49 ± 3.15 | 0 | 0 |
| Sig-4C | 8.07 ± 1.30 | 0 | 0 | 13.11 ± 0.77 | 1.87 ± 0.31 | 12.48 |
| Sig-5C | 8.45 ± 1.45 | 0 | 0 | 12.59 ± 1.26 | 3.81 ± 0.34 | 23.24 |
| Sig-6C | 6.97 ± 1.47 | 0.41 ± 0.06 | 5.49 | 12.19 ± 2.65 | 0 | 0 |
| Sig-17C | 6.56 ± 1.07 | 0 | 0 | 9.53 ± 0.65 | 1.37 ± 0.06 | 12.55 |
| Sig-18C | 7.97 ± 1.37 | 0.04 ± 0.00 | 0.50 | 11.36 ± 1.59 | 0 | 0 |

2.3 Substitution of Amino Acids within the Four Amino Acid Region Produces Enzymes with Both Δ4- and Δ6-Desaturase Activities After determining that this four amino acid region was responsible for substrate specificity, substitution of individual amino acids was performed (FIG. 7). An amino acid substitution at position 4 (FIG. 7) of the critical region showed no effect on substrate specificity in either the Δ4 (Sig-19C; FIG. 6 left column) or Δ5/Δ6 desaturases (Sig-20C; FIG. 6 right column). However, decreases in substrate conversion levels (10.0±0.4%, DPA$_{ω3}$ for Sig-19C and 15.6±0.9%, ALA for Sig-20C) were observed. When a single amino acid was substituted at position 2 (N to H or vice versa), the substrate specificity of the point-mutated Δ4 desaturase (Sig-21C; FIG. 6 left column) remained the same (DPA$_{ω3}$) although enzyme activity was reduced to 3.5±0.2%, which is about a 71% reduction in activity compared to wild-type. The Δ5/Δ6 desaturases with an amino acid substitution at position 2 in the critical region (Sig-22C; SEQ ID NO: 22; FIG. 6 right column) not only desaturated ALA (13.6±5.0%) but also produced DHA$_{ω3}$ at a low level (0.5±0.04%). The Sig-23C (Δ4 desaturase; SEQ ID NO: 18; FIG. 6 left column) and Sig-24C (Δ5/Δ6 desaturase; SEQ ID NO: 24; FIG. 6 right column) with amino acid substitutions in the corresponding residues at position 1 of the critical region were able to desaturate both DPA$_{ω3}$ and ALA. Since positions 1 and 2 seem to play a more important role in the substrate specificity, the inventors rationally engineered desaturases with two amino acid substitutions in this region (Sig-25C; SEQ ID NO: 20; FIG. 6 left column, and Sig-26C SEQ ID NO: 26; FIG. 6 right column). Interestingly, site-directed mutation of both of these amino acids concurrently generates enzymes with desaturation of DPA$_{ω3}$ and ALA (Sig-25C; SEQ ID NO: 20; FIG. 6 left column, and Sig-26C SEQ ID NO: 26; FIG. 6 right column). Further, mutations including the amino acids at position 1, 2 and 4 (Sig-17C; SEQ ID NO: 16; FIG. 6 left column, and Sig-18C; SEQ ID NO: 8; FIG. 6 right column) restored specificity, even though single mutations at the 4$^{th}$ position did not directly affect substrate specificity as demonstrated by yeast expression (Sig-19C; FIG. 6 left column, and Sig-20C; FIG. 6 right column). This suggests that some type of interaction between these three amino acids is required for the substrate specificity of the enzymes studied here.

2.4 Four Amino Acid Residues Determine the Substrate Chain-Length and Regioselectivity of Siganus canaliculatus Δ4 and Δ5/6 Desaturases The unusually high similarity in amino acid composition (83%) between S. canaliculatus Δ4 and Δ5/Δ6 desaturases gave the present inventors an advantage in locating individual regions or residues involved in substrate specificity and regioselectivity. They identified a discrete protein region containing just four amino acid residues ("YNYN", position 280-283 on S. canaliculatus Δ4 desaturase and the corresponding amino acids "FHYQ" at position 278-281 on the S. canaliculatus Δ5/Δ6 desaturase) which is responsible for both the substrate chain-length specificity and the regioselectivity of S. canaliculatus Δ4 and Δ5/Δ6 desaturases (FIG. 6). The absence of a crystal structure for any membrane bound desaturase made it difficult to structurally interpret the alteration in regioselectivity and substrate specificity observed here. However, the S. canaliculatus Δ4 and Δ5/Δ6 desaturases are membrane bound enzymes and, based on previous studies the histidine boxes, N- and C-termini of the enzymes have been predicted to be located on the cytoplasmic side of the membrane. Given these constraints, the membrane protein topology prediction software (TOPCONS; Bernsel et al., 2009) predicts each of these two S. canaliculatus desaturases have four transmembrane domains (amino acid residues 132-152, 159-179, 265-285, 303-323 for Δ4 desaturase and corresponding residues for Δ5/Δ6 desaturase) linked by two exoplasmic regions consisting of six and seventeen amino acids (FIG. 1). It is expected that these highly similar desaturases would share a common membrane topology and presumably a common structural folding.

The four critical amino acid residues influencing the substrate specificity and regioselectivity of the S. canaliculatus desaturases are predicted to be located in the third putative transmembrane domain (FIG. 2). This four amino acid residue block is at some distance from the histidine-rich active site, which suggests that no direct interaction between the mutated amino acid residues and the substrate is required for the observed alterations in regiospecificity and substrate specificity (Cahoon et al., 1997). However, these four amino acid residues may form part of a hydrophobic substrate binding pocket which places constraints on the chain length of the substrate. Influences due to modification of the hydrophobic substrate binding pocket were observed in lipoxygenases and soluble fatty acid desaturases (Cahoon et al., 1997; Borngraber et al., 1999) and the authors suggest that the size and geometry of this hydrophobic binding pocket are responsible for the substrate specificity and insertion of double bond position. The amino acid residues "YNYN" in the critical region of the S. canaliculatus Δ4 desaturase are somewhat less bulky than the respective "FHYQ" residues in S. canaliculatus Δ5/Δ6 desaturase, possibly allowing the hydrophobic substrate binding pocket to accommodate a larger substrate such as DPA$_{ω3}$ (22:5$_{ω3}$), whereas the presence of bulkier residues may put a greater constraint on the substrate binding pocket to favour the smaller substrate ALA (18:2). Alternatively, the presence of a histidine residue in proximity to aromatic amino acids may result in π-π stacking interactions between aromatic amino acids which could influence packing effects and thus affect the substrate selection (Liao et al., 2013).

The inventors have also generated novel desaturases with Δ4 and Δ6 activities (Sig-22C/SEQ ID NO: 22; Sig-23C/SEQ ID NO: 18; Sig-24C/SEQ ID NO: 24; Sig-25C/SEQ ID NO: 20; Sig-26C/SEQ ID NO: 26; FIG. 6) by altering only one or two amino acids at positions 1 and 2 of the critical region (FIG. 7). The dual enzyme activities of the mutants were unexpected, and mutating both residues increases enzyme activity by 2.4 to 3.3 fold compared to mutating only the amino acid residue at position 1. A single amino acid residue mutation at position 4 (FIG. 7), results in a lower catalytic ability in both Δ4 and Δ5/Δ6 desaturases but does not affect the substrate or double bond position specificities. However, when this mutation was combined with double amino acid mutations at positions 1 and 2 (FIG. 7), the Δ4 desaturase was converted to an enzyme with Δ5/Δ6 desaturase activity and substrate specificity, and vice versa. This indicates that the substrate specificity and regioselectivity of the S. canaliculatus desaturases cannot be confined to a single amino acid residue. In fact, some degree of interaction between all four amino acid residues (Δ4: "YNYN" and Δ5/Δ6: "FHYQ") appears to be responsible for the substrate specificity and regioselectivity of the enzymes. Interestingly, similar results were obtained by Yuan et al. (1995). A single amino acid change (T231 K) in a thioesterase by itself did not affect substrate specificity but when this mutation was added to an enzyme with two mutations (M197R/R199H) which possessed equal preference for 12:0 and 14:0, the triple mutant was active only on 14:0. Here, the single mutation at position 4 (FIG. 7) shows a non-additive combinatory effect on the double mutant at positions 1 and 2, which suggests that some type of interaction is occurring between these amino acids (Sandberg and Terwilliger, 1993; Yuan et al., 1995).

Example 3

Based on the results obtained in Example 2 and further sequence alignments and topology predictions, the corresponding amino acid regions controlling the substrate specificity could be identified, in Δ4, Δ5 and/or Δ6 desaturases of other organisms as well. By exchanging the corresponding amino acid regions regulating the substrate specificity, the substrate specificity can also be switched in said Δ4, Δ5 and/or Δ6 desaturases, indicating that the teaching from the S. canaliculatus Δ4 and Δ 5/6 desaturases can be readily transferred to other "front-end" desaturases. In particular, this is exemplified for the Δ6 desaturases of Ostreococcus tauri and Pythium irregulare and the delta-5 desaturase of Thraustochytrium sp., in the following. Accession numbers and/or sequence identity numbers of Δ4, Δ5 and/or Δ6 desaturases referred to in this Example have already been indicated in the description.

3.1 Ostreococcus tauri Δ6 Desaturase

The following data is based on the alignment of Δ4 desaturases (Euglena gracilis, Emiliana huxleyi, Pavlova lutheri, Pavlova salina, Siganus arctica, Siganus canaliculatus) with Δ6 desaturases (Ostreococcus lucimarinus, Ostreococcus tauri, Siganus canaliculatus).

3.1.1 In the O. tauri Δ6 desaturase, the amino acid residues (AA) "MFFL" (position 283-286) correspond to the four important amino acid residues identified in the studies presented in Example 2 (S. canaliculatus Δ4-desaturase: "YNYN" and Δ5/6-desaturase: "FHYQ")]. The amino acid residues at position 1, 2 and 4 were shown to have a significant influence on substrate specificity in S. canaliculatus. The O. lucimarinus Δ6 desaturase has the same amino acid residues at positions 1, 2 and 4 ("FWMFFLH") as the O. tauri Δ6-desaturase. The corresponding amino acid residues on the P. salina and P. lutheri Δ4-desaturase are "FKLLFLD".

If this important region from the O. tauri Δ6 desaturase is aligned with the P. salina and P. lutheri Δ4 desaturases, the differences in the amino acid residues are: O. tauri Δ6 desaturase, "FWMFFLH" and P. lutheri/P. salina Δ4 desaturase, "FKLLFLD". So performing amino acid residue substitutions based on these differences is feasible (Betts and Russell, 2003).

Hydrophobicity: The "W" and "F" amino acid residues in the O. tauri Δ6 desaturase are aromatic amino acids which are relatively non-polar and hydrophobic. Changing from "WMF" to "KLL" will reduce the hydrophobicity of the corresponding region. Similarly, from the study with the Siganus canaliculatus Δ4 desaturase and Δ5/6 desaturase presented in Example 2, the inventors knew that the Δ5/Δ6 desaturase contains more aromatic amino acid residues in the four amino acid region, and is thus more hydrophobic than the Δ4 desaturase.

All mutations based on the above are demonstrated below:

```
O. tauri Δ6 desaturase:
                                        SEQ ID NO: 71
281           FWMFFLH              287/

P. lutheri and P. salina Δ4 desaturase:
                                        SEQ ID NO: 72
256/259       FKLLFLD              262/265/

O. tauri Δ6 desaturase:
                                        SEQ ID NO: 73
278           VLLFWMFFLHPSKALK     293/

Mutation 1:
                                        SEQ ID NO: 74
278           VLLFKLLFLHPSKALK     293/

Mutation 2:
                                        SEQ ID NO: 75
278           VLLFKLLFLDPSKALK     293/

Mutation 3:
                                        SEQ ID NO: 76
278           VLLFKLFFLHPSKALK     293/
```

-continued

Mutation 4:
SEQ ID NO: 77
278    VLLFKLFFLDPSKALK    293/

Mutation 5:
SEQ ID NO: 78
278    VLLFKMLFLHPSKALK    293/

Mutation 6:
SEQ ID NO: 79
278    VLLFKMLFLDPSKALK    293/

Mutation 7:
SEQ ID NO: 80
278    VLLFWLFFLHPSKALK    293/

Mutation 8:
SEQ ID NO: 81
278    VLLFWLFFLDPSKALK    293/

Mutation 9:
SEQ ID NO: 82
278    VLLFWMLFLHPSKALK    293/

Mutation 10:
SEQ ID NO: 83
278    VLLFWMLFLDPSKALK    293/

Mutation 11:
SEQ ID NO: 84
278    VLLFWLLFLHPSKALK    293/

Mutation 12:
SEQ ID NO: 85
278    VLLFWLLFLDPSKALK    293/

Mutation 13:
SEQ ID NO: 86
278    VLLFKMFFLHPSKALK    293/

Mutation 14:
SEQ ID NO: 87
278    VLLFWMFFLDPSKALK    293/

3.1.2 The 3$^{rd}$ transmembrane (TM) domain of *S. canaliculatus* Δ4 and Δ5/Δ6 desaturases contains the region of interest, as demonstrated in Example 2. A topology prediction (TOPCONS) was used to identify the 3$^{rd}$ transmembrane domain of the *O. tauri* Δ6 desaturase from positions 300-320. Alignment of this region with *P. salina, S. artica* or *P. lutheri* Δ4 desaturases identifies a region of homology which can be used to replace the *O. tauri* 3$^{rd}$ transmembrane region; i.e. the bold *O. tauri* Δ6 desaturase region can be replaced by the bold region of Δ4 desaturase genes which could result in a change of the substrate specificity of the Δ6 desaturase to the substrate specificity of a Δ4 desaturase. Tequence identity numbers only refer to sections in bold lettering.

*O. tauri* Δ6 desaturase:
SEQ ID NO: 88
290    KALKGGKYEELVWMLAAHVIRTWTIKAVTGFTAMQSYGLFL    330/

*P. lutheri* Δ4 desaturase:
SEQ ID NO: 89
274    EKISPLARALFAPAVACKLGFWARFVALPLWLQPTVHTALCIC    316/

*S. artica* Δ4 desaturase:
SEQ ID NO: 90
277    EKLPESYR-KERNIAIGLRVFFFIRKFVVPFALHFSWYTLLCTY    319/

*P. salina* Δ4 desaturase:
SEQ ID NO: 91
280    SKLAGYLFMPSLLLKLTFWARFVALPLYLAPSVHTAVCIA    319/

3.1.3 The 3$^{rd}$ transmembrane domain of *O. tauri* Δ6 desaturase (position 300-320, in bold) can be replaced with the corresponding Δ4 desaturase 3$^{rd}$ transmembrane domain (in bold) based on TOPCONS topology prediction software.

*O. tauri* Δ6 desaturase: (sequence identity numbers only refer to sections in bold lettering)
SEQ ID NO: 88
290    KALKGGKYEELVWMLAAHVIRTWTIKAVTGFTAMQSYGLFL    330/ a) Substitute with *P. lutheri* Δ4 desaturase (281-301):
SEQ ID NO: 92
RALFAPAVACKLGFWARFVAL/ b) Substitute with *P. salina* Δ4 desaturase (291-311):
SEQ ID NO: 93
LLLKLTFWARFVALPLYLAPS/ c) Substitute with *S. arctica* Δ4 desaturase (293-313):
SEQ ID NO: 94
LRVFFFIRKFVVPFALHFSWY/

3.1.4 Substitute the entire corresponding "LI PV" to "PVYG" region on *O. tauri* Δ6 desaturase (position 278-321) with the respective Δ4 desaturase domain, based on sequences alignments. This region was shown to be important in the *S. canaliculatus* desaturase sequences, as shown in Example 2.

*O. tauri* Δ6 desaturase (position 278-321):
SEQ ID NO: 95
VLLFWMFFLHPSKALKGGKYEELVWMLAAHVIRTWTIKAVTGFT/

Substitute with:

a) *P. lutheri* Δ4 desaturase (265-307):
SEQ ID NO: 96
ELLAWRWEGEKISPLARALFAPAVACKLGFWARFVALPLWLQP/ b) *P. salina* Δ4 desaturase (268-310):
SEQ ID NO: 97
ELVMWRWEGEPISKLAGYLFMPSLLLKLTFWARFVALPLYLAP/ c) *S. artica* Δ4 desaturase (268-310):
SEQ ID NO: 98
DLIEMKYKGEKLPESYRKERNIAIGLRVFFFIRKFVVPFALHF/

3.1.5 The four amino acid region of the *S. canaliculatus* Δ4 and Δ5/Δ6 desaturases identified in Example 2 are located at the end of 3$^{rd}$ transmembrane domain close to the exoplasmic face of the membrane (positions 280-283 and 278-281, respectively). Thus, based on topology predictions, the comparable amino acid residues on the 3$^{rd}$ transmembrane domain of the *O. tauri* Δ6 desaturase are "KAVT" (position 315-318). Substituting said amino acid residues with the Δ4 desaturase amino acid residues from the same topological location can influence the substrate specificity and regioselectivity.

*O. tauri* (position 315-318) "KAVT"/SEQ ID NO: 99 replace with:
*P. lutheri* Δ4 desaturase (position 296-299): "ARFV"/SEQ ID NO: 100
or *P. salina* Δ4 desaturase (position 306-309): "LYLA"/SEQ ID NO: 101
or *S. artica* Δ4 desaturase (position 308-311): "LHFS"/SEQ ID NO: 102

3.2 *Thraustochytrium* sp. Δ5 Desaturase

The following data is based on the sequence alignment of the Δ4 desaturase (*Pavlova lutheri, Pavlova saline, Siganus artica, Thraustochytrium* sp., *Siganus canaliculatus*) with the Δ5 desaturase (*Thraustochytrium* sp., *Pavlova saline, Siganus canaliculatus*).

3.2.1 In the *Thraustochytrium* sp. Δ5 desaturase, the amino acid residues corresponding to the region identified in *S. canaliculatus* are "TLYL" (position 270-273), with positions 2, 3, and 4 conserved with the *P. saline* Δ5 desaturase. For conversion to a Δ4 desaturase, substitute with the bold region (sequence identity numbers only refer to sections in bold lettering):

```
Thraustochytrium sp. Δ5 desaturase:
                                   SEQ ID NO: 103
265       IGLGWTLYLHPR             276/

P. lutheri Δ4 desaturase:
                                   SEQ ID NO: 104
265       ELLAWRWEGEKI             276/

P. salina Δ4 desaturase:
                                   SEQ ID NO: 105
268       ELVMWRWEGEPI             279/

S. artica Δ4 desaturase:
                                   SEQ ID NO: 106
268       DLIEMKYKGEKL             279/
``` a) Substitute one amino acid residue at a time. Bold: substituted amino acid residue/SEQ ID NO.

Replace with "RWEG" (corresponding region on *P. saline* and *P. lutheri* Δ4 desaturase)

```
Mutation 1: Thraustochytrium sp. Δ5 desaturase:
                                   SEQ ID NO: 107
265       IGLGWRLYLHPR             276/

Mutation 2: Thraustochytrium sp. Δ5 desaturase:
                                   SEQ ID NO: 108
265       IGLGWRWYLHPR             276/

Mutation 3: Thraustochytrium sp. Δ5 desaturase:
                                   SEQ ID NO: 109
265       IGLGWRWELHPR             276/

Mutation 4: Thraustochytrium sp. Δ5 desaturase:
                                   SEQ ID NO: 110
265       IGLGWRWYGHPR             276/

Mutation 5: Thraustochytrium sp. Δ5 desaturase:
                                   SEQ ID NO: 111
265       IGLGWRLYGHPR             276/

Mutation 6: Thraustochytrium sp. Δ5 desaturase:
                                   SEQ ID NO: 112
265       IGLGWRLELHPR             276/
``` b) Replace with "KYKG" (corresponding region on *S. artica* Δ4 desaturase). Bold: substituted amino acid residue/SEQ ID NO.

```
Thraustochytrium sp. Δ5 desaturase:
                                   SEQ ID NO: 113
265       IGLGWTLYLHPR             276/

Mutation 1:
                                   SEQ ID NO: 114
265       IGLGWKLYLHPR             276/

Mutation 2:
                                   SEQ ID NO: 115
265       IGLGWKYYLHPR             276/

Mutation 3:
                                   SEQ ID NO: 116
265       IGLGWKYKLHPR             276/

Mutation 4:
                                   SEQ ID NO: 117
265       IGLGWKLKLHPR             276/

Mutation 5:
                                   SEQ ID NO: 118
265       IGLGWKLYGHPR             276/

Mutation 6:
                                   SEQ ID NO: 119
265       IGLGWKLKGHPR             276/

Mutation 7:
                                   SEQ ID NO: 120
265       IGLGWTYYLHPR             276/

Mutation 8:
                                   SEQ ID NO: 121
265       IGLGWTYKLHPR             276/

Mutation 9:
                                   SEQ ID NO: 122
265       IGLGWTYKGHPR             276/

Mutation 10:
                                   SEQ ID NO: 123
265       IGLGWTLKLHPR             276/

Mutation 11:
                                   SEQ ID NO: 124
265       IGLGWTLKGHPR             276/
```

3.2.2 Based on sequence alignments, there are five amino acid residues near the important region that are conserved between *P. lutheri* and *P. saline* Δ4 desaturases. Replacing these 5 amino acid residues can result in a change in desaturase specificity (sequence identity numbers only refer to sections in bold lettering):

```
Thraustochytrium sp. Δ5 desaturase:
                                   SEQ ID NO: 125
265       IGLGWTLYLHPR             276/

P. lutheri 44 desaturase:
                                   SEQ ID NO: 126
265       ELLAWRWEGEKI             276/

P. salina 44 desaturase:
                                   SEQ ID NO: 127
268       ELVMWRWEGEPI             279/

After substitution, Thraustochytrium sp. Δ5
desaturase:
                                   SEQ ID NO: 128
265       IGLGWRWEGEPR             276/
```

3.2.3 Based on sequence alignments, the region corresponding from "LIPV" to "PVYG" identified in Example 2 is from position 265-307, in the amino acid sequence of the *Thraustochytrium* sp. Δ5 desaturase. Substitution of amino acid residues from the *P. lutheri* Δ4 desaturase is shown below.

```
Thraustochytrium sp. Δ5 desaturase:
                                              SEQ ID NO: 129
265   IGLGWTLYLHPRYMLRTKRHMEFVWIFARYIGWFSLMGALGYS  307/

P. lutheri Δ4 desaturase:
                                              SEQ ID NO: 130
265   ELLAWRWEGEKISPLARALFAPAVACKLGFWARFVALPLWLQP  307/
```

3.2.4 Based on protein topology prediction software (TOPCONS), the *Thraustochytrium* sp. Δ5 desaturase has four transmembrane domains and two hydrophobic stretches. The 3$^{rd}$ transmembrane domain of *Thraustochytrium* sp. Δ5 desaturase is located from position 287-307. Substitution of the 3$^{rd}$ transmembrane domain with the corresponding domain based on homology is shown below:

```
Thraustochytrium sp. Δ5 desaturase, 3rd
transmembrane domain:
                              SEQ ID NO: 131
287      FVWIFARYIGWFSLMGALGYS    307/
```

Replace with:

```
P. lutheri Δ4 desaturase:
                              SEQ ID NO: 132
287         AVACKLGFWARFVALPLWLQP  307/
or
P. salina Δ4 desaturase:
                              SEQ ID NO: 133
290         SLLLKLTFWARFVALPLYLAP  310/
or
S. artica Δ4 desaturase:
                              SEQ ID NO: 134
290         AIGLRVFFFIRKFVVPFALHF  310/
```

Based strictly on topology predictions (TOPCONS), the inventors could substitute the 3rd transmembrane domain of the *Thraustochytrium* sp. Δ5 desaturase with the 3rd transmembrane domain of other Δ4 desaturases:

```
Thraustochytrium sp. Δ5 desaturase, 3rd
transmembrane domain:
                              SEQ ID NO: 131
287      FVWIFARYIGWFSLMGALGYS    307/
```

Replace with:

```
P. lutheri Δ4 desaturase, 3rd TM:
                              SEQ ID NO: 135
281      RALFAPAVACKLGFWARFVAL    301/
or
P. Salina Δ4 desaturase, 3rd TM:
                              SEQ ID NO: 136
291      LLLKLTFWARFVALPLYLAPS    311/
or
S. arctica Δ4 desaturase, 3rd TM:
                              SEQ ID NO: 137
293      LRVFFFIRKFVVPFALHFSWY    313/
```

3.2.5 Based on the studies shown in Example 2, the four amino acid residues which influence the substrate specificity are located at the end of the 3rd transmembrane domain close to the exoplasmic face. The four amino acid residues are located in the last 6 amino acid residues in the 3$^{rd}$ transmembrane domain of *S. canaliculatus* Δ4 and Δ5/Δ6 desaturases. In *Thraustochytrium* sp. Δ5 desaturase, position 302-305 represents the same location based on topology prediction (starts at last 6 amino acid residues in the 3rd transmembrane domain).

a) Substitution of amino acid residues corresponding to *Thraustochytrium* sp. Δ5 desaturase position 302-305 ("GALG"/SEQ ID NO: 138) based on sequence alignment as follows:

```
i) P. lutheri Δ4 desaturase:
                              SEQ ID NO: 139
   302-305 "PLWL"/ ii) P. salina Δ4 desaturase:
                              SEQ ID NO: 140
   305-308 "PLYL"/ iii) S. artica Δ4 desaturase:
                              SEQ ID NO: 141
   305-308 "PFAL"/
``` b) Substitution of amino acid residues corresponding to *Thraustochytrium* sp. Δ5 desaturase 302-305 ("GALG"/SEQ ID NO: 138) based on topology prediction, as follows:

```
i) P. lutheri Δ4 desaturase:
                              SEQ ID NO: 142
   296-299 "ARFV"/ ii) P. salina Δ4 desaturase:
                              SEQ ID NO: 143
   306-309 "LYLA"/ iii) S. artica Δ4 desaturase:
                              SEQ ID NO: 144
   308-311 "LHFS"/
```

3.3 *Pythium irregulare* Δ6 Desaturase

The following data is based on sequence alignments of the *Pythium irregulare* Δ6 desaturase with other Δ6 desaturases (*Siganus canaliculatus.*) *Primula farinosa*) and Δ4 desaturases (*Emiliana huxleyi, Monosiga brevicollis, Pavlova lutheri, Pavlova salina, Siganus artica, Thalassiosira pseudonana, Siganus canaliculatus, Thraustochytrium* sp.).

3.3.1 The amino acid residues corresponding to the region identified in *S. canaliculatus* in Example 2, in the *P. irregulare* Δ6 desaturase are "AQSF" (position 284-287). These residues are conserved between several Δ6 desaturases (*P. irregulare, P. farinosa*). Based on sequence alignment, these amino acid residues could be substituted with amino acid residues from Δ4 desaturases (sequence identity numbers only refer to sections in bold lettering):

```
P. irregulare Δ6 desaturase:
                              SEQ ID NO: 145
   280      LSWLAQSFFYV          290/
```

Replace with amino acid residues from:

```
P. salina Δ4 desaturase:
                                SEQ ID NO: 146
259        FKLLFLDISEL          269/

P. lutheri Δ4 desaturase:
                                SEQ ID NO: 147
256        FKLLFLDALEL          266/

S. artica Δ4 desaturase:
                                SEQ ID NO: 148
259        FQWVFLGLHDL          269/

M. brevicollis Δ4 desaturase:
                                SEQ ID NO: 149
241        AKVIIGDWYNL          251/

E. huxleyi Δ4 desaturase:
                                SEQ ID NO: 150
234        FVFAFTIRKYA          244/

T. pseudonana Δ4 desaturase:
                                SEQ ID NO: 151
315        LAKVFQQDFEV          325/

Thraustochytrium sp. Δ4 desaturase:
                                SEQ ID NO: 152
290        INKVVTQDVGV          300/
```

Substitution of single amino acid residues could also be performed as described above.

3.3.2 Based on topology prediction (TOPCONS), the P. irregulare Δ6 desaturase contains four transmembrane domains and two hydrophobic stretches; the 3rd transmembrane domain is located between position 310-330. From Example 2 it is known, that the amino acid residues of interest are in the third transmembrane domain. Based on sequence alignment, the inventors could substitute the 3rd transmembrane domain of the P. irregulare Δ6 desaturase with the corresponding region from Δ4 desaturases.

```
3rd TM P. irregulare Δ6 desaturase:
                                SEQ ID NO: 153
310        AGLIVHYIWQLAIPYFCNMSL    330/
```

Replace with:

```
P. lutheri Δ4 desaturase:
                                SEQ ID NO: 154
288        VACKLGFWARFVALPLWLQPT    308/
or P. salina Δ4 desaturase:
                                SEQ ID NO: 155
291        LLLKLTFWARFVALPLYLAPS    311/
or S. artica Δ4 desaturase:
                                SEQ ID NO: 156
291        IGLRVFFFIRKFVVPFALHFS    311/
or Thraustochytrium sp. Δ4 desaturase:
                                SEQ ID NO: 157
325        WIMKALTVLYMVALPCYMQGP    345/
or M. brevicollis Δ4 desaturase:
                                SEQ ID NO: 158
274        VLARICWLVRLVAIPVYLHGW    294/
```

3.3.3 Substitute the 3rd transmembrane domain of the P. irregulare Δ6 desaturase with the 3rd transmembrane domain of other Δ4 desaturase based on topology predictions:

```
3rd TM P. irregulare Δ6 desaturase:
                                SEQ ID NO: 153
310        AGLIVHYIWQLAIPYFCNMSL    330/
```

Replace with:

```
P. lutheri Δ4 desaturase, 3rd TM:
                                SEQ ID NO: 159
281        RALFAPAVACKLGFWARFVAL    301/
or P. salina Δ4 desaturase, 3rd TM:
                                SEQ ID NO: 160
291        LLLKLTFWARFVALPLYLAPS    311/
or S. arctica Δ4 desaturase, 3rd TM:
                                SEQ ID NO: 161
293        LRVFFFIRKFVVPFALHFSWY    313/
```

3.3.4 Based on the studies shown in Example 2, the four amino acid residues influencing the substrate specificity are located at the end of 3$^{rd}$ transmembrane domain close to the exoplasmic face of the membrane. In the P. irregulare Δ6 desaturase, position 325-328 ("FCNM") represents the same location, based on topology predictions. This region can be replaced as outlined below:

a) Substitute with amino acid residues corresponding to P. irregulare Δ6 desaturase position 325-328 ("FCNM"/SEQ ID NO: 162), based on sequence alignment:

```
i) P. lutheri Δ4 desaturase:
                                SEQ ID NO: 163
303-306 "LWLQ"/ ii) P. salina Δ4 desaturase:
                                SEQ ID NO: 164
306-309 "LYLA"/ iii) S. artica Δ4 desaturase:
                                SEQ ID NO: 165
306-309 "FALH"/ iv) Thraustochytrium sp. Δ4 desaturase:
                                SEQ ID NO: 166
340-343 "CYMQ"/
``` b) Substitute with amino acid residues corresponding to P. irregulare Δ6 desaturase position 325-328 ("FCNM"/SEQ ID NO: 162), based on topology prediction:

```
i) P. lutheri Δ4 desaturase:
                                SEQ ID NO: 167
296-299 "ARFV"/ ii) P. salina Δ4 desaturase:
                                SEQ ID NO: 168
306-309 "LYLA"/ iii) S. artica Δ4 desaturase:
                                SEQ ID NO: 169
308-311 "LHFS"/ iv) Thraustochytrium sp. Δ4 desaturase:
                                SEQ ID NO: 170
337-340 "ALPC"/
```

REFERENCES

1. Ahmann, K., Heilmann, M., and Feussner, I. (2011) Identification of a Δ4-desaturase from the microalga Ostreococcus lucimarinus, Eur. J. Lipid Sci. Technol. 113, 832-840.

2. Bernsel, A., Viklund, H., Hennerdal, A., and Elofsson, A. (2009) TOPCONS: consensus prediction of membrane protein topology, *Nucleic Acids Res.* 37 (Web Server Issue), W465-468.
3. Bowler, C., Allen, A. E., Badger, J. H., and et al. (2008) The *Phaeodactylum* genome reveals the evolutionary history of diatom genomes, *Nature* 456, 239-244.
4. Broadwater, J. A., Whittle, E., and Shanklin, J. (2002) Desaturation and hydroxylation. Residues 148 and 324 of *Arabidopsis* FAD2, in addition to substrate chain length, exert a major influence in partitioning of catalytic specificity, *J. Biol. Chem.* 277, 15613-15620.
5. Broun, P., Shanklin, J., Whittle, E., and Somerville, C. (1998) Catalytic plasticity of fatty acid modification enzymes underlying chemical diversity of plant lipids, *Science* 282, 1315-1317.
6. Borngräber, S., Browner, M., Gillmor, S., Gerth, C., Anton, M., Fletterick, R., and Kuhn, H. (1999) Shape and specificity in mammalian 15-lipoxygenase active site, *J. Biol Chem.* 274, 37345-37350.
7. Cahoon, E. B., Lindqvist, Y., Schneider, G., and Shanklin, J. (1997) Redesign of soluble fatty acid desaturases from plants for altered substrate specificity and double bond position, *Proc. Natl. Acad. Sci. U.S.A.* 94, 4872-4877.
8. Cahoon, E. B., Shah, S., Shanklin, J., and Browse, J. (1998) A determinant of substrate specificity predicted from the acyl-acyl carrier protein desaturase of developing Cat's Claw seed, *Plant Physiol.* 117, 593-598.
9. Crawford, M. A. (2000) Placental delivery of arachidonic and docosahexaenoic acids: implications for the lipid nutrition of preterm infants, *Am. J. Clin. Nutr.* 71, 275-284.
10. Domergue, F., Lerchl, J., Zähringer, U., and Heinz, E. (2002) Cloning and functional characterization of *Phaeodactylum tricornutum* front-end desaturases involved in eicosapentaenoic acid biosynthesis, *Eur. J. Biochem.* 269, 4105-4113.
11. Garcia-Maroto, F., Garrido-Cardenas, J. A., Rodriguez-Ruiz, J., Vilches-Ferron, M., Adam, A. C., Polaina, J., Alonso, D. L. (2002) Cloning and molecular characterization of the delta6-desaturase from two echium plant species: production of GLA by heterologous expression in yeast and tobacco, *Lipids* 37, 417-426.
12. Hastings, N., Agaba, M., Tocher, D. R., Leaver, M. J., Dick, J. R., Sargent, J. R., and Teale, A. J. (2001) A vertebrate fatty acid desaturase with Δ5 and Δ6 activities, *Proc. Natl. Acad. Sci. U.S.A.* 98, 14304-14309.
13. Hastings, N., Agaba, M. K., Tocher, D. R., Zheng, X., Dickson, C. A., Dick, J. R., and Teale, A. J. (2005) Molecular cloning and functional characterization of fatty acyl desaturase and elongase cDNAs involved in the production of eicosapentaenoic and docosahexaenoic acids from α-linolenic acid in Atlantic salmon (Salmo Salar), *Mar. Biotechnol.* 6, 463-474.
14. Li, Y., Hu, C., Zheng, Y., Xia, X., Xu, W., Wang, S., Chen, W., Sun, Z., and Huang, J. (2008) The effects of dietary fatty acids on liver fatty acid composition and Δ6-desaturase expression differ with ambient salinities in *S. canaliculatus*, *Comp. Biochem. Physiol., Part B: Biochem. Mol.* 151, 183-190.
15. Li, Y., Monroig, O., Zhang, L., Wang, S., Zheng, X., Dick, J. R., You, C., and Tocher, D. R. (2010) Vertebrate fatty acyl desaturase with Δ4 activity, *Proc. Natl. Acad. Sci. U.S.A.* 107, 16840-16845.
16. Liao, S.-M., Du, Q.-S., Meng, J.-Z., Pang, Z.-W., and Huang, R.-B. (2013) The multiple roles of histidine in protein interactions, *Chem. Cent. J.* 7, 44.
17. Libisch, B., Michaelson, L. V., Lewis, M. J., Shewry, P. R., and Napier, J. A. (2000) Chimeras of Δ6-fatty acid and Δ8-sphingolipid desaturases, *Biochem. Biophys. Res. Commun.* 279, 779-785.
18. Los, D. A., and Murata, N. (1998) Structure and expression of fatty acid desaturases, Biochim. Biophys. Acta. 1394, 3-15.
19. Meesapyodsuk, D., Reed, D. W., Covello, P. S., and Qiu, X. (2007) Primary structure, regioselectivity, and evolution of the membrane-bound fatty acid desaturases of *Claviceps purpurea*, *J. Biol. Chem.* 282, 20191-20199.
20. Meesapyodsuk, D., and Qiu, X. (2012) The front-end desaturase: structure, function, evolution and biotechnological use. Lipids 47, 227-237.
21. Meyer, A., Cirpus, P., Ott, C., Schleker, R., Zahringer, U., and Heinz, E. (2003) Biosynthesis of docosahexaenoic acid in *Euglena gracilis*: biochemical and molecular evidence for the involvement of a Δ4-fatty acyl group desaturase, *Biochemistry* 42, 9779-9788.
22. Michell, A. G., and Martin, C. E. (1995) A novel cytochrome $b_5$-like domain is linked to the carboxyl terminus of the *Saccharomyces cerevisiae* Δ9-fatty acid desaturase, *J. Biol. Chem.* 270, 29766-29772.
23. Napier, J. A., Michaelson, L. V., and Sayanova, 0. (2003) The role of cytochrome $b_5$ fusion desaturases in the synthesis of polyunsaturated fatty acids, *Prostaglandins Leukot Essent Fatty Acids* 68, 135-143.
24. Napier, J. A., and Sayanova, O. (2005) The production of very-long-chain PUFA biosynthesis in transgenic plants: towards a sustainable source of fish oils, *Proc. Nutr. Soc.* 64, 387-393.
25. Pereira, S. L., Leonard, A. E., and Mukerji, P. (2003) Recent advances in the study of fatty acid desaturases from animals and lower eukaryotes, *Prostaglandins Leukot Essent Fatty Acids* 68, 97-106.
26. Piispanen, R., Saranpaa, P. (2002) Neutral lipids and phospholipids in Scots pine (*Pinus sylvestris*) sapwood and heartwood, *Tree Physiol* 22, 661-666.
27. Pollak, D. W., Bostick, M. W., Yoon, H., Wang, J., Hollerbach, D. H., He, H., Damude, H. G., Zhang, H., Yadav, N. S., Hong, S.-P., Sharpe, P., Xue, Z., and Zhu, Q. (2012) Isolation of a Δ5 desaturase gene from *Euglena gracilis* and functional dissection of its HPGG and HDASH motifs, *Lipids* 47, 913-926.
28. Qiu, X., Hong, H., and MacKenzie, S. L. (2001) Identification of a Δ4 fatty acid desaturase from *Thraustochytrium* sp. involved in the biosynthesis of docosahexanoic acid by heterologous expression in *Saccharomyces cerevisiae* and *Brassica juncea*, *J. Biol. Chem.* 276, 31561-31566.
29. Rapoport, S. I. (2008) Arachidonic acid and the brain, *J. Nutr.* 138, 2515-2520.
30. Reddy, A. S., Nuccio, M. L., Gross, L. M., and Thomas, T. L. (1993) Isolation of a Δ6-desaturase gene from the cyanobacterium *Synechocystis* sp. strain PCC 6803 by gain-of-function expression in *Anabaena* sp. strain PCC 7120, *Plant Mol. Biol.* 27, 293-300.
31. Sandberg, W. S. and Terwilliger, T. C. (1993) Engineering multiple properties of a protein by combinatorial mutagenesis, *Proc. Natl. Acad. Sci. U.S.A.* 90, 8367-8371.
32. Sayanova, O., Smith, M. A., Lapinskas, P., Stobart, A. K., Dobson, G., Christie, W. W., Shewry, P. R., and Napier, J. A. (1997) Expression of a borage desaturase cDNA containing an N-terminal cytochrome $b_5$ domain results in the accumulation of high levels of Δ6-desaturated fatty acids in transgenic tobacco, *Proc. Natl. Acad. Sci. U.S.A.* 94, 4211-4216.

33. Sayanova, O., Shewry, P. R., and Napier, J. A. (1999) Histidine-41 of the cytochrome $b_5$ domain of the borage Δ6 fatty acid desaturase is essential for enzyme activity, *Plant Physiol.* 121, 641-646.
34. Sayanova, O., Beaudoin, F., Libisch, B., Castel, A., Shewry, P. R., and Napier, J. A. (2001) Mutagenesis and heterologous expression in yeast of a plant Δ6-fatty acid desaturase, *J. Exp. Bot.* 52, 1581-1585.
35. Sayanova, O., Haslam, R., Qi, B., Lazarus, C. M., Napier, J. A. (2006) The alternative pathway C20 Delta8-desaturase from the non-photosynthetic organism *Acanthamoeba castellanii* is an atypical cytochrome $b_5$-fusion desaturase, *FEBS Lett* 580, 1946-1952.
36. Schenkman, J. B., and Jansson, I. (2003) The many roles of cytochrome $b_5$, *Pharmacol Ther.* 97, 129-152.
37. Shanklin, J., Whittle, E., and Fox, B. G. (1994) Eight histidine residues are catalytically essential in a membrane-associated iron enzyme, stearoyl-CoA desaturase, and are conserved in alkane hydroxylase and xylene monooxygenase, *Biochemistry* 33, 12787-12794.
38. Shanklin, J., Guy, J. E., Mishra, G., and Lindqvist, Y. (2009) Desaturases: emerging models for understanding functional diversification of di-iron-containing enzymes, *J. Biol. Chem.* 284, 18559-18563.
39. Sperling, P., and Heinz, E. (2001) Desaturases fused to their electron donor. *Eur. J. Lipid Sci. Technol.* 103, 158-180.
40. Sprecher, H., Luthria, D. L., Mohammed, B. S., and Baykousheva, S. P. (1995) Reevaluation of the pathways for the biosynthesis of polyunsaturated fatty acids, *J. Lipid Res.* 36, 2471-2477.
41. Sprecher, H. (2000) Metabolism of highly unsaturated n-3 and n-6 fatty acids, *Biochim. Biopys. Acta* 1486, 219-231.
42. Thies, F., Garry, J. M. C., Yaqoob, P., Rerkasem, K., Williams, J., Shearman, C. P., Gallagher, P. J., Calder, P. C., and Grimble, R. F. (2003) Association of n-3 polyunsaturated fatty acids with stability of atherosclerotic plaques: a randomised controlled trial. *Lancet* 361, 477-485.
43. Tocher, D. R., and Ghioni, C. (1999) Fatty acid metabolism in marine fish: low activity of fatty acyl Δ5 desaturation in gilthead sea bream (*Sparus aurata*) cells, *Lipids,* 34, 433-440.
44. Tocher, D. R. (2010) Fatty acid requirements in ontogeny of marine and freshwater fish, *Aquacult. Res.* 41, 717-732.
45. Tonon, T., Harvey, D., Larson, T. R., and Graham, I. A. (2003) Identification of a very long chain polyunsaturated fatty acid Δ4-desaturase from the microalga *Pavlova lutheri, FEBS Lett* 553, 440-444.
46. Tripodi, K. E. J., Buttigliero, L. V., Altabe, S. G., and Uttaro, A. D. (2006) Functional characterization of front-end desaturases from trypanosomatids depicts the first polyunsaturated fatty acid biosynthetic pathway from a parasitic protozoan, *FEBS J.* 273, 271-280.
47. Wallis, J. G., Browse, J. (1999) The Delta8-desaturase of *Euglena gracilis*: an alternate pathway for synthesis of 20-carbon polyunsaturated fatty acids, *Arch Biochem Biophys* 365, 307-316.
48. Venegas-Caleron, M., Beaudoin, F., Sayanova, O., Napier, J. A. (2007) Co-transcribed genes for long chain polyunsaturated fatty acid biosynthesis in the protozoon *Perkinsus marinus* include a plant-like FAE1 3-ketoacyl coenzyme A synthase, *J Biol Chem* 282, 2996-3003.
49. Weitz, D., Weintraub, H., Fisher, E., and Schwartzbard, A. Z. (2010) Fish oil for the treatment of cardiovascular disease, *Cardiol. Rev.* 18, 258-263.
50. Yuan, L., Voelker, T. A., and Hawkins, D. J. (1995) Modification of the substrate specificity of an acyl-acyl carrier protein thioesterase by protein engineering, *Proc. Natl. Acad. Sci. U.S.A.* 92, 10639-10643.
51. Zheng, X., Seiliez, I., Tocher, D. R., Panserat, S., Dickson, C. A., Bergot, P., and Teale, A. J. (2004). Characterization and comparison of fatty acyl Δ6 desaturase cDNAs from freshwater and marine teleost fish species. Comp. Biochem. Physiol. B 139, 269-279.
52. Zheng, X., Tocher, D. R., Dickson, C. A., Bell, J. G., and Teale, A. J. (2005) Highly unsaturated fatty acid synthesis in vertebrates: new insights with the cloning and characterization of a Δ6 desaturase of Atlantic salmon, *Lipids* 40, 13-24
53. Zhou, X.-R., Robert, S. S., Petrie, J. R., Frampton, D. M. F., Mansour, M. P., Blackburn, S. I., Nichols, P. D., Green, A. G., and Singh, S. P. (2007) Isolation and characterization of genes from the marine microalga *Pavlova saline* encoding three front-end desaturases involved in docosahexaenoic acid biosynthesis, *Phytochemistry* 68, 785-796.
54. Betts M J, Russell R B (2003) Amino acid properties and consequences of substitutions. In Barnes M R, Gray I C, eds. Bioinformatics for Geneticists. John Wiley and Sons Ltd. p. 289-316.

The invention claimed is:

1. A method for the conversion of the substrate specificity of a front-end Δ4 desaturase to the substrate specificity of a front-end Δ5 and/or Δ6 desaturase, the method comprising:
   a) identifying regions and/or amino acid residues which control the substrate specificity of
      (i) the front-end Δ4 desaturase and (ii) the front-end Δ5 and/or Δ6 desaturase; and
   b) replacing in the amino acid sequence of the front-end Δ4 desaturase referred to in step a), the regions and/or amino acid residues which control the substrate specificity of the front-end Δ4 desaturase, by the corresponding regions and/or amino acid residues which control the substrate specificity of the front-end Δ5 and/or Δ6 desaturase, thereby converting the substrate specificity of the front-end Δ4 desaturase to the substrate specificity of the front-end Δ5 and/or Δ6 desaturase,
   wherein the regions and/or amino acid residues which control the substrate specificity of the Δ4, Δ5 and/or Δ6 desaturase are localized within a transmembrane domain, wherein the transmembrane domain is the third putative transmembrane domain.

2. The method of claim 1, wherein the Δ4, Δ5 and/or Δ6 desaturase have substrate specificity for both ω3 and ω6 substrates.

3. The method of claim 1, wherein the substrate specificity of the Δ4 desaturase is for 22:5ω3 and 22:4ω6, the substrate specificity of the Δ5 desaturase is for 20:4ω3 and 20:3ω6, the substrate specificity of the Δ6 desaturase is for 18:3ω3 and 18:2ω6, and the substrate specificity of the Δ5 and/or Δ6 desaturase is for 20:4ω3, 20:3ω6, 18:3ω3 and 18:2ω6.

4. The method of claim 1, wherein the Δ4, Δ5 and/or Δ6 desaturase is selected from:

a) a Δ4 desaturase from *Monosiga brevicollis*, *Euglena gracilis*, *Emiliana huxleyi*, *Pavlova lutheri*, *Pavlova salina*, *Sphaeroforma arctica*, *Siganus canaliculatus*, *Thalassiosira pseudonana*, or *Thraustochytrium* sp.;

b) a Δ6 desaturase from Atlantic salmon, *Pythium irregulare*, *Mortierella alpina*, *Ostreococcus lucimarinus*, *Ostreococcus tauri*, *Siganus canaliculatus*, or *Primula farinosa*;

c) a Δ5 desaturase from *Thraustochytrium* sp., *Pavlova salina*, *Mortierella alpina*, Atlantic salmon or *Siganus canaliculatus*; and d) a Δ5/Δ6 desaturase from *Siganus canaliculatus* or zebrafish.

5. The method of claim 4, wherein the Δ4, Δ5 and/or Δ6 desaturase is a *Siganus canaliculatus* Δ4 desaturase comprising the amino acid sequence of SEQ ID NO: 174 and a *Siganus canaliculatus* Δ5/Δ6 desaturase comprising the amino acid sequence of SEQ ID NO: 172.

6. The method of claim 1, wherein the regions and/or amino acid residues which control the substrate specificity of the Δ4 desaturase comprises the amino acid sequence "YNYN" corresponding to position 280-283 in the amino acid sequence of SEQ ID NO: 174 and the regions and/or amino acid residues which control the substrate specificity of the Δ5 and/or Δ6 desaturase comprises the amino acid sequence "FHYQ" corresponding to position 278-281 of SEQ ID NO: 172.

7. The method of claim 1, wherein the amino acid sequences of the Δ4 desaturase and the Δ5 and/or Δ6 desaturase have a sequence identity of at least 40%.

* * * * *

SEQUENCE LISTING

```
<160> NUMBER OF SEQ ID NOS: 174

<210> SEQ ID NO 1
<211> LENGTH: 1332
<212> TYPE: DNA
<213> ORGANISM: artificial
<220> FEATURE:
<223> OTHER INFORMATION: chimeric protein

<400> SEQUENCE: 1
atgggaggtg gaggtcagcc gagggagtca ggggagcccg gcagcagtcc agctgtgtac      60
acctgggagg aggtgcagca ccactcttcc aggaatgacc agtggttggt gatcgatcga     120
aaagtttata acatctctca gtgggccaaa cggcacccag gagggtaccg ggtgattggc     180
cattatgctg gggaggatgc tacggaagca ttcactgctt tccaccctga cttgaaattt     240
gtgcaaaagt tcctcaagcc tttgctgata ggagagctgg cagccacaga gcccagccag     300
```

```
gaccgaaaca aaaatgccgc actcatacag gatttccaca ctttacgtca gcaagcggag      360
agtgagggtc tgtttcaagc tcgccctttg ttcttcctcc ttcatttggg tcacatcctg      420
ttgctggagg ctctggccct tctgatggtc tggcactggg gaacgggctg gctacagacg      480
ttactatgtg ccgttatgct ggcaactgct cagtctcagg ccggctggct tcagcacgac      540
tttggacacc tgtctgtctt caagaaatcc cgctggaatc acttggttca ccactttgtc      600
atcggccatt taagggagc ttctgccaac tggtggaatc atcgtcattt ccagcatcac      660
gctaaaccca acatcttcaa gaaggatcct gacatcaaca tggtggaccct ttttgtactt      720 ggagagactc aacctgtgga gtatggcgta aagaagatca aattaatgcc ctacaaccac      780
cagcaccagt acttccatct cattggacca ccgcttctca ttccagtttt ctacaactat      840
aacataatga tgaccatgat tactcgccgt gactatgtgg atctgtcttg gccatgacg       900 ttttacattc gctacatgtt gtgctatgtg ccggtctatg gccttttggg atcactggcg      960
ctcatgatgt ttgccaggtt tttggagagc cactggttcg tgtgggtaac tcagatgagt      1020
catctgccca tggacatcga caatgacaaa cgccgtgact ggctgtccat gcagttacaa      1080
gccacctgta acattgagaa gtctttttc aacgactggt tcagtggaca cctcaacttc      1140
caaattgaac accatttgtt cccgaggatg ccgcgccaca actaccacct ggtggctcca      1200
caggtccaga cactgtgtga gaaacatggg attccatacg aagtgaaaac gctgtggaaa      1260
ggcatggttg acgtcgtcag ggcactgaaa aaatcaggag acctctggct tgatgcatat      1320
ctccataaat ga                                                          1332

<210> SEQ ID NO 2
<211> LENGTH: 443
<212> TYPE: PRT
<213> ORGANISM: artificial
<220> FEATURE:
<223> OTHER INFORMATION: chimeric protein

<400> SEQUENCE: 2

Met Gly Gly Gly Gly Gln Pro Arg Glu Ser Gly Glu Pro Gly Ser Ser
1               5                   10                  15

Pro Ala Val Tyr Thr Trp Glu Glu Val Gln His His Ser Ser Arg Asn
                20                  25                  30

Asp Gln Trp Leu Val Ile Asp Arg Lys Val Tyr Asn Ile Ser Gln Trp
            35                  40                  45

Ala Lys Arg His Pro Gly Gly Tyr Arg Val Ile Gly His Tyr Ala Gly
        50                  55                  60

Glu Asp Ala Thr Glu Ala Phe Thr Ala Phe His Pro Asp Leu Lys Phe
65                  70                  75                  80

Val Gln Lys Phe Leu Lys Pro Leu Leu Ile Gly Glu Leu Ala Ala Thr
                85                  90                  95

Glu Pro Ser Gln Asp Arg Asn Lys Asn Ala Ala Leu Ile Gln Asp Phe
                100                 105                 110

His Thr Leu Arg Gln Gln Ala Glu Ser Glu Gly Leu Phe Gln Ala Arg
            115                 120                 125

Pro Leu Phe Phe Leu Leu His Leu Gly His Ile Leu Leu Leu Glu Ala
        130                 135                 140

Leu Ala Leu Leu Met Val Trp His Trp Gly Thr Gly Trp Leu Gln Thr
145                 150                 155                 160

Leu Leu Cys Ala Val Met Leu Ala Thr Ala Gln Ser Gln Ala Gly Trp
                165                 170                 175
```

-continued

| | | | | | | | | | | | |
|---|---|---|---|---|---|---|---|---|---|---|---|
|Leu|Gln|His|Asp<br>180|Phe|Gly|His|Leu|Ser<br>185|Val|Phe|Lys|Lys|Ser<br>190|Arg|Trp|

Leu Gln His Asp Phe Gly His Leu Ser Val Phe Lys Lys Ser Arg Trp
            180                 185                 190

Asn His Leu Val His His Phe Val Ile Gly His Leu Lys Gly Ala Ser
        195                 200                 205

Ala Asn Trp Trp Asn His Arg His Phe Gln His Ala Lys Pro Asn
210                 215                 220

Ile Phe Lys Lys Asp Pro Asp Ile Asn Met Val Asp Leu Phe Val Leu
225                 230                 235                 240

Gly Glu Thr Gln Pro Val Glu Tyr Gly Val Lys Ile Lys Leu Met
            245                 250                 255

Pro Tyr Asn His Gln His Gln Tyr Phe His Leu Ile Gly Pro Pro Leu
            260                 265                 270

Leu Ile Pro Val Phe Tyr Asn Tyr Asn Ile Met Met Thr Met Ile Thr
            275                 280                 285

Arg Arg Asp Tyr Val Asp Leu Ser Trp Ala Met Thr Phe Tyr Ile Arg
290                 295                 300

Tyr Met Leu Cys Tyr Val Pro Val Tyr Gly Leu Phe Gly Ser Leu Ala
305                 310                 315                 320

Leu Met Met Phe Ala Arg Phe Leu Glu Ser His Trp Phe Val Trp Val
            325                 330                 335

Thr Gln Met Ser His Leu Pro Met Asp Ile Asp Asn Asp Lys Arg Arg
            340                 345                 350

Asp Trp Leu Ser Met Gln Leu Gln Ala Thr Cys Asn Ile Glu Lys Ser
            355                 360                 365

Phe Phe Asn Asp Trp Phe Ser Gly His Leu Asn Phe Gln Ile Glu His
            370                 375                 380

His Leu Phe Pro Arg Met Pro Arg His Asn Tyr His Leu Val Ala Pro
385                 390                 395                 400

Gln Val Gln Thr Leu Cys Glu Lys His Gly Ile Pro Tyr Glu Val Lys
            405                 410                 415

Thr Leu Trp Lys Gly Met Val Asp Val Val Arg Ala Leu Lys Lys Ser
            420                 425                 430

Gly Asp Leu Trp Leu Asp Ala Tyr Leu His Lys
            435                 440

<210> SEQ ID NO 3
<211> LENGTH: 1332
<212> TYPE: DNA
<213> ORGANISM: artificial
<220> FEATURE:
<223> OTHER INFORMATION: chimeric protein

<400> SEQUENCE: 3
atgggaggtg gaggtcagcc gagggagtca ggggagcccg gcagcagtcc agctgtgtac      60
acctgggagg aggtgcagca ccactcttcc aggaatgacc agtggttggt gatcgatcga     120
aaagtttata acatctctca gtgggccaaa cggcacccag agggtaccg ggtgattggc      180 cattatgctg gggaggatgc tacggaagca ttcactgctt ccaccctga cttgaaattt      240 gtgcaaaagt tcctcaagcc tttgctgata ggagagctgg cagccacaga gcccagccag     300
gaccgaaaca aaatgccgc actcatacag gatttccaca ctttacgtca gcaagcggag      360
agtgagggtc tgtttcaagc tcgccctttg ttcttcctcc ttcatttggg tcacatcctg     420
ttgctggagg ctctggccct tctgatggtc tggcactggg aacgggctg gctacagacg      480 ttactatgtg ccgttatgct ggcaactgct cagtctcagg ccggctggct tcagcacgac     540

```
tttggacacc tgtctgtctt caagaaatcc cgctggaatc acttggttca ccactttgtc      600
atcggccatt taagggagc ttctgccaac tggtggaatc atcgtcattt ccagcatcac      660
gctaaaccca acatcttcaa gaaggatcct gacatcaaca tggtggacct ttttgtactt      720
ggagagactc aacctgtgga gtatggcgta aagaagatca aattaatgcc ctacaaccac      780
cagcaccagt acttccatct cattggacca ccgcttctca ttccagtttt ctacaactat      840
aacataatga tgaccatgat tactcgccgt gactatgtgg atctgtcttg ggccatgacg      900
ttttacattc gctacatgtt gtgctatgtg ccggtctacg gcctttttgg atctgtggta      960
ctcattgtat ttacaaggtt tttggagagc cactggttcg tgtgggtgac gcagatgaat     1020
catctgccga tggacatcaa ctatgagaac cacaacgact ggctgtccat gcagttgcaa     1080
gccacctgta atgttgagca gtctctcttc aacgactggt tcagtggaca tctcaacttt     1140
caaatcgaac accatttgtt tcccaccatg ccgcgccaca actaccacct ggtggttcca     1200
cgggtccgtg cactctgtga gaaacatgag ataccatacc aggtgaagac actgccgcag     1260
gccttcgctg atatcatcag gtcactgaaa aactcagggg agctctggct tgatgcatat     1320
ctccataaat ga                                                        1332
```

<210> SEQ ID NO 4
<211> LENGTH: 443
<212> TYPE: PRT
<213> ORGANISM: artificial
<220> FEATURE:
<223> OTHER INFORMATION: chimeric protein

<400> SEQUENCE: 4

```
Met Gly Gly Gly Gly Gln Pro Arg Glu Ser Gly Glu Pro Gly Ser Ser
1               5                   10                  15

Pro Ala Val Tyr Thr Trp Glu Glu Val Gln His His Ser Ser Arg Asn
            20                  25                  30

Asp Gln Trp Leu Val Ile Asp Arg Lys Val Tyr Asn Ile Ser Gln Trp
        35                  40                  45

Ala Lys Arg His Pro Gly Gly Tyr Arg Val Ile Gly His Tyr Ala Gly
    50                  55                  60

Glu Asp Ala Thr Glu Ala Phe Thr Ala Phe His Pro Asp Leu Lys Phe
65                  70                  75                  80

Val Gln Lys Phe Leu Lys Pro Leu Leu Ile Gly Glu Leu Ala Ala Thr
                85                  90                  95

Glu Pro Ser Gln Asp Arg Asn Lys Asn Ala Ala Leu Ile Gln Asp Phe
            100                 105                 110

His Thr Leu Arg Gln Gln Ala Glu Ser Glu Gly Leu Phe Gln Ala Arg
        115                 120                 125

Pro Leu Phe Phe Leu Leu His Leu Gly His Ile Leu Leu Leu Glu Ala
    130                 135                 140

Leu Ala Leu Leu Met Val Trp His Trp Gly Thr Gly Trp Leu Gln Thr
145                 150                 155                 160

Leu Leu Cys Ala Val Met Leu Ala Thr Ala Gln Ser Gln Ala Gly Trp
                165                 170                 175

Leu Gln His Asp Phe Gly His Leu Ser Val Phe Lys Lys Ser Arg Trp
            180                 185                 190

Asn His Leu Val His His Phe Val Ile Gly His Leu Lys Gly Ala Ser
        195                 200                 205

Ala Asn Trp Trp Asn His Arg His Phe Gln His His Ala Lys Pro Asn
```

```
            210                 215                 220
Ile Phe Lys Lys Asp Pro Asp Ile Asn Met Val Asp Leu Phe Val Leu
225                 230                 235                 240

Gly Glu Thr Gln Pro Val Glu Tyr Gly Val Lys Lys Ile Lys Leu Met
                245                 250                 255

Pro Tyr Asn His Gln His Gln Tyr Phe His Leu Ile Gly Pro Pro Leu
            260                 265                 270

Leu Ile Pro Val Phe Tyr Asn Tyr Asn Ile Met Met Thr Met Ile Thr
        275                 280                 285

Arg Arg Asp Tyr Val Asp Leu Ser Trp Ala Met Thr Phe Tyr Ile Arg
    290                 295                 300

Tyr Met Leu Cys Tyr Val Pro Val Tyr Gly Leu Phe Gly Ser Val Val
305                 310                 315                 320

Leu Ile Val Phe Thr Arg Phe Leu Glu Ser His Trp Phe Val Trp Val
                325                 330                 335

Thr Gln Met Asn His Leu Pro Met Asp Ile Asn Tyr Glu Asn His Asn
            340                 345                 350

Asp Trp Leu Ser Met Gln Leu Gln Ala Thr Cys Asn Val Glu Gln Ser
        355                 360                 365

Leu Phe Asn Asp Trp Phe Ser Gly His Leu Asn Phe Gln Ile Glu His
    370                 375                 380

His Leu Phe Pro Thr Met Pro Arg His Asn Tyr His Leu Val Val Pro
385                 390                 395                 400

Arg Val Arg Ala Leu Cys Glu Lys His Glu Ile Pro Tyr Gln Val Lys
                405                 410                 415

Thr Leu Pro Gln Ala Phe Ala Asp Ile Ile Arg Ser Leu Lys Asn Ser
            420                 425                 430

Gly Glu Leu Trp Leu Asp Ala Tyr Leu His Lys
        435                 440
```

<210> SEQ ID NO 5
<211> LENGTH: 1332
<212> TYPE: DNA
<213> ORGANISM: Artificial
<220> FEATURE:
<223> OTHER INFORMATION: chimeric protein

<400> SEQUENCE: 5

```
atgggaggtg gaggtcagcc gagggagtca ggggagcccg gcagcagtcc agctgtgtac      60
acctgggagg aggtgcagca ccactcttcc aggaatgacc agtggttggt gatcgatcga     120
aaagtttata acatctctca gtgggccaaa cggcacccag agggtaccg ggtgattggc      180
cattatgctg gggaggatgc tacggaagca ttcactgctt ccaccctga cttgaaattt      240
gtgcaaaagt tcctcaagcc tttgctgata ggagagctgg cagccacaga gcccagccag     300
gaccgaaaca aaaatgccgc actcatacag gatttccaca ctttacgtca gcaagcggag     360
agtgagggtc tgtttcaagc tcgccctttg ttcttcctcc ttcatttggg tcacatcctg     420
ttgctggagg ctctggccct tctgatggtc tggcactggg aacgggctg gctacagacg      480
ttactatgtg ccgttatgct ggcaactgct cagtctcagg ccggctggct tcagcacgac     540
tttggacacc tgtctgtctt caagaaatcc cgctggaatc acttggttca ccactttgtc     600
atcggccatt taagggagc ttctgccaac tggtggaatc atcgtcattt ccagcatcac     660
gctaaaccca acatcttcaa gaaggatcct gacatcaaca tggtggacct ttttgtactt     720
ggagagactc aacctgtgga gtatggcgta aagaagatca aattaatgcc ctacaaccac     780
```

```
cagcaccagt acttccatct cattggacca ccgcttctca ttccagtttt ctacaactat    840
aacataatga tgaccatgat ttctcaccgc tactggctgg atctggtgtg gtgcttgtcc    900
ttctaccttc ggtacatgtg ctgctatgtg ccggtctacg gcctttttgg atctgtggta    960
ctcattgtat ttacaaggtt tttggagagc cactggttcg tgtgggtgac gcagatgaat   1020
catctgccga tggacatcaa ctatgagaac cacaacgact ggctgtccat gcagttgcaa   1080
gccacctgta atgttgagca gtctctcttc aacgactggt tcagtggaca tctcaacttt   1140
caaatcgaac accatttgtt tcccaccatg ccgcgccaca actaccacct ggtggttcca   1200
cgggtccgtg cactctgtga aaacatgag ataccatacc aggtgaagac actgccgcag    1260
gccttcgctg atatcatcag gtcactgaaa aactcagggg agctctggct tgatgcatat   1320
ctccataaat ga                                                       1332
```

<210> SEQ ID NO 6
<211> LENGTH: 443
<212> TYPE: PRT
<213> ORGANISM: Artificial
<220> FEATURE:
<223> OTHER INFORMATION: chimeric protein

<400> SEQUENCE: 6

```
Met Gly Gly Gly Gly Gln Pro Arg Glu Ser Gly Glu Pro Gly Ser Ser
1               5                   10                  15

Pro Ala Val Tyr Thr Trp Glu Val Gln His His Ser Ser Arg Asn
            20                  25                  30

Asp Gln Trp Leu Val Ile Asp Arg Lys Val Tyr Asn Ile Ser Gln Trp
        35                  40                  45

Ala Lys Arg His Pro Gly Gly Tyr Arg Val Ile Gly His Tyr Ala Gly
    50                  55                  60

Glu Asp Ala Thr Glu Ala Phe Thr Ala Phe His Pro Asp Leu Lys Phe
65                  70                  75                  80

Val Gln Lys Phe Leu Lys Pro Leu Leu Ile Gly Glu Leu Ala Ala Thr
                85                  90                  95

Glu Pro Ser Gln Asp Arg Asn Lys Asn Ala Ala Leu Ile Gln Asp Phe
            100                 105                 110

His Thr Leu Arg Gln Gln Ala Glu Ser Glu Gly Leu Phe Gln Ala Arg
        115                 120                 125

Pro Leu Phe Phe Leu Leu His Leu Gly His Ile Leu Leu Leu Glu Ala
    130                 135                 140

Leu Ala Leu Leu Met Val Trp His Trp Gly Thr Gly Trp Leu Gln Thr
145                 150                 155                 160

Leu Leu Cys Ala Val Met Leu Ala Thr Ala Gln Ser Gln Ala Gly Trp
                165                 170                 175

Leu Gln His Asp Phe Gly His Leu Ser Val Phe Lys Lys Ser Arg Trp
            180                 185                 190

Asn His Leu Val His His Phe Val Ile Gly His Leu Lys Gly Ala Ser
        195                 200                 205

Ala Asn Trp Trp Asn His Arg His Phe Gln His His Ala Lys Pro Asn
    210                 215                 220

Ile Phe Lys Lys Asp Pro Asp Ile Asn Met Val Asp Leu Phe Val Leu
225                 230                 235                 240

Gly Glu Thr Gln Pro Val Glu Tyr Gly Val Lys Lys Ile Lys Leu Met
                245                 250                 255
```

Pro Tyr Asn His Gln His Gln Tyr Phe His Leu Ile Gly Pro Pro Leu
            260                 265                 270

Leu Ile Pro Val Phe Tyr Asn Tyr Asn Ile Met Met Thr Met Ile Ser
        275                 280                 285

His Arg Tyr Trp Leu Asp Leu Val Trp Cys Leu Ser Phe Tyr Leu Arg
    290                 295                 300

Tyr Met Cys Cys Tyr Val Pro Val Tyr Gly Leu Phe Gly Ser Val Val
305                 310                 315                 320

Leu Ile Val Phe Thr Arg Phe Leu Glu Ser His Trp Phe Val Trp Val
                325                 330                 335

Thr Gln Met Asn His Leu Pro Met Asp Ile Asn Tyr Glu Asn His Asn
            340                 345                 350

Asp Trp Leu Ser Met Gln Leu Gln Ala Thr Cys Asn Val Glu Gln Ser
        355                 360                 365

Leu Phe Asn Asp Trp Phe Ser Gly His Leu Asn Phe Gln Ile Glu His
    370                 375                 380

His Leu Phe Pro Thr Met Pro Arg His Asn Tyr His Leu Val Val Pro
385                 390                 395                 400

Arg Val Arg Ala Leu Cys Glu Lys His Glu Ile Pro Tyr Gln Val Lys
                405                 410                 415

Thr Leu Pro Gln Ala Phe Ala Asp Ile Ile Arg Ser Leu Lys Asn Ser
            420                 425                 430

Gly Glu Leu Trp Leu Asp Ala Tyr Leu His Lys
        435                 440

<210> SEQ ID NO 7
<211> LENGTH: 1332
<212> TYPE: DNA
<213> ORGANISM: Artificial
<220> FEATURE:
<223> OTHER INFORMATION: chimeric protein

<400> SEQUENCE: 7
atgggaggtg gaggtcagcc gagggagtca ggggagcccg gcagcagtcc agctgtgtac      60
acctgggagg aggtgcagca ccactcttcc aggaatgacc agtggttggt gatcgatcga     120
aaagtttata acatctctca gtgggccaaa cggcacccag agggtaccg ggtgattggc      180 cattatgctg gggaggatgc tacggaagca ttcactgctt ccaccctga cttgaaattt      240 gtgcaaaagt tcctcaagcc tttgctgata ggagagctgg cagccacaga gcccagccag     300
gaccgaaaca aaaatgccgc actcatacag gatttccaca ctttacgtca gcaagcggag     360
agtgagggtc tgtttcaagc tcgcccttg ttcttcctcc ttcatttggg tcacatcctg      420
ttgctggagg ctctggccct tctgatggtc tggcactggg aacgggctg gctacagacg     480 ttactatgtg ccgttatgct ggcaactgct cagtctcagg ccggctggct tcagcacgac     540
tttggacacc tgtctgtctt caagaaatcc cgctggaatc acttggttca ccactttgtc     600
atcggccatt taagggagc ttctgccaac tggtggaatc atcgtcattt ccagcatcac     660
gctaaaccca acatcttcaa gaaggatcct gacatcaaca tggtggacct ttttgtactt     720
ggagagactc aacctgtgga gtatggcgta aagaagatca aattaatgcc ctacaaccac     780
cagcaccagt acttccatct cattggacca ccgcttctca ttccagtttt ctacaactat     840
aacttgctga aaatcatgat ttctcaccgc tactggctgg atctggtgtg gtgcttgtcc     900
ttctaccttc ggtacatgtg ctgctatgtg ccggtctacg gcctttttgg atctgtggta     960
ctcattgtat ttacaaggtt tttggagagc cactggttcg tgtgggtgac gcagatgaat    1020

-continued

```
catctgccga tggacatcaa ctatgagaac cacaacgact ggctgtccat gcagttgcaa      1080
gccacctgta atgttgagca gtctctcttc aacgactggt tcagtggaca tctcaacttt      1140
caaatcgaac accatttgtt tcccaccatg ccgcgccaca actaccacct ggtggttcca      1200
cgggtccgtg cactctgtga gaaacatgag ataccatacc aggtgaagac actgccgcag      1260
gccttcgctg atatcatcag gtcactgaaa aactcagggg agctctggct tgatgcatat      1320
ctccataaat ga                                                          1332
```

<210> SEQ ID NO 8
<211> LENGTH: 443
<212> TYPE: PRT
<213> ORGANISM: Artificial
<220> FEATURE:
<223> OTHER INFORMATION: chimeric protein

<400> SEQUENCE: 8

```
Met Gly Gly Gly Gln Pro Arg Glu Ser Gly Glu Pro Gly Ser Ser
1               5                   10                  15

Pro Ala Val Tyr Thr Trp Glu Val Gln His His Ser Ser Arg Asn
            20                  25                  30

Asp Gln Trp Leu Val Ile Asp Arg Lys Val Tyr Asn Ile Ser Gln Trp
        35                  40                  45

Ala Lys Arg His Pro Gly Gly Tyr Arg Val Ile Gly His Tyr Ala Gly
    50                  55                  60

Glu Asp Ala Thr Glu Ala Phe Thr Ala Phe His Pro Asp Leu Lys Phe
65                  70                  75                  80

Val Gln Lys Phe Leu Lys Pro Leu Leu Ile Gly Glu Leu Ala Ala Thr
                85                  90                  95

Glu Pro Ser Gln Asp Arg Asn Lys Asn Ala Ala Leu Ile Gln Asp Phe
            100                 105                 110

His Thr Leu Arg Gln Gln Ala Glu Ser Glu Gly Leu Phe Gln Ala Arg
        115                 120                 125

Pro Leu Phe Phe Leu Leu His Leu Gly His Ile Leu Leu Leu Glu Ala
    130                 135                 140

Leu Ala Leu Leu Met Val Trp His Trp Gly Thr Gly Trp Leu Gln Thr
145                 150                 155                 160

Leu Leu Cys Ala Val Met Leu Ala Thr Ala Gln Ser Gln Ala Gly Trp
                165                 170                 175

Leu Gln His Asp Phe Gly His Leu Ser Val Phe Lys Lys Ser Arg Trp
            180                 185                 190

Asn His Leu Val His His Phe Val Ile Gly His Leu Lys Gly Ala Ser
        195                 200                 205

Ala Asn Trp Trp Asn His Arg His Phe Gln His Ala Lys Pro Asn
    210                 215                 220

Ile Phe Lys Lys Asp Pro Asp Ile Asn Met Val Asp Leu Phe Val Leu
225                 230                 235                 240

Gly Glu Thr Gln Pro Val Glu Tyr Gly Val Lys Lys Ile Lys Leu Met
                245                 250                 255

Pro Tyr Asn His Gln His Gln Tyr Phe His Leu Ile Gly Pro Pro Leu
            260                 265                 270

Leu Ile Pro Val Phe Tyr Asn Tyr Asn Leu Leu Lys Ile Met Ile Ser
        275                 280                 285

His Arg Tyr Trp Leu Asp Leu Val Trp Cys Leu Ser Phe Tyr Leu Arg
    290                 295                 300
```

```
Tyr Met Cys Cys Tyr Val Pro Val Tyr Gly Leu Phe Gly Ser Val Val
305                 310                 315                 320

Leu Ile Val Phe Thr Arg Phe Leu Glu Ser His Trp Phe Val Trp Val
                325                 330                 335

Thr Gln Met Asn His Leu Pro Met Asp Ile Asn Tyr Glu Asn His Asn
            340                 345                 350

Asp Trp Leu Ser Met Gln Leu Gln Ala Thr Cys Asn Val Glu Gln Ser
        355                 360                 365

Leu Phe Asn Asp Trp Phe Ser Gly His Leu Asn Phe Gln Ile Glu His
    370                 375                 380

His Leu Phe Pro Thr Met Pro Arg His Asn Tyr His Leu Val Val Pro
385                 390                 395                 400

Arg Val Arg Ala Leu Cys Glu Lys His Glu Ile Pro Tyr Gln Val Lys
                405                 410                 415

Thr Leu Pro Gln Ala Phe Ala Asp Ile Ile Arg Ser Leu Lys Asn Ser
            420                 425                 430

Gly Glu Leu Trp Leu Asp Ala Tyr Leu His Lys
        435                 440
```

```
<210> SEQ ID NO 9
<211> LENGTH: 1338
<212> TYPE: DNA
<213> ORGANISM: Artificial
<220> FEATURE:
<223> OTHER INFORMATION: chimeric protein

<400> SEQUENCE: 9
atgggaggtg gaggtcagct gggggagtca ggggagaatg gctgcaagtc agctgctggt      60
gtgtacactt ggaggaggt gcagcaccac agcaacagga tgaccagtg gttggtcatt      120
gatcgcaagg tttataatgt cacccagtgg gccaagagac acccaggagg gtttcgggtc      180
ctcaaccact atgctggaga ggatgctacg gaggcattca ctgcttttca ccccgacata      240
aaatttgtac aaaagtatat gaagcctttg ctggtaggag agctggctgc aacggagccc      300
agtcaggatc aagacaaaaa tgccgcactc atacaggatt ccacacttt acgtcagcaa      360
gcggagagtg agggtctgtt tcaagctcgc cctttgttct tcctccttca tttgggtcac      420
atcctgttgc tggaggctct ggcccttctg atggtctggc actggggaac gggctggcta      480
cagacgttac tatgtgccgt tatgctggca actgctcagt ctcaggccgg ctggcttcag      540
cacgactttg acacctgtc tgtcttcaag aaatcccgct ggaatcactt ggttcacaag      600
tttgtcatcg ccatttaaa gggagcttct gccaactggt ggaatcatcg tcatttccag      660
catcacgcta aacccaacat cttcaagaag atcctgaca tcaacatggt ggacttttt      720
gtacttggag agactcaacc tgtggagtat ggcataaaga agattaaaaa tatgccctat      780
aaccaccagc acaagtattt cttttttggtt gcgccaccac ttcttattcc agttttttc      840
cactaccagt tgctgaaaat catgatttct caccgctact ggctggatct ggtgtggtgc      900
tgtccttct accttcggta catgtgctgc tatgtgccgg tctacggcct ttttggatct      960
gtggtactca ttgtatttac aaggtttttg gagagccact ggttcgtgtg gtgacgcag      1020
atgaatcatc tgccgatgga catcaactat gagaaccaca cgactggct gtccatgcag      1080
ttgcaagcca cctgtaatgt tgagcagtct ctcttcaacg actggttcag tggacatctc      1140
aactttcaaa tcgaacacca tttgtttccc ccatgccgc ccacaacta ccacctggtg      1200
gttccacggg tccgtgcact ctgtgagaaa catgagatac ataccaggt gaagacactg      1260
```

-continued

```
ccgcaggcct tcgctgatat catcaggtca ctgaaaaact caggggagct ctggcttgat    1320
gcatatctcc ataaatga                                                  1338
```

<210> SEQ ID NO 10
<211> LENGTH: 445
<212> TYPE: PRT
<213> ORGANISM: Artificial
<220> FEATURE:
<223> OTHER INFORMATION: chimeric protein

<400> SEQUENCE: 10

```
Met Gly Gly Gly Gln Leu Gly Glu Ser Gly Glu Asn Gly Cys Lys
1               5                   10                  15

Ser Ala Ala Gly Val Tyr Thr Trp Glu Glu Val Gln His His Ser Asn
            20                  25                  30

Arg Asn Asp Gln Trp Leu Val Ile Asp Arg Lys Val Tyr Asn Val Thr
        35                  40                  45

Gln Trp Ala Lys Arg His Pro Gly Gly Phe Arg Val Leu Asn His Tyr
    50                  55                  60

Ala Gly Glu Asp Ala Thr Glu Ala Phe Thr Ala Phe His Pro Asp Ile
65                  70                  75                  80

Lys Phe Val Gln Lys Tyr Met Lys Pro Leu Leu Val Gly Glu Leu Ala
                85                  90                  95

Ala Thr Glu Pro Ser Gln Asp Gln Lys Asn Ala Ala Leu Ile Gln
            100                 105                 110

Asp Phe His Thr Leu Arg Gln Gln Ala Glu Ser Glu Gly Leu Phe Gln
        115                 120                 125

Ala Arg Pro Leu Phe Phe Leu Leu His Leu Gly His Ile Leu Leu Leu
    130                 135                 140

Glu Ala Leu Ala Leu Leu Met Val Trp His Trp Gly Thr Gly Trp Leu
145                 150                 155                 160

Gln Thr Leu Leu Cys Ala Val Met Leu Ala Thr Ala Gln Ser Gln Ala
                165                 170                 175

Gly Trp Leu Gln His Asp Phe Gly His Leu Ser Val Phe Lys Lys Ser
            180                 185                 190

Arg Trp Asn His Leu Val His Lys Phe Val Ile Gly His Leu Lys Gly
        195                 200                 205

Ala Ser Ala Asn Trp Trp Asn His Arg His Phe Gln His His Ala Lys
    210                 215                 220

Pro Asn Ile Phe Lys Lys Asp Pro Asp Ile Asn Met Val Asp Leu Phe
225                 230                 235                 240

Val Leu Gly Glu Thr Gln Pro Val Glu Tyr Gly Ile Lys Lys Ile Lys
                245                 250                 255

Asn Met Pro Tyr Asn His Gln His Lys Tyr Phe Phe Leu Val Ala Pro
            260                 265                 270

Pro Leu Leu Ile Pro Val Phe Phe His Tyr Gln Leu Leu Lys Ile Met
        275                 280                 285

Ile Ser His Arg Tyr Trp Leu Asp Leu Val Trp Cys Leu Ser Phe Tyr
    290                 295                 300

Leu Arg Tyr Met Cys Cys Tyr Val Pro Val Tyr Gly Leu Phe Gly Ser
305                 310                 315                 320

Val Val Leu Ile Val Phe Thr Arg Phe Leu Glu Ser His Trp Phe Val
                325                 330                 335

Trp Val Thr Gln Met Asn His Leu Pro Met Asp Ile Asn Tyr Glu Asn
```

```
                340             345             350
His Asn Asp Trp Leu Ser Met Gln Leu Gln Ala Thr Cys Asn Val Glu
            355                 360                 365

Gln Ser Leu Phe Asn Asp Trp Phe Ser Gly His Leu Asn Phe Gln Ile
        370                 375                 380

Glu His His Leu Phe Pro Thr Met Pro Arg His Asn Tyr His Leu Val
385                 390                 395                 400

Val Pro Arg Val Arg Ala Leu Cys Glu Lys His Glu Ile Pro Tyr Gln
                405                 410                 415

Val Lys Thr Leu Pro Gln Ala Phe Ala Asp Ile Ile Arg Ser Leu Lys
            420                 425                 430

Asn Ser Gly Glu Leu Trp Leu Asp Ala Tyr Leu His Lys
        435                 440                 445

<210> SEQ ID NO 11
<211> LENGTH: 1338
<212> TYPE: DNA
<213> ORGANISM: Artificial
<220> FEATURE:
<223> OTHER INFORMATION: chimeric protein

<400> SEQUENCE: 11
atgggaggtg gaggtcagct gggggagtca ggggagaatg gctgcaagtc agctgctggt      60
gtgtacactt gggaggaggt gcagcaccac agcaacagga atgaccagtg gttggtcatt     120
gatcgcaagg tttataatgt cacccagtgg gccaagagac acccaggagg gtttcgggtc     180
ctcaaccact atgctggaga ggatgctacg gaggcattca ctgcttttca ccccgacata     240
aaatttgtac aaaagtatat gaagcctttg ctggtaggag agctggctgc aacggagccc     300
agtcaggatc aagacaaaaa tgccgcactc atacaggatt ccacactttt acgtcagcaa     360
gcggagagtg agggtctgtt tcaagctcgc cctttgttct tcctccttca tttgggtcac     420
atcctgttgc tggaggctct ggcccttctg atggtctggc actggggaac gggctggcta     480
cagacgttac tatgtgccgt tatgctggca actgctcagt ctcaggccgg ctggcttcag     540
cacgactttg gacacctgtc tgtcttcaag aaatcccgct ggaatcactt ggttcacaag     600
tttgtcatcg ccatttaaa gggagcttct gccaactggt ggaatcatcg tcatttccag     660
catcacgcta aacccaacat cttcaagaag gatcctgaca tcaacatggt ggaccttttt     720
gtacttggag agactcaacc tgtggagtat ggcataaaga agattaaaaa tatgccctat     780
aaccaccagc acaagtattt cttttttggtt gcgccaccac ttcttattcc agttttttc      840
cactaccagt tgctgaaaat catgatttct caccgctact ggctggatct ggtgtggtgc     900
ttgtccttct accttcggta catgtgctgc tatgtgccgg tctacggcct ttttggatca     960
ctggcgctca tgatgtttgc caggtttttg gagagccact ggttcgtgtg gtaactcag    1020
atgagtcatc tgcccatgga catcgacaat gacaaacgcc gtgactggct gtccatgcag    1080
ttacaagcca cctgtaacat tgagaagtct ttttttcaacg actggttcag tggacacctc    1140
aacttccaaa ttgaacacca tttgttcccg aggatgccgc gccacaacta ccacctggtg    1200
gctccacagg tccagacact gtgtgagaaa catgggattc catacgaagt gaaaacgctg    1260
tggaaaggca tggttgacgt cgtcagggca ctgaaaaaat caggagacct ctggcttgat    1320
gcatatctcc ataaatga                                                  1338

<210> SEQ ID NO 12
<211> LENGTH: 445
```

```
<212> TYPE: PRT
<213> ORGANISM: Artificial
<220> FEATURE:
<223> OTHER INFORMATION: chimeric protein

<400> SEQUENCE: 12

Met Gly Gly Gly Gly Gln Leu Gly Glu Ser Gly Glu Asn Gly Cys Lys
1               5                   10                  15

Ser Ala Ala Gly Val Tyr Thr Trp Glu Glu Val Gln His His Ser Asn
            20                  25                  30

Arg Asn Asp Gln Trp Leu Val Ile Asp Arg Lys Val Tyr Asn Val Thr
        35                  40                  45

Gln Trp Ala Lys Arg His Pro Gly Gly Phe Arg Val Leu Asn His Tyr
    50                  55                  60

Ala Gly Glu Asp Ala Thr Glu Ala Phe Thr Ala Phe His Pro Asp Ile
65                  70                  75                  80

Lys Phe Val Gln Lys Tyr Met Lys Pro Leu Leu Val Gly Glu Leu Ala
                85                  90                  95

Ala Thr Glu Pro Ser Gln Asp Gln Lys Asn Ala Ala Leu Ile Gln
            100                 105                 110

Asp Phe His Thr Leu Arg Gln Gln Ala Glu Ser Glu Gly Leu Phe Gln
            115                 120                 125

Ala Arg Pro Leu Phe Phe Leu Leu His Leu Gly His Ile Leu Leu Leu
130                 135                 140

Glu Ala Leu Ala Leu Leu Met Val Trp His Trp Gly Thr Gly Trp Leu
145                 150                 155                 160

Gln Thr Leu Leu Cys Ala Val Met Leu Ala Thr Ala Gln Ser Gln Ala
                165                 170                 175

Gly Trp Leu Gln His Asp Phe Gly His Leu Ser Val Phe Lys Lys Ser
            180                 185                 190

Arg Trp Asn His Leu Val His Lys Phe Val Ile Gly His Leu Lys Gly
        195                 200                 205

Ala Ser Ala Asn Trp Trp Asn His Arg His Phe Gln His His Ala Lys
    210                 215                 220

Pro Asn Ile Phe Lys Lys Asp Pro Asp Ile Asn Met Val Asp Leu Phe
225                 230                 235                 240

Val Leu Gly Glu Thr Gln Pro Val Glu Tyr Gly Ile Lys Lys Ile Lys
                245                 250                 255

Asn Met Pro Tyr Asn His Gln His Lys Tyr Phe Phe Leu Val Ala Pro
            260                 265                 270

Pro Leu Leu Ile Pro Val Phe Phe His Tyr Gln Leu Leu Lys Ile Met
        275                 280                 285

Ile Ser His Arg Tyr Trp Leu Asp Leu Val Trp Cys Leu Ser Phe Tyr
    290                 295                 300

Leu Arg Tyr Met Cys Cys Tyr Val Pro Val Tyr Gly Leu Phe Gly Ser
305                 310                 315                 320

Leu Ala Leu Met Met Phe Ala Arg Phe Leu Glu Ser His Trp Phe Val
                325                 330                 335

Trp Val Thr Gln Met Ser His Leu Pro Met Asp Ile Asp Asn Asp Lys
            340                 345                 350

Arg Arg Asp Trp Leu Ser Met Gln Leu Gln Ala Thr Cys Asn Ile Glu
        355                 360                 365

Lys Ser Phe Phe Asn Asp Trp Phe Ser Gly His Leu Asn Phe Gln Ile
    370                 375                 380
```

Glu His His Leu Phe Pro Arg Met Pro Arg His Asn Tyr His Leu Val
385                 390                 395                 400

Ala Pro Gln Val Gln Thr Leu Cys Glu Lys His Gly Ile Pro Tyr Glu
            405                 410                 415

Val Lys Thr Leu Trp Lys Gly Met Val Asp Val Arg Ala Leu Lys
        420                 425                 430

Lys Ser Gly Asp Leu Trp Leu Asp Ala Tyr Leu His Lys
        435                 440                 445

<210> SEQ ID NO 13
<211> LENGTH: 1338
<212> TYPE: DNA
<213> ORGANISM: Artificial
<220> FEATURE:
<223> OTHER INFORMATION: chimeric protein

<400> SEQUENCE: 13
atgggaggtg gaggtcagct gggggagtca ggggagaatg gctgcaagtc agctgctggt      60
gtgtacactt gggaggaggt gcagcaccac agcaacagga tgaccagtg gttggtcatt     120 gatcgcaagg tttataatgt cacccagtgg gccaagagac acccaggagg gtttcgggtc     180
ctcaaccact atgctggaga ggatgctacg gaggcattca ctgcttttca ccccgacata     240
aaatttgtac aaaagtatat gaagcctttg ctggtaggag agctggctgc aacggagccc     300
agtcaggatc aagacaaaaa tgccgcactc atacaggatt ccacacttt acgtcagcaa     360 gcggagagtg agggtctgtt tcaagctcgc cctttgttct tcctccttca tttgggtcac     420
atcctgttgc tggaggctct ggcccttctg atggtctggc actggggaac gggctggcta     480
cagacgttac tatgtgccgt tatgctggca actgctcagt ctcaggccgg ctggcttcag     540
cacgactttg acacctgtc tgtcttcaag aaatcccgct ggaatcactt ggttcacaag     600
tttgtcatcg ccatttaaa gggagcttct gccaactggt ggaatcatcg tcatttccag     660
catcacgcta acccaacat cttcaagaag atcctgaca tcaacatggt ggaccttttt     720
gtacttggag agactcaacc tgtggagtat ggcataaaga agattaaaaa tatgccctat     780
aaccaccagc acaagtattt cttttttggtt gcgccaccac ttcttattcc agtttttttc     840
cactaccagt tgctgaaaat catgattact cgccgtgact atgtggatct gtcttgggcc     900 atgacgttttt acattcgcta catgttgtgc tatgtgccgg tctatggcct ttttggatca     960
ctggcgctca tgatgtttgc caggttttttg gagagccact ggttcgtgtg ggtaactcag    1020
atgagtcatc tgcccatgga catcgacaat gacaaacgcc gtgactggct gtccatgcag    1080
ttacaagcca cctgtaacat tgagaagtct ttttttcaacg actggttcag tggacacctc    1140
aacttccaaa ttgaacacca tttgttccccg aggatgccgc gccacaacta ccacctggtg    1200
gctccacagg tccagacact gtgtgagaaa catgggattc catacgaagt gaaaacgctg    1260
tggaaaggca tggttgacgt cgtcagggca ctgaaaaaat caggagacct ctggcttgat    1320
gcatatctcc ataaatga                                                  1338

<210> SEQ ID NO 14
<211> LENGTH: 445
<212> TYPE: PRT
<213> ORGANISM: Artificial
<220> FEATURE:
<223> OTHER INFORMATION: chimeric protein

<400> SEQUENCE: 14

Met Gly Gly Gly Gly Gln Leu Gly Glu Ser Gly Glu Asn Gly Cys Lys

```
1               5                    10                   15
Ser Ala Ala Gly Val Tyr Thr Trp Glu Glu Val Gln His His Ser Asn
                20                   25                   30
Arg Asn Asp Gln Trp Leu Val Ile Asp Arg Lys Val Tyr Asn Val Thr
                35                   40                   45
Gln Trp Ala Lys Arg His Pro Gly Gly Phe Arg Val Leu Asn His Tyr
 50                   55                   60
Ala Gly Glu Asp Ala Thr Glu Ala Phe Thr Ala Phe His Pro Asp Ile
 65                   70                   75                   80
Lys Phe Val Gln Lys Tyr Met Lys Pro Leu Leu Val Gly Glu Leu Ala
                85                   90                   95
Ala Thr Glu Pro Ser Gln Asp Gln Lys Asn Ala Ala Leu Ile Gln
                100                  105                  110
Asp Phe His Thr Leu Arg Gln Gln Ala Glu Ser Glu Gly Leu Phe Gln
                115                  120                  125
Ala Arg Pro Leu Phe Phe Leu Leu His Leu Gly His Ile Leu Leu Leu
 130                  135                  140
Glu Ala Leu Ala Leu Leu Met Val Trp His Trp Gly Thr Gly Trp Leu
 145                  150                  155                  160
Gln Thr Leu Leu Cys Ala Val Met Leu Ala Thr Ala Gln Ser Gln Ala
                165                  170                  175
Gly Trp Leu Gln His Asp Phe Gly His Leu Ser Val Phe Lys Lys Ser
                180                  185                  190
Arg Trp Asn His Leu Val His Lys Phe Val Ile Gly His Leu Lys Gly
                195                  200                  205
Ala Ser Ala Asn Trp Trp Asn His Arg His Phe Gln His His Ala Lys
 210                  215                  220
Pro Asn Ile Phe Lys Lys Asp Pro Asp Ile Asn Met Val Asp Leu Phe
 225                  230                  235                  240
Val Leu Gly Glu Thr Gln Pro Val Glu Tyr Gly Ile Lys Lys Ile Lys
                245                  250                  255
Asn Met Pro Tyr Asn His Gln His Lys Tyr Phe Phe Leu Val Ala Pro
                260                  265                  270
Pro Leu Leu Ile Pro Val Phe Phe His Tyr Gln Leu Leu Lys Ile Met
                275                  280                  285
Ile Thr Arg Arg Asp Tyr Val Asp Leu Ser Trp Ala Met Thr Phe Tyr
                290                  295                  300
Ile Arg Tyr Met Leu Cys Tyr Val Pro Val Tyr Gly Leu Phe Gly Ser
 305                  310                  315                  320
Leu Ala Leu Met Met Phe Ala Arg Phe Leu Glu Ser His Trp Phe Val
                325                  330                  335
Trp Val Thr Gln Met Ser His Leu Pro Met Asp Ile Asp Asn Asp Lys
                340                  345                  350
Arg Arg Asp Trp Leu Ser Met Gln Leu Gln Ala Thr Cys Asn Ile Glu
                355                  360                  365
Lys Ser Phe Phe Asn Asp Trp Phe Ser Gly His Leu Asn Phe Gln Ile
 370                  375                  380
Glu His His Leu Phe Pro Arg Met Pro Arg His Asn Tyr His Leu Val
 385                  390                  395                  400
Ala Pro Gln Val Gln Thr Leu Cys Glu Lys His Gly Ile Pro Tyr Glu
                405                  410                  415
Val Lys Thr Leu Trp Lys Gly Met Val Asp Val Val Arg Ala Leu Lys
                420                  425                  430
```

Lys Ser Gly Asp Leu Trp Leu Asp Ala Tyr Leu His Lys
        435                 440                 445

<210> SEQ ID NO 15
<211> LENGTH: 1338
<212> TYPE: DNA
<213> ORGANISM: Artificial
<220> FEATURE:
<223> OTHER INFORMATION: chimeric protein

<400> SEQUENCE: 15

| | | | | | |
|---|---|---|---|---|---|
| atgggaggtg | aggtcagct | gggggagtca | ggggagaatg | gctgcaagtc | agctgctggt | 60 |
| gtgtacactt | gggaggaggt | gcagcaccac | agcaacagga | atgaccagtg | gttggtcatt | 120 |
| gatcgcaagg | tttataatgt | cacccagtgg | gccaagagac | acccaggagg | gtttcgggtc | 180 |
| ctcaaccact | atgctggaga | ggatgctacg | gaggcattca | ctgcttttca | ccccgacata | 240 |
| aaatttgtac | aaaagtatat | gaagcctttg | ctggtaggag | agctggctgc | aacggagccc | 300 |
| agtcaggatc | aagacaaaaa | tgccgcactc | atacaggatt | ccacactttt | acgtcagcaa | 360 |
| gcggagagtg | agggtctgtt | tcaagctcgc | cctttgttct | tcctccttca | tttgggtcac | 420 |
| atcctgttgc | tggaggctct | ggcccttctg | atggtctggc | actggggaac | gggctggcta | 480 |
| cagacgttac | tatgtgccgt | tatgctggca | actgctcagt | ctcaggccgg | ctggcttcag | 540 |
| cacgactttg | gacacctgtc | tgtcttcaag | aaatcccgct | ggaatcactt | ggttcacaag | 600 |
| tttgtcatcg | ccatttaaa | gggagcttct | gccaactggt | ggaatcatcg | tcatttccag | 660 |
| catcacgcta | aacccaacat | cttcaagaag | gatcctgaca | tcaacatggt | ggaccttttt | 720 |
| gtacttggag | agactcaacc | tgtggagtat | ggcataaaga | agattaaaaa | tatgccctat | 780 |
| aaccaccagc | acaagtattt | ctttttggtt | gcgccaccac | ttcttattcc | agttttttc | 840 |
| cactaccaga | taatgatgac | catgattact | cgccgtgact | atgtggatct | gtcttgggcc | 900 |
| atgacgtttt | acattcgcta | catgttgtgc | tatgtgccgg | tctatggcct | ttttggatca | 960 |
| ctggcgctca | tgatgtttgc | caggttttg | gagagccact | ggttcgtgtg | ggtaactcag | 1020 |
| atgagtcatc | tgcccatgga | catcgacaat | gacaaacgcc | gtgactggct | gtccatgcag | 1080 |
| ttacaagcca | cctgtaacat | tgagaagtct | tttttcaacg | actggttcag | tggacacctc | 1140 |
| aacttccaaa | ttgaacacca | tttgttcccg | aggatgccgc | gccacaacta | ccacctggtg | 1200 |
| gctccacagg | tccagacact | gtgtgagaaa | catgggattc | catacgaagt | gaaaacgctg | 1260 |
| tggaaaggca | tggttgacgt | cgtcagggca | ctgaaaaaat | caggagacct | ctggcttgat | 1320 |
| gcatatctcc | ataaatga | | | | | 1338 |

<210> SEQ ID NO 16
<211> LENGTH: 445
<212> TYPE: PRT
<213> ORGANISM: Artificial
<220> FEATURE:
<223> OTHER INFORMATION: chimeric protein

<400> SEQUENCE: 16

Met Gly Gly Gly Gly Gln Leu Gly Glu Ser Gly Glu Asn Gly Cys Lys
1               5                   10                  15

Ser Ala Ala Gly Val Tyr Thr Trp Glu Glu Val Gln His His Ser Asn
            20                  25                  30

Arg Asn Asp Gln Trp Leu Val Ile Asp Arg Lys Val Tyr Asn Val Thr
        35                  40                  45

```
Gln Trp Ala Lys Arg His Pro Gly Gly Phe Arg Val Leu Asn His Tyr
 50                  55                  60
Ala Gly Glu Asp Ala Thr Glu Ala Phe Thr Ala Phe His Pro Asp Ile
 65                  70                  75                  80
Lys Phe Val Gln Lys Tyr Met Lys Pro Leu Leu Val Gly Glu Leu Ala
                 85                  90                  95
Ala Thr Glu Pro Ser Gln Asp Gln Lys Asn Ala Ala Leu Ile Gln
                100                 105                 110
Asp Phe His Thr Leu Arg Gln Gln Ala Glu Ser Glu Gly Leu Phe Gln
                115                 120                 125
Ala Arg Pro Leu Phe Phe Leu Leu His Leu Gly His Ile Leu Leu Leu
130                 135                 140
Glu Ala Leu Ala Leu Leu Met Val Trp His Trp Gly Thr Gly Trp Leu
145                 150                 155                 160
Gln Thr Leu Leu Cys Ala Val Met Leu Ala Thr Ala Gln Ser Gln Ala
                165                 170                 175
Gly Trp Leu Gln His Asp Phe Gly His Leu Ser Val Phe Lys Lys Ser
                180                 185                 190
Arg Trp Asn His Leu Val His Lys Phe Val Ile Gly His Leu Lys Gly
                195                 200                 205
Ala Ser Ala Asn Trp Trp Asn His Arg His Phe Gln His His Ala Lys
210                 215                 220
Pro Asn Ile Phe Lys Lys Asp Pro Asp Ile Asn Met Val Asp Leu Phe
225                 230                 235                 240
Val Leu Gly Glu Thr Gln Pro Val Glu Tyr Gly Ile Lys Lys Ile Lys
                245                 250                 255
Asn Met Pro Tyr Asn His Gln His Lys Tyr Phe Phe Leu Val Ala Pro
                260                 265                 270
Pro Leu Leu Ile Pro Val Phe Phe His Tyr Gln Ile Met Met Thr Met
                275                 280                 285
Ile Thr Arg Arg Asp Tyr Val Asp Leu Ser Trp Ala Met Thr Phe Tyr
                290                 295                 300
Ile Arg Tyr Met Leu Cys Tyr Val Pro Val Tyr Gly Leu Phe Gly Ser
305                 310                 315                 320
Leu Ala Leu Met Met Phe Ala Arg Phe Leu Glu Ser His Trp Phe Val
                325                 330                 335
Trp Val Thr Gln Met Ser His Leu Pro Met Asp Ile Asp Asn Asp Lys
                340                 345                 350
Arg Arg Asp Trp Leu Ser Met Gln Leu Gln Ala Thr Cys Asn Ile Glu
                355                 360                 365
Lys Ser Phe Phe Asn Asp Trp Phe Ser Gly His Leu Asn Phe Gln Ile
                370                 375                 380
Glu His His Leu Phe Pro Arg Met Pro Arg His Asn Tyr His Leu Val
385                 390                 395                 400
Ala Pro Gln Val Gln Thr Leu Cys Glu Lys His Gly Ile Pro Tyr Glu
                405                 410                 415
Val Lys Thr Leu Trp Lys Gly Met Val Asp Val Val Arg Ala Leu Lys
                420                 425                 430
Lys Ser Gly Asp Leu Trp Leu Asp Ala Tyr Leu His Lys
                435                 440                 445

<210> SEQ ID NO 17
<211> LENGTH: 1338
<212> TYPE: DNA
```

```
<213> ORGANISM: Artificial
<220> FEATURE:
<223> OTHER INFORMATION: chimeric protein

<400> SEQUENCE: 17
atgggaggtg aggtcagct gggggagtca ggggagaatg gctgcaagtc agctgctggt      60
gtgtacactt gggaggaggt gcagcaccac agcaacagga atgaccagtg gttggtcatt     120
gatcgcaagg tttataatgt cacccagtgg gccaagagac acccaggagg gtttcgggtc     180
ctcaaccact atgctggaga ggatgctacg gaggcattca ctgcttttca ccccgacata     240
aaatttgtac aaaagtatat gaagcctttg ctggtaggag agctggctgc aacggagccc     300
agtcaggatc aagacaaaaa tgccgcactc atacaggatt ccacacttt acgtcagcaa      360
gcggagagtg agggtctgtt tcaagctcgc cctttgttct tcctccttca tttgggtcac     420
atcctgttgc tggaggctct ggcccttctg atggtctggc actggggaac gggctggcta     480
cagacgttac tatgtgccgt tatgctggca actgctcagt ctcaggccgg ctggcttcag     540
cacgactttg acacctgtc tgtcttcaag aaatcccgct ggaatcactt ggttcacaag      600
tttgtcatcg ccatttaaa gggagcttct gccaactggt ggaatcatcg tcatttccag      660
catcacgcta aacccaacat cttcaagaag atcctgaca tcaacatggt ggaccttttt      720
gtacttggag agactcaacc tgtggagtat ggcataaaga agattaaaaa tatgccctat     780
aaccaccagc acaagtattt cttttttggtt gcgccaccac ttcttattcc agttttcttc     840
aactataaca taatgatgac catgattact cgccgtgact atgtggatct gtcttgggcc     900
atgacgtttt acattcgcta catgttgtgc tatgtgccgg tctatggcct ttttggatca     960
ctggcgctca tgatgtttgc caggttttttg gagagccact ggttcgtgtg ggtaactcag    1020
atgagtcatc tgcccatgga catcgacaat gacaaacgcc gtgactggct gtccatgcag    1080
ttacaagcca cctgtaacat tgagaagtct tttttcaacg actggttcag tggacacctc    1140
aacttccaaa ttgaacacca tttgttcccg aggatgccgc gccacaacta ccacctggtg    1200
gctccacagg tccagacact gtgtgagaaa catgggattc catacgaagt gaaaacgctg    1260
tggaaaggca tggttgacgt cgtcagggca ctgaaaaaat caggagacct ctggcttgat    1320
gcatatctcc ataaatga                                                  1338

<210> SEQ ID NO 18
<211> LENGTH: 445
<212> TYPE: PRT
<213> ORGANISM: Artificial
<220> FEATURE:
<223> OTHER INFORMATION: chimeric protein

<400> SEQUENCE: 18

Met Gly Gly Gly Gly Gln Leu Gly Glu Ser Gly Glu Asn Gly Cys Lys
1               5                   10                  15

Ser Ala Ala Gly Val Tyr Thr Trp Glu Glu Val Gln His His Ser Asn
            20                  25                  30

Arg Asn Asp Gln Trp Leu Val Ile Asp Arg Lys Val Tyr Asn Val Thr
        35                  40                  45

Gln Trp Ala Lys Arg His Pro Gly Gly Phe Arg Val Leu Asn His Tyr
    50                  55                  60

Ala Gly Glu Asp Ala Thr Glu Ala Phe Thr Ala Phe His Pro Asp Ile
65                  70                  75                  80

Lys Phe Val Gln Lys Tyr Met Lys Pro Leu Leu Val Gly Glu Leu Ala
                85                  90                  95
```

```
Ala Thr Glu Pro Ser Gln Asp Gln Asp Lys Asn Ala Ala Leu Ile Gln
            100                 105                 110

Asp Phe His Thr Leu Arg Gln Gln Ala Glu Ser Glu Gly Leu Phe Gln
            115                 120                 125

Ala Arg Pro Leu Phe Phe Leu Leu His Leu Gly His Ile Leu Leu Leu
        130                 135                 140

Glu Ala Leu Ala Leu Leu Met Val Trp His Trp Gly Thr Gly Trp Leu
145                 150                 155                 160

Gln Thr Leu Leu Cys Ala Val Met Leu Ala Thr Ala Gln Ser Gln Ala
                165                 170                 175

Gly Trp Leu Gln His Asp Phe Gly His Leu Ser Val Phe Lys Lys Ser
        180                 185                 190

Arg Trp Asn His Leu Val His Lys Phe Val Ile Gly His Leu Lys Gly
            195                 200                 205

Ala Ser Ala Asn Trp Trp Asn His Arg His Phe Gln His His Ala Lys
        210                 215                 220

Pro Asn Ile Phe Lys Lys Asp Pro Asp Ile Asn Met Val Asp Leu Phe
225                 230                 235                 240

Val Leu Gly Glu Thr Gln Pro Val Glu Tyr Gly Ile Lys Lys Ile Lys
                245                 250                 255

Asn Met Pro Tyr Asn His Gln His Lys Tyr Phe Phe Leu Val Ala Pro
            260                 265                 270

Pro Leu Leu Ile Pro Val Phe Phe Asn Tyr Asn Ile Met Met Thr Met
        275                 280                 285

Ile Thr Arg Arg Asp Tyr Val Asp Leu Ser Trp Ala Met Thr Phe Tyr
            290                 295                 300

Ile Arg Tyr Met Leu Cys Tyr Val Pro Val Tyr Gly Leu Phe Gly Ser
305                 310                 315                 320

Leu Ala Leu Met Met Phe Ala Arg Phe Leu Glu Ser His Trp Phe Val
                325                 330                 335

Trp Val Thr Gln Met Ser His Leu Pro Met Asp Ile Asp Asn Asp Lys
            340                 345                 350

Arg Arg Asp Trp Leu Ser Met Gln Leu Gln Ala Thr Cys Asn Ile Glu
        355                 360                 365

Lys Ser Phe Phe Asn Asp Trp Phe Ser Gly His Leu Asn Phe Gln Ile
    370                 375                 380

Glu His His Leu Phe Pro Arg Met Pro Arg His Asn Tyr His Leu Val
385                 390                 395                 400

Ala Pro Gln Val Gln Thr Leu Cys Glu Lys His Gly Ile Pro Tyr Glu
                405                 410                 415

Val Lys Thr Leu Trp Lys Gly Met Val Asp Val Val Arg Ala Leu Lys
            420                 425                 430

Lys Ser Gly Asp Leu Trp Leu Asp Ala Tyr Leu His Lys
        435                 440                 445

<210> SEQ ID NO 19
<211> LENGTH: 1338
<212> TYPE: DNA
<213> ORGANISM: Artificial
<220> FEATURE:
<223> OTHER INFORMATION: chimeric protein

<400> SEQUENCE: 19
atgggaggtg gaggtcagct gggggagtca ggggagaatg gctgcaagtc agctgctggt      60
```

```
gtgtacactt gggaggaggt gcagcaccac agcaacagga atgaccagtg gttggtcatt    120
gatcgcaagg tttataatgt cacccagtgg gccaagagac acccaggagg gtttcgggtc    180
ctcaaccact atgctggaga ggatgctacg gaggcattca ctgcttttca ccccgacata    240
aaatttgtac aaaagtatat gaagcctttg ctggtaggag agctggctgc aacgagcccc    300
agtcaggatc aagacaaaaa tgccgcactc atacaggatt ccacactttt acgtcagcaa    360
gcggagagtg agggtctgtt tcaagctcgc cctttgttct tcctccttca tttgggtcac    420
atcctgttgc tggaggctct ggcccttctg atggtctggc actggggaac gggctggcta    480
cagacgttac tatgtgccgt tatgctggca actgctcagt ctcaggccgg ctggcttcag    540
cacgactttg acacctgtc tgtcttcaag aaatcccgct ggaatcactt ggttcacaag    600
tttgtcatcg gccatttaaa gggagcttct gccaactggt ggaatcatcg tcatttccag    660
catcacgcta aacccaacat cttcaagaag gatcctgaca tcaacatggt ggacctttt    720 gtacttggag agactcaacc tgtggagtat ggcataaaga agattaaaaa tatgccctat    780
aaccaccagc acaagtattt cttttttggtt gcgccaccac ttcttattcc agttttcttc    840
cactataaca taatgatgac catgattact cgccgtgact atgtggatct gtcttgggcc    900
atgacgtttt acattcgcta catgttgtgc tatgtgccgg tctatggcct ttttggatca    960
ctggcgctca tgatgtttgc caggtttttg gagagccact ggttcgtgtg gtaactcag   1020 atgagtcatc tgcccatgga catcgacaat gacaaacgcc gtgactggct gtccatgcag   1080
ttacaagcca cctgtaacat tgagaagtct ttttcaacg actggttcag tggacacctc   1140
aacttccaaa ttgaacacca tttgttcccg aggatgccgc gccacaacta ccacctggtg   1200
gctccacagg tccagacact gtgtgagaaa catgggattc catacgaagt gaaaacgctg   1260
tggaaaggca tggttgacgt cgtcagggca ctgaaaaaat caggagacct ctggcttgat   1320
gcatatctcc ataaatga                                                1338

<210> SEQ ID NO 20
<211> LENGTH: 445
<212> TYPE: PRT
<213> ORGANISM: Artificial
<220> FEATURE:
<223> OTHER INFORMATION: chimeric primer

<400> SEQUENCE: 20

Met Gly Gly Gly Gly Gln Leu Gly Glu Ser Gly Glu Asn Gly Cys Lys
1               5                   10                  15

Ser Ala Ala Gly Val Tyr Thr Trp Glu Val Gln His His Ser Asn
            20                  25                  30

Arg Asn Asp Gln Trp Leu Val Ile Asp Arg Lys Val Tyr Asn Val Thr
        35                  40                  45

Gln Trp Ala Lys Arg His Pro Gly Gly Phe Arg Val Leu Asn His Tyr
    50                  55                  60

Ala Gly Glu Asp Ala Thr Glu Ala Phe Thr Ala Phe His Pro Asp Ile
65                  70                  75                  80

Lys Phe Val Gln Lys Tyr Met Lys Pro Leu Leu Val Gly Glu Leu Ala
                85                  90                  95

Ala Thr Glu Pro Ser Gln Asp Gln Asp Lys Asn Ala Ala Leu Ile Gln
            100                 105                 110

Asp Phe His Thr Leu Arg Gln Gln Ala Glu Ser Glu Gly Leu Phe Gln
        115                 120                 125

Ala Arg Pro Leu Phe Phe Leu Leu His Leu Gly His Ile Leu Leu Leu
```

```
                130                 135                 140
Glu Ala Leu Ala Leu Leu Met Val Trp His Trp Gly Thr Gly Trp Leu
145                 150                 155                 160

Gln Thr Leu Leu Cys Ala Val Met Leu Ala Thr Ala Gln Ser Gln Ala
                165                 170                 175

Gly Trp Leu Gln His Asp Phe Gly His Leu Ser Val Phe Lys Lys Ser
            180                 185                 190

Arg Trp Asn His Leu Val His Lys Phe Val Ile Gly His Leu Lys Gly
        195                 200                 205

Ala Ser Ala Asn Trp Trp Asn His Arg His Phe Gln His His Ala Lys
210                 215                 220

Pro Asn Ile Phe Lys Lys Asp Pro Asp Ile Asn Met Val Asp Leu Phe
225                 230                 235                 240

Val Leu Gly Glu Thr Gln Pro Val Glu Tyr Gly Ile Lys Lys Ile Lys
                245                 250                 255

Asn Met Pro Tyr Asn His Gln His Lys Tyr Phe Phe Leu Val Ala Pro
            260                 265                 270

Pro Leu Leu Ile Pro Val Phe Phe His Tyr Asn Ile Met Met Thr Met
        275                 280                 285

Ile Thr Arg Arg Asp Tyr Val Asp Leu Ser Trp Ala Met Thr Phe Tyr
290                 295                 300

Ile Arg Tyr Met Leu Cys Tyr Val Pro Val Tyr Gly Leu Phe Gly Ser
305                 310                 315                 320

Leu Ala Leu Met Met Phe Ala Arg Phe Leu Glu Ser His Trp Phe Val
                325                 330                 335

Trp Val Thr Gln Met Ser His Leu Pro Met Asp Ile Asp Asn Asp Lys
            340                 345                 350

Arg Arg Asp Trp Leu Ser Met Gln Leu Gln Ala Thr Cys Asn Ile Glu
        355                 360                 365

Lys Ser Phe Phe Asn Asp Trp Phe Ser Gly His Leu Asn Phe Gln Ile
370                 375                 380

Glu His His Leu Phe Pro Arg Met Pro Arg His Asn Tyr His Leu Val
385                 390                 395                 400

Ala Pro Gln Val Gln Thr Leu Cys Glu Lys His Gly Ile Pro Tyr Glu
                405                 410                 415

Val Lys Thr Leu Trp Lys Gly Met Val Asp Val Val Arg Ala Leu Lys
            420                 425                 430

Lys Ser Gly Asp Leu Trp Leu Asp Ala Tyr Leu His Lys
        435                 440                 445

<210> SEQ ID NO 21
<211> LENGTH: 1332
<212> TYPE: DNA
<213> ORGANISM: Artificial
<220> FEATURE:
<223> OTHER INFORMATION: chimeric protein

<400> SEQUENCE: 21
atgggaggtg gaggtcagcc gagggagtca ggggagcccg gcagcagtcc agctgtgtac    60
acctgggagg aggtgcagca ccactcttcc aggaatgacc agtggttggt gatcgatcga   120
aaagtttata acatctctca gtgggccaaa cggcacccag agggtaccg gtgattggc    180 cattatgctg gggaggatgc tacggaagca ttcactgctt ccaccctga cttgaaattt    240 gtgcaaaagt tcctcaagcc tttgctgata ggagagctgg cagccacaga gcccagccag   300
```

```
gaccgaaaca aaaatgccgc actcatacag gatttccaca ctttacgtca gcaagcggag    360
agtgagggtc tgtttcaagc tcgccctttg ttcttcctcc ttcatttggg tcacatcctg    420
ttgctggagg ctctggccct tctgatggtc tggcactggg gaacgggctg gctacagacg    480
ttactatgtg ccgttatgct ggcaactgct cagtctcagg ccggctggct tcagcacgac    540
tttggacacc tgtctgtctt caagaaatcc cgctggaatc acttggttca ccactttgtc    600
atcggccatt taagggagc ttctgccaac tggtggaatc atcgtcattt ccagcatcac    660
gctaaaccca acatcttcaa gaaggatcct gacatcaaca tggtggacct ttttgtactt    720
ggagagactc aacctgtgga gtatggcgta aagaagatca aattaatgcc ctacaaccac    780
cagcaccagt acttccatct cattggacca ccgcttctca ttccagtttt tttcaactac    840
cagttgctga aaatcatgat ttctcaccgc tactggctgg atctggtgtg gtgcttgtcc    900
ttctaccttc ggtacatgtg ctgctatgtg ccggtctacg gcctttttgg atctgtggta    960
ctcattgtat ttacaaggtt tttggagagc cactggttcg tgtgggtgac gcagatgaat   1020
catctgccga tggacatcaa ctatgagaac acaacgact ggctgtccat gcagttgcaa    1080
gccacctgta atgttgagca gtctctcttc aacgactggt tcagtggaca tctcaacttt   1140
caaatcgaac accattgtt tcccaccatg ccgcgccaca actaccacct ggtggttcca    1200
cgggtccgtg cactctgtga gaaacatgag ataccatacc aggtgaagac actgccgcag   1260
gccttcgctg atatcatcag gtcactgaaa aactcagggg agctctggct tgatgcatat   1320
ctccataaat ga                                                        1332
```

<210> SEQ ID NO 22
<211> LENGTH: 443
<212> TYPE: PRT
<213> ORGANISM: Artificial
<220> FEATURE:
<223> OTHER INFORMATION: chimeric protein

<400> SEQUENCE: 22

```
Met Gly Gly Gly Gly Gln Pro Arg Glu Ser Gly Glu Pro Gly Ser Ser
1               5                   10                  15

Pro Ala Val Tyr Thr Trp Glu Glu Val Gln His His Ser Ser Arg Asn
            20                  25                  30

Asp Gln Trp Leu Val Ile Asp Arg Lys Val Tyr Asn Ile Ser Gln Trp
        35                  40                  45

Ala Lys Arg His Pro Gly Gly Tyr Arg Val Ile Gly His Tyr Ala Gly
    50                  55                  60

Glu Asp Ala Thr Glu Ala Phe Thr Ala Phe His Pro Asp Leu Lys Phe
65                  70                  75                  80

Val Gln Lys Phe Leu Lys Pro Leu Leu Ile Gly Glu Leu Ala Ala Thr
                85                  90                  95

Glu Pro Ser Gln Asp Arg Asn Lys Asn Ala Ala Leu Ile Gln Asp Phe
            100                 105                 110

His Thr Leu Arg Gln Gln Ala Glu Ser Glu Gly Leu Phe Gln Ala Arg
        115                 120                 125

Pro Leu Phe Phe Leu Leu His Leu Gly His Ile Leu Leu Leu Glu Ala
    130                 135                 140

Leu Ala Leu Leu Met Val Trp His Trp Gly Thr Gly Trp Leu Gln Thr
145                 150                 155                 160

Leu Leu Cys Ala Val Met Leu Ala Thr Ala Gln Ser Gln Ala Gly Trp
                165                 170                 175
```

```
Leu Gln His Asp Phe Gly His Leu Ser Val Phe Lys Lys Ser Arg Trp
            180                 185                 190
Asn His Leu Val His His Phe Val Ile Gly His Leu Lys Gly Ala Ser
        195                 200                 205
Ala Asn Trp Trp Asn His Arg His Phe Gln His Ala Lys Pro Asn
    210                 215                 220
Ile Phe Lys Lys Asp Pro Asp Ile Asn Met Val Asp Leu Phe Val Leu
225                 230                 235                 240
Gly Glu Thr Gln Pro Val Glu Tyr Gly Val Lys Lys Ile Lys Leu Met
                245                 250                 255
Pro Tyr Asn His Gln His Gln Tyr Phe His Leu Ile Gly Pro Pro Leu
            260                 265                 270
Leu Ile Pro Val Phe Phe Asn Tyr Gln Leu Leu Lys Ile Met Ile Ser
        275                 280                 285
His Arg Tyr Trp Leu Asp Leu Val Trp Cys Leu Ser Phe Tyr Leu Arg
    290                 295                 300
Tyr Met Cys Cys Tyr Val Pro Val Tyr Gly Leu Phe Gly Ser Val Val
305                 310                 315                 320
Leu Ile Val Phe Thr Arg Phe Leu Glu Ser His Trp Phe Val Trp Val
                325                 330                 335
Thr Gln Met Asn His Leu Pro Met Asp Ile Asn Tyr Glu Asn His Asn
            340                 345                 350
Asp Trp Leu Ser Met Gln Leu Gln Ala Thr Cys Asn Val Glu Gln Ser
        355                 360                 365
Leu Phe Asn Asp Trp Phe Ser Gly His Leu Asn Phe Gln Ile Glu His
    370                 375                 380
His Leu Phe Pro Thr Met Pro Arg His Asn Tyr His Leu Val Val Pro
385                 390                 395                 400
Arg Val Arg Ala Leu Cys Glu Lys His Glu Ile Pro Tyr Gln Val Lys
                405                 410                 415
Thr Leu Pro Gln Ala Phe Ala Asp Ile Ile Arg Ser Leu Lys Asn Ser
            420                 425                 430
Gly Glu Leu Trp Leu Asp Ala Tyr Leu His Lys
        435                 440
```

<210> SEQ ID NO 23
<211> LENGTH: 1332
<212> TYPE: DNA
<213> ORGANISM: Artificial
<220> FEATURE:
<223> OTHER INFORMATION: chimeric protein

<400> SEQUENCE: 23

```
atgggaggtg aggtcagcc gagggagtca ggggagcccg gcagcagtcc agctgtgtac      60
acctgggagg aggtgcagca ccactcttcc aggaatgacc agtggttggt gatcgatcga     120
aaagtttata acatctctca gtgggccaaa cggcacccag agggtaccg ggtgattggc      180
cattatgctg gggaggatgc tacggaagca ttcactgctt ccaccctga cttgaaattt      240
gtgcaaaagt tcctcaagcc tttgctgata ggagagctgg cagccacaga gcccagccag     300
gaccgaaaca aaaatgccgc actcatacag gatttccaca ctttacgtca gcaagcggag     360
agtgagggtc tgtttcaagc tcgcccttg ttcttcctcc ttcatttggg tcacatcctg      420
ttgctggagg ctctggccct tctgatggtc tggcactggg aacgggctg gctacagacg      480
ttactatgtg ccgttatgct ggcaactgct cagtctcagg ccggctggct tcagcacgac     540
```

```
tttggacacc tgtctgtctt caagaaatcc cgctggaatc acttggttca ccactttgtc    600
atcggccatt taaagggagc ttctgccaac tggtggaatc atcgtcattt ccagcatcac    660
gctaaaccca acatcttcaa gaaggatcct gacatcaaca tggtggacct ttttgtactt    720
ggagagactc aacctgtgga gtatggcgta aagaagatca aattaatgcc ctacaaccac    780
cagcaccagt acttccatct cattggacca ccgcttctca ttccagtttt ttaccactac    840
cagttgctga aaatcatgat ttctcaccgc tactggctgg atctggtgtg gtgcttgtcc    900
ttctaccttc ggtacatgtg ctgctatgtg ccggtctacg gcttttttgg atctgtggta    960
ctcattgtat ttacaaggtt tttggagagc cactggttcg tgtgggtgac gcagatgaat   1020
catctgccga tggacatcaa ctatgagaac cacaacgact ggctgtccat gcagttgcaa   1080
gccacctgta atgttgagca gtctctcttc aacgactggt tcagtggaca tctcaacttt   1140
caaatcgaac accatttgtt tcccaccatg ccgcgccaca actaccacct ggtggttcca   1200
cgggtccgtg cactctgtga gaaacatgag ataccatacc aggtgaagac actgccgcag   1260
gccttcgctg atatcatcag gtcactgaaa aactcagggg agctctggct tgatgcatat   1320
ctccataaat ga                                                         1332
```

<210> SEQ ID NO 24
<211> LENGTH: 443
<212> TYPE: PRT
<213> ORGANISM: Artificial
<220> FEATURE:
<223> OTHER INFORMATION: chimeric protein

<400> SEQUENCE: 24

```
Met Gly Gly Gly Gln Pro Arg Glu Ser Gly Glu Pro Gly Ser Ser
1               5                   10                  15

Pro Ala Val Tyr Thr Trp Glu Glu Val Gln His His Ser Ser Arg Asn
            20                  25                  30

Asp Gln Trp Leu Val Ile Asp Arg Lys Val Tyr Asn Ile Ser Gln Trp
        35                  40                  45

Ala Lys Arg His Pro Gly Gly Tyr Arg Val Ile Gly His Tyr Ala Gly
    50                  55                  60

Glu Asp Ala Thr Glu Ala Phe Thr Ala Phe His Pro Asp Leu Lys Phe
65                  70                  75                  80

Val Gln Lys Phe Leu Lys Pro Leu Leu Ile Gly Glu Leu Ala Ala Thr
                85                  90                  95

Glu Pro Ser Gln Asp Arg Asn Lys Asn Ala Ala Leu Ile Gln Asp Phe
            100                 105                 110

His Thr Leu Arg Gln Gln Ala Glu Ser Glu Gly Leu Phe Gln Ala Arg
        115                 120                 125

Pro Leu Phe Phe Leu Leu His Leu Gly His Ile Leu Leu Leu Glu Ala
    130                 135                 140

Leu Ala Leu Leu Met Val Trp His Trp Gly Thr Gly Trp Leu Gln Thr
145                 150                 155                 160

Leu Leu Cys Ala Val Met Leu Ala Thr Ala Gln Ser Gln Ala Gly Trp
                165                 170                 175

Leu Gln His Asp Phe Gly His Leu Ser Val Phe Lys Lys Ser Arg Trp
            180                 185                 190

Asn His Leu Val His His Phe Val Ile Gly His Leu Lys Gly Ala Ser
        195                 200                 205

Ala Asn Trp Trp Asn His Arg His Phe Gln His His Ala Lys Pro Asn
    210                 215                 220
```

```
Ile Phe Lys Lys Asp Pro Asp Ile Asn Met Val Asp Leu Phe Val Leu
225                 230                 235                 240

Gly Glu Thr Gln Pro Val Glu Tyr Gly Val Lys Lys Ile Lys Leu Met
            245                 250                 255

Pro Tyr Asn His Gln His Gln Tyr Phe His Leu Ile Gly Pro Pro Leu
        260                 265                 270

Leu Ile Pro Val Phe Tyr His Tyr Gln Leu Leu Lys Ile Met Ile Ser
    275                 280                 285

His Arg Tyr Trp Leu Asp Leu Val Trp Cys Leu Ser Phe Tyr Leu Arg
290                 295                 300

Tyr Met Cys Cys Tyr Val Pro Val Tyr Gly Leu Phe Gly Ser Val Val
305                 310                 315                 320

Leu Ile Val Phe Thr Arg Phe Leu Glu Ser His Trp Phe Val Trp Val
                325                 330                 335

Thr Gln Met Asn His Leu Pro Met Asp Ile Asn Tyr Glu Asn His Asn
            340                 345                 350

Asp Trp Leu Ser Met Gln Leu Gln Ala Thr Cys Asn Val Glu Gln Ser
        355                 360                 365

Leu Phe Asn Asp Trp Phe Ser Gly His Leu Asn Phe Gln Ile Glu His
    370                 375                 380

His Leu Phe Pro Thr Met Pro Arg His Asn Tyr His Leu Val Val Pro
385                 390                 395                 400

Arg Val Arg Ala Leu Cys Glu Lys His Glu Ile Pro Tyr Gln Val Lys
                405                 410                 415

Thr Leu Pro Gln Ala Phe Ala Asp Ile Ile Arg Ser Leu Lys Asn Ser
            420                 425                 430

Gly Glu Leu Trp Leu Asp Ala Tyr Leu His Lys
        435                 440

<210> SEQ ID NO 25
<211> LENGTH: 1332
<212> TYPE: DNA
<213> ORGANISM: Artificial
<220> FEATURE:
<223> OTHER INFORMATION: chimeric protein

<400> SEQUENCE: 25 atggaggtg gaggtcagcc gagggagtca ggggagcccg gcagcagtcc agctgtgtac      60
acctgggagg aggtgcagca ccactcttcc aggaatgacc agtggttggt gatcgatcga     120
aaagtttata acatctctca gtgggccaaa cggcacccag agggtaccg ggtgattggc      180 cattatgctg ggaggatgc tacggaagca ttcactgctt ccaccctga cttgaaattt      240 gtgcaaaagt tcctcaagcc tttgctgata ggagagctgg cagccacaga gcccagccag     300
gaccgaaaca aaaatgccgc actcatacag gatttccaca ctttacgtca gcaagcggag     360
agtgagggtc tgtttcaagc tcgcccttg ttcttcctcc ttcatttggg tcacatcctg      420
ttgctggagg ctctggccct tctgatggtc tggcactggg aacgggctg ctacagacg      480 ttactatgtg ccgttatgct ggcaactgct cagtctcagg ccggctggct tcagcacgac     540
tttggacacc tgtctgtctt caagaaatcc cgctggaatc acttggttca ccactttgtc     600
atcggccatt taagggagc ttctgccaac tggtggaatc atcgtcattt ccagcatcac      660
gctaaaccca acatcttcaa gaaggatcct gacatcaaca tggtggacct ttttgtactt     720
ggagagactc aacctgtgga gtatggcgta aagaagatca aattaatgcc ctacaaccac     780
```

```
cagcaccagt acttccatct cattggacca ccgcttctca ttccagtttt ttacaactac    840
cagttgctga aaatcatgat ttctcaccgc tactggctgg atctggtgtg gtgcttgtcc    900
ttctaccttc ggtacatgtg ctgctatgtg ccggtctacg gccttttttgg atctgtggta   960 ctcattgtat ttacaaggtt tttggagagc cactggttcg tgtgggtgac gcagatgaat   1020
catctgccga tggacatcaa ctatgagaac cacaacgact ggctgtccat gcagttgcaa   1080
gccacctgta atgttgagca gtctctcttc aacgactggt tcagtggaca tctcaacttt   1140
caaatcgaac accatttgtt tcccaccatg ccgcgccaca actaccacct ggtggttcca   1200
cgggtccgtg cactctgtga aaacatgag ataccatacc aggtgaagac actgccgcag    1260
gccttcgctg atatcatcag gtcactgaaa aactcagggg agctctggct tgatgcatat   1320
ctccataaat ga                                                        1332
```

<210> SEQ ID NO 26
<211> LENGTH: 443
<212> TYPE: PRT
<213> ORGANISM: Artificial
<220> FEATURE:
<223> OTHER INFORMATION: chimeric protein

<400> SEQUENCE: 26

```
Met Gly Gly Gly Gly Gln Pro Arg Glu Ser Gly Glu Pro Gly Ser Ser
1               5                   10                  15

Pro Ala Val Tyr Thr Trp Glu Glu Val Gln His Ser Ser Arg Asn
            20                  25                  30

Asp Gln Trp Leu Val Ile Asp Arg Lys Val Tyr Asn Ile Ser Gln Trp
        35                  40                  45

Ala Lys Arg His Pro Gly Gly Tyr Arg Val Ile Gly His Tyr Ala Gly
    50                  55                  60

Glu Asp Ala Thr Glu Ala Phe Thr Ala Phe His Pro Asp Leu Lys Phe
65                  70                  75                  80

Val Gln Lys Phe Leu Lys Pro Leu Leu Ile Gly Glu Leu Ala Ala Thr
                85                  90                  95

Glu Pro Ser Gln Asp Arg Asn Lys Asn Ala Ala Leu Ile Gln Asp Phe
            100                 105                 110

His Thr Leu Arg Gln Gln Ala Glu Ser Glu Gly Leu Phe Gln Ala Arg
        115                 120                 125

Pro Leu Phe Phe Leu Leu His Leu Gly His Ile Leu Leu Leu Glu Ala
    130                 135                 140

Leu Ala Leu Leu Met Val Trp His Trp Gly Thr Gly Trp Leu Gln Thr
145                 150                 155                 160

Leu Leu Cys Ala Val Met Leu Ala Thr Ala Gln Ser Gln Ala Gly Trp
                165                 170                 175

Leu Gln His Asp Phe Gly His Leu Ser Val Phe Lys Lys Ser Arg Trp
            180                 185                 190

Asn His Leu Val His His Phe Val Ile Gly His Leu Lys Gly Ala Ser
        195                 200                 205

Ala Asn Trp Trp Asn His Arg His Phe Gln His His Ala Lys Pro Asn
    210                 215                 220

Ile Phe Lys Lys Asp Pro Asp Ile Asn Met Val Asp Leu Phe Val Leu
225                 230                 235                 240

Gly Glu Thr Gln Pro Val Glu Tyr Gly Val Lys Lys Ile Lys Leu Met
                245                 250                 255

Pro Tyr Asn His Gln His Gln Tyr Phe His Leu Ile Gly Pro Pro Leu
```

-continued

```
                260                 265                 270
Leu Ile Pro Val Phe Tyr Asn Tyr Gln Leu Leu Lys Ile Met Ile Ser
            275                 280                 285
His Arg Tyr Trp Leu Asp Leu Val Trp Cys Leu Ser Phe Tyr Leu Arg
        290                 295                 300
Tyr Met Cys Cys Tyr Val Pro Val Tyr Gly Leu Phe Gly Ser Val Val
305                 310                 315                 320
Leu Ile Val Phe Thr Arg Phe Leu Glu Ser His Trp Phe Val Trp Val
                325                 330                 335
Thr Gln Met Asn His Leu Pro Met Asp Ile Asn Tyr Glu Asn His Asn
            340                 345                 350
Asp Trp Leu Ser Met Gln Leu Gln Ala Thr Cys Asn Val Glu Gln Ser
        355                 360                 365
Leu Phe Asn Asp Trp Phe Ser Gly His Leu Asn Phe Gln Ile Glu His
    370                 375                 380
His Leu Phe Pro Thr Met Pro Arg His Asn Tyr His Leu Val Val Pro
385                 390                 395                 400
Arg Val Arg Ala Leu Cys Glu Lys His Glu Ile Pro Tyr Gln Val Lys
                405                 410                 415
Thr Leu Pro Gln Ala Phe Ala Asp Ile Ile Arg Ser Leu Lys Asn Ser
            420                 425                 430
Gly Glu Leu Trp Leu Asp Ala Tyr Leu His Lys
        435                 440

<210> SEQ ID NO 27
<211> LENGTH: 21
<212> TYPE: DNA
<213> ORGANISM: Artificial
<220> FEATURE:
<223> OTHER INFORMATION: primer

<400> SEQUENCE: 27
agtgaagatg ggaggtggag g                                            21

<210> SEQ ID NO 28
<211> LENGTH: 29
<212> TYPE: DNA
<213> ORGANISM: Artificial
<220> FEATURE:
<223> OTHER INFORMATION: primer

<400> SEQUENCE: 28
atagagttca tttatggaga tatgcatca                                    29

<210> SEQ ID NO 29
<211> LENGTH: 21
<212> TYPE: DNA
<213> ORGANISM: Artificial
<220> FEATURE:
<223> OTHER INFORMATION: primer

<400> SEQUENCE: 29
gtgaggatgg gaggtggagg t                                            21

<210> SEQ ID NO 30
<211> LENGTH: 26
<212> TYPE: DNA
<213> ORGANISM: Artificial
<220> FEATURE:
<223> OTHER INFORMATION: primer
```

```
<400> SEQUENCE: 30
ggtcatttat ggagatatgc atcaag                                  26

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
cttctcattc cagttttcta caactataac                              30

<210> SEQ ID NO 32
<211> LENGTH: 25
<212> TYPE: DNA
<213> ORGANISM: Artificial
<220> FEATURE:
<223> OTHER INFORMATION: primer

<400> SEQUENCE: 32
aaaaactgga ataagaagtg gtggc                                   25

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
cttcttattc cagttttttt ccactaccag                              30

<210> SEQ ID NO 34
<211> LENGTH: 24
<212> TYPE: DNA
<213> ORGANISM: Artificial
<220> FEATURE:
<223> OTHER INFORMATION: primer

<400> SEQUENCE: 34
gaaaactgga atgagaagcg gtgg                                    24

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
gccggtctac ggccttttg                                          20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
caaaaaggcc gtagaccggc                                         20

<210> SEQ ID NO 37
<211> LENGTH: 18
```

```
<212> TYPE: DNA
<213> ORGANISM: Artificial
<220> FEATURE:
<223> OTHER INFORMATION: primer

<400> SEQUENCE: 37
atgccgcgcc acaactac                                                       18

<210> SEQ ID NO 38
<211> LENGTH: 18
<212> TYPE: DNA
<213> ORGANISM: Artificial
<220> FEATURE:
<223> OTHER INFORMATION: primer

<400> SEQUENCE: 38
gtagttgtgg cgcggcat                                                       18

<210> SEQ ID NO 39
<211> LENGTH: 27
<212> TYPE: DNA
<213> ORGANISM: Artificial
<220> FEATURE:
<223> OTHER INFORMATION: primer

<400> SEQUENCE: 39
ctgtcttggt gcttgtcctt ctacctt                                             27

<210> SEQ ID NO 40
<211> LENGTH: 25
<212> TYPE: DNA
<213> ORGANISM: Artificial
<220> FEATURE:
<223> OTHER INFORMATION: primer

<400> SEQUENCE: 40
caagcaccaa gacagatcca catag                                               25

<210> SEQ ID NO 41
<211> LENGTH: 25
<212> TYPE: DNA
<213> ORGANISM: Artificial
<220> FEATURE:
<223> OTHER INFORMATION: primer

<400> SEQUENCE: 41
ctggtgtggg ccatgacgtt ttaca                                               25

<210> SEQ ID NO 42
<211> LENGTH: 25
<212> TYPE: DNA
<213> ORGANISM: Artificial
<220> FEATURE:
<223> OTHER INFORMATION: primer

<400> SEQUENCE: 42
catggcccac accagatcca gccag                                               25

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
```
ttccagtttt ctacaactat aacataatga                                           30

<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44
tcattatgtt atagttgtag aaaactggaa                                           30

<210> SEQ ID NO 45
<211> LENGTH: 25
<212> TYPE: DNA
<213> ORGANISM: Artificial
<220> FEATURE:
<223> OTHER INFORMATION: primer

<400> SEQUENCE: 45
attccagttt ttttccacta ccagt                                                25

<210> SEQ ID NO 46
<211> LENGTH: 25
<212> TYPE: DNA
<213> ORGANISM: Artificial
<220> FEATURE:
<223> OTHER INFORMATION: primer

<400> SEQUENCE: 46
actggtagtg gaaaaaaact ggaat                                                25

<210> SEQ ID NO 47
<211> LENGTH: 25
<212> TYPE: DNA
<213> ORGANISM: Artificial
<220> FEATURE:
<223> OTHER INFORMATION: primer

<400> SEQUENCE: 47
aaatcatgat tactcgccgt gacta                                                25

<210> SEQ ID NO 48
<211> LENGTH: 26
<212> TYPE: DNA
<213> ORGANISM: Artificial
<220> FEATURE:
<223> OTHER INFORMATION: primer

<400> SEQUENCE: 48
gagtaatcat gattttcagc aactgg                                               26

<210> SEQ ID NO 49
<211> LENGTH: 21
<212> TYPE: DNA
<213> ORGANISM: Artificial
<220> FEATURE:
<223> OTHER INFORMATION: primer

<400> SEQUENCE: 49
catgatttct caccgctact g                                                    21

<210> SEQ ID NO 50
<211> LENGTH: 33
<212> TYPE: DNA
<213> ORGANISM: Artificial

```
<220> FEATURE:
<223> OTHER INFORMATION: primer

<400> SEQUENCE: 50
cggtgagaaa tcatggtcat cattatgtta tag                            33

<210> SEQ ID NO 51
<211> LENGTH: 30
<212> TYPE: DNA
<213> ORGANISM: Artificial
<220> FEATURE:
<223> OTHER INFORMATION: primer

<400> SEQUENCE: 51
ttccactacc agataatgat gaccatgatt                                30

<210> SEQ ID NO 52
<211> LENGTH: 31
<212> TYPE: DNA
<213> ORGANISM: Artificial
<220> FEATURE:
<223> OTHER INFORMATION: primer

<400> SEQUENCE: 52
gtcatcatta tctggtagtg gaaaaaaact g                              31

<210> SEQ ID NO 53
<211> LENGTH: 27
<212> TYPE: DNA
<213> ORGANISM: Artificial
<220> FEATURE:
<223> OTHER INFORMATION: primer

<400> SEQUENCE: 53
aactataact tgctgaaaat catgatt                                   27

<210> SEQ ID NO 54
<211> LENGTH: 32
<212> TYPE: DNA
<213> ORGANISM: Artificial
<220> FEATURE:
<223> OTHER INFORMATION: primer

<400> SEQUENCE: 54
ttttcagcaa gttatagttg tagaaaactg ga                             32

<210> SEQ ID NO 55
<211> LENGTH: 30
<212> TYPE: DNA
<213> ORGANISM: Artificial
<220> FEATURE:
<223> OTHER INFORMATION: primer

<400> SEQUENCE: 55
ccagttttct acaactatca gataatgatg                                30

<210> SEQ ID NO 56
<211> LENGTH: 30
<212> TYPE: DNA
<213> ORGANISM: Artificial
<220> FEATURE:
<223> OTHER INFORMATION: primer

<400> SEQUENCE: 56
catcattatc tgatagttgt agaaaactgg                                30
```

```
<210> SEQ ID NO 57
<211> LENGTH: 27
<212> TYPE: DNA
<213> ORGANISM: Artificial
<220> FEATURE:
<223> OTHER INFORMATION: primer

<400> SEQUENCE: 57
tttccactac aacttgctga aaatcat                                          27

<210> SEQ ID NO 58
<211> LENGTH: 27
<212> TYPE: DNA
<213> ORGANISM: Artificial
<220> FEATURE:
<223> OTHER INFORMATION: primer

<400> SEQUENCE: 58
atgattttca gcaagttgta gtggaaa                                          27

<210> SEQ ID NO 59
<211> LENGTH: 27
<212> TYPE: DNA
<213> ORGANISM: Artificial
<220> FEATURE:
<223> OTHER INFORMATION: primer

<400> SEQUENCE: 59
tccagttttc taccactata acataat                                          27

<210> SEQ ID NO 60
<211> LENGTH: 27
<212> TYPE: DNA
<213> ORGANISM: Artificial
<220> FEATURE:
<223> OTHER INFORMATION: primer

<400> SEQUENCE: 60
tccagttttc taccactata acataat                                          27

<210> SEQ ID NO 61
<211> LENGTH: 23
<212> TYPE: DNA
<213> ORGANISM: Artificial
<220> FEATURE:
<223> OTHER INFORMATION: primer

<400> SEQUENCE: 61
gtttttttca actaccagtt gct                                              23

<210> SEQ ID NO 62
<211> LENGTH: 22
<212> TYPE: DNA
<213> ORGANISM: Artificial
<220> FEATURE:
<223> OTHER INFORMATION: primer

<400> SEQUENCE: 62
agcaactggt agttgaaaaa aa                                               22

<210> SEQ ID NO 63
<211> LENGTH: 30
<212> TYPE: DNA
<213> ORGANISM: Artificial
<220> FEATURE:
<223> OTHER INFORMATION: primer
```

```
<400> SEQUENCE: 63
ttccagtttt cttcaactat aacataatga                                    30

<210> SEQ ID NO 64
<211> LENGTH: 30
<212> TYPE: DNA
<213> ORGANISM: Artificial
<220> FEATURE:
<223> OTHER INFORMATION: primer

<400> SEQUENCE: 64
tcattatgtt atagttgaag aaaactggaa                                    30

<210> SEQ ID NO 65
<211> LENGTH: 26
<212> TYPE: DNA
<213> ORGANISM: Artificial
<220> FEATURE:
<223> OTHER INFORMATION: primer

<400> SEQUENCE: 65 ccagttttt accactacca gttgct                                         26

<210> SEQ ID NO 66
<211> LENGTH: 26
<212> TYPE: DNA
<213> ORGANISM: Artificial
<220> FEATURE:
<223> OTHER INFORMATION: primer

<400> SEQUENCE: 66
agcaactggt agtggtaaaa aactgg                                        26

<210> SEQ ID NO 67
<211> LENGTH: 27
<212> TYPE: DNA
<213> ORGANISM: Artificial
<220> FEATURE:
<223> OTHER INFORMATION: primer

<400> SEQUENCE: 67
ccagttttct tccactataa cataatg                                       27

<210> SEQ ID NO 68
<211> LENGTH: 27
<212> TYPE: DNA
<213> ORGANISM: Artificial
<220> FEATURE:
<223> OTHER INFORMATION: primer

<400> SEQUENCE: 68
cattatgtta tagtggaaga aaactgg                                       27

<210> SEQ ID NO 69
<211> LENGTH: 25
<212> TYPE: DNA
<213> ORGANISM: Artificial
<220> FEATURE:
<223> OTHER INFORMATION: primer

<400> SEQUENCE: 69 ccagttttt acaactacca gttgc                                          25

<210> SEQ ID NO 70
```

```
<211> LENGTH: 25
<212> TYPE: DNA
<213> ORGANISM: Artificial
<220> FEATURE:
<223> OTHER INFORMATION: primer

<400> SEQUENCE: 70
gcaactggta gttgtaaaaa actgg                                             25

<210> SEQ ID NO 71
<211> LENGTH: 7
<212> TYPE: PRT
<213> ORGANISM: Ostreococcus tauri

<400> SEQUENCE: 71

Phe Trp Met Phe Phe Leu His
1               5

<210> SEQ ID NO 72
<211> LENGTH: 7
<212> TYPE: PRT
<213> ORGANISM: Pavlova lutherii, salina

<400> SEQUENCE: 72

Phe Lys Leu Leu Phe Leu Asp
1               5

<210> SEQ ID NO 73
<211> LENGTH: 16
<212> TYPE: PRT
<213> ORGANISM: Ostreococcus tauri

<400> SEQUENCE: 73

Val Leu Leu Phe Trp Met Phe Phe Leu His Pro Ser Lys Ala Leu Lys
1               5                   10                  15

<210> SEQ ID NO 74
<211> LENGTH: 16
<212> TYPE: PRT
<213> ORGANISM: Artificial
<220> FEATURE:
<223> OTHER INFORMATION: mutated sequence

<400> SEQUENCE: 74

Val Leu Leu Phe Lys Leu Leu Phe Leu His Pro Ser Lys Ala Leu Lys
1               5                   10                  15

<210> SEQ ID NO 75
<211> LENGTH: 16
<212> TYPE: PRT
<213> ORGANISM: Artificial
<220> FEATURE:
<223> OTHER INFORMATION: mutated sequence

<400> SEQUENCE: 75

Val Leu Leu Phe Lys Leu Leu Phe Leu Asp Pro Ser Lys Ala Leu Lys
1               5                   10                  15

<210> SEQ ID NO 76
<211> LENGTH: 16
<212> TYPE: PRT
<213> ORGANISM: Artificial
<220> FEATURE:
<223> OTHER INFORMATION: mutated sequence

<400> SEQUENCE: 76
```

Val Leu Leu Phe Lys Leu Phe Phe Leu His Pro Ser Lys Ala Leu Lys
1               5                   10                  15

<210> SEQ ID NO 77
<211> LENGTH: 16
<212> TYPE: PRT
<213> ORGANISM: Artificial
<220> FEATURE:
<223> OTHER INFORMATION: mutated sequence

<400> SEQUENCE: 77

Val Leu Leu Phe Lys Leu Phe Phe Leu Asp Pro Ser Lys Ala Leu Lys
1               5                   10                  15

<210> SEQ ID NO 78
<211> LENGTH: 16
<212> TYPE: PRT
<213> ORGANISM: Artificial
<220> FEATURE:
<223> OTHER INFORMATION: mutated sequence

<400> SEQUENCE: 78

Val Leu Leu Phe Lys Met Leu Phe Leu His Pro Ser Lys Ala Leu Lys
1               5                   10                  15

<210> SEQ ID NO 79
<211> LENGTH: 16
<212> TYPE: PRT
<213> ORGANISM: Artificial
<220> FEATURE:
<223> OTHER INFORMATION: mutated sequence

<400> SEQUENCE: 79

Val Leu Leu Phe Lys Met Leu Phe Leu Asp Pro Ser Lys Ala Leu Lys
1               5                   10                  15

<210> SEQ ID NO 80
<211> LENGTH: 16
<212> TYPE: PRT
<213> ORGANISM: Artificial
<220> FEATURE:
<223> OTHER INFORMATION: mutated sequence

<400> SEQUENCE: 80

Val Leu Leu Phe Trp Leu Phe Phe Leu His Pro Ser Lys Ala Leu Lys
1               5                   10                  15

<210> SEQ ID NO 81
<211> LENGTH: 16
<212> TYPE: PRT
<213> ORGANISM: Artificial
<220> FEATURE:
<223> OTHER INFORMATION: mutated sequence

<400> SEQUENCE: 81

Val Leu Leu Phe Trp Leu Phe Phe Leu Asp Pro Ser Lys Ala Leu Lys
1               5                   10                  15

<210> SEQ ID NO 82
<211> LENGTH: 16
<212> TYPE: PRT
<213> ORGANISM: Artificial
<220> FEATURE:
<223> OTHER INFORMATION: mutated sequence

<400> SEQUENCE: 82

Val Leu Leu Phe Trp Met Leu Phe Leu His Pro Ser Lys Ala Leu Lys

<210> SEQ ID NO 83
<211> LENGTH: 16
<212> TYPE: PRT
<213> ORGANISM: Artificial
<220> FEATURE:
<223> OTHER INFORMATION: mutated sequence

<400> SEQUENCE: 83

Val Leu Leu Phe Trp Met Leu Phe Leu Asp Pro Ser Lys Ala Leu Lys
1               5                   10                  15

<210> SEQ ID NO 84
<211> LENGTH: 16
<212> TYPE: PRT
<213> ORGANISM: Artificial
<220> FEATURE:
<223> OTHER INFORMATION: mutated sequence

<400> SEQUENCE: 84

Val Leu Leu Phe Trp Leu Leu Phe Leu His Pro Ser Lys Ala Leu Lys
1               5                   10                  15

<210> SEQ ID NO 85
<211> LENGTH: 16
<212> TYPE: PRT
<213> ORGANISM: Artificial
<220> FEATURE:
<223> OTHER INFORMATION: mutated sequence

<400> SEQUENCE: 85

Val Leu Leu Phe Trp Leu Leu Phe Leu Asp Pro Ser Lys Ala Leu Lys
1               5                   10                  15

<210> SEQ ID NO 86
<211> LENGTH: 16
<212> TYPE: PRT
<213> ORGANISM: Artificial
<220> FEATURE:
<223> OTHER INFORMATION: mutated sequence

<400> SEQUENCE: 86

Val Leu Leu Phe Lys Met Phe Phe Leu His Pro Ser Lys Ala Leu Lys
1               5                   10                  15

<210> SEQ ID NO 87
<211> LENGTH: 16
<212> TYPE: PRT
<213> ORGANISM: Artificial
<220> FEATURE:
<223> OTHER INFORMATION: mutated sequence

<400> SEQUENCE: 87

Val Leu Leu Phe Trp Met Phe Phe Leu Asp Pro Ser Lys Ala Leu Lys
1               5                   10                  15

<210> SEQ ID NO 88
<211> LENGTH: 21
<212> TYPE: PRT
<213> ORGANISM: Ostreococcus tauri

<400> SEQUENCE: 88

Leu Val Trp Met Leu Ala Ala His Val Ile Arg Thr Trp Thr Ile Lys
1               5                   10                  15

Ala Val Thr Gly Phe

-continued

```
<210> SEQ ID NO 89
<211> LENGTH: 19
<212> TYPE: PRT
<213> ORGANISM: Pavlova lutherii

<400> SEQUENCE: 89

Val Ala Cys Lys Leu Gly Phe Trp Ala Arg Phe Val Ala Leu Pro Leu
1               5                   10                  15

Trp Leu Gln

<210> SEQ ID NO 90
<211> LENGTH: 20
<212> TYPE: PRT
<213> ORGANISM: Siganus artica

<400> SEQUENCE: 90

Ala Ile Gly Leu Arg Val Phe Phe Ile Arg Lys Phe Val Val Pro
1               5                   10                  15

Phe Ala Leu His
            20

<210> SEQ ID NO 91
<211> LENGTH: 19
<212> TYPE: PRT
<213> ORGANISM: Pavlova salina

<400> SEQUENCE: 91

Leu Leu Leu Lys Leu Thr Phe Trp Ala Arg Phe Val Ala Leu Pro Leu
1               5                   10                  15

Tyr Leu Ala

<210> SEQ ID NO 92
<211> LENGTH: 21
<212> TYPE: PRT
<213> ORGANISM: Pavlova lutherii

<400> SEQUENCE: 92

Arg Ala Leu Phe Ala Pro Ala Val Ala Cys Lys Leu Gly Phe Trp Ala
1               5                   10                  15

Arg Phe Val Ala Leu
            20

<210> SEQ ID NO 93
<211> LENGTH: 21
<212> TYPE: PRT
<213> ORGANISM: Pavlova salina

<400> SEQUENCE: 93

Leu Leu Leu Lys Leu Thr Phe Trp Ala Arg Phe Val Ala Leu Pro Leu
1               5                   10                  15

Tyr Leu Ala Pro Ser
            20

<210> SEQ ID NO 94
<211> LENGTH: 21
<212> TYPE: PRT
<213> ORGANISM: Siganus arctica

<400> SEQUENCE: 94

Leu Arg Val Phe Phe Phe Ile Arg Lys Phe Val Val Pro Phe Ala Leu
```

```
1               5                   10                  15

His Phe Ser Trp Tyr
            20

<210> SEQ ID NO 95
<211> LENGTH: 44
<212> TYPE: PRT
<213> ORGANISM: Ostreococcus tauri

<400> SEQUENCE: 95

Val Leu Leu Phe Trp Met Phe Phe Leu His Pro Ser Lys Ala Leu Lys
1               5                   10                  15

Gly Gly Lys Tyr Glu Glu Leu Val Trp Met Leu Ala Ala His Val Ile
            20                  25                  30

Arg Thr Trp Thr Ile Lys Ala Val Thr Gly Phe Thr
            35                  40

<210> SEQ ID NO 96
<211> LENGTH: 43
<212> TYPE: PRT
<213> ORGANISM: Pavlova lutherii

<400> SEQUENCE: 96

Glu Leu Leu Ala Trp Arg Trp Glu Gly Glu Lys Ile Ser Pro Leu Ala
1               5                   10                  15

Arg Ala Leu Phe Ala Pro Ala Val Ala Cys Lys Leu Gly Phe Trp Ala
            20                  25                  30

Arg Phe Val Ala Leu Pro Leu Trp Leu Gln Pro
            35                  40

<210> SEQ ID NO 97
<211> LENGTH: 43
<212> TYPE: PRT
<213> ORGANISM: Pavlova salina

<400> SEQUENCE: 97

Glu Leu Val Met Trp Arg Trp Glu Gly Glu Pro Ile Ser Lys Leu Ala
1               5                   10                  15

Gly Tyr Leu Phe Met Pro Ser Leu Leu Lys Leu Thr Phe Trp Ala
            20                  25                  30

Arg Phe Val Ala Leu Pro Leu Tyr Leu Ala Pro
            35                  40

<210> SEQ ID NO 98
<211> LENGTH: 43
<212> TYPE: PRT
<213> ORGANISM: Siganus artica

<400> SEQUENCE: 98

Asp Leu Ile Glu Met Lys Tyr Lys Gly Glu Lys Leu Pro Glu Ser Tyr
1               5                   10                  15

Arg Lys Glu Arg Asn Ile Ala Ile Gly Leu Arg Val Phe Phe Phe Ile
            20                  25                  30

Arg Lys Phe Val Val Pro Phe Ala Leu His Phe
            35                  40

<210> SEQ ID NO 99
<211> LENGTH: 4
<212> TYPE: PRT
<213> ORGANISM: Ostreococcus tauri
```

```
<400> SEQUENCE: 99

Lys Ala Val Thr
1

<210> SEQ ID NO 100
<211> LENGTH: 4
<212> TYPE: PRT
<213> ORGANISM: Pavlova lutherii

<400> SEQUENCE: 100

Ala Arg Phe Val
1

<210> SEQ ID NO 101
<211> LENGTH: 4
<212> TYPE: PRT
<213> ORGANISM: Pavlova salina

<400> SEQUENCE: 101

Leu Tyr Leu Ala
1

<210> SEQ ID NO 102
<211> LENGTH: 4
<212> TYPE: PRT
<213> ORGANISM: Siganus artica

<400> SEQUENCE: 102

Leu His Phe Ser
1

<210> SEQ ID NO 103
<211> LENGTH: 4
<212> TYPE: PRT
<213> ORGANISM: Thraustochytrium sp.

<400> SEQUENCE: 103

Thr Leu Tyr Leu
1

<210> SEQ ID NO 104
<211> LENGTH: 4
<212> TYPE: PRT
<213> ORGANISM: Pavlova lutherii

<400> SEQUENCE: 104

Arg Trp Glu Gly
1

<210> SEQ ID NO 105
<211> LENGTH: 4
<212> TYPE: PRT
<213> ORGANISM: Pavlova salina

<400> SEQUENCE: 105

Arg Trp Glu Gly
1

<210> SEQ ID NO 106
<211> LENGTH: 4
<212> TYPE: PRT
<213> ORGANISM: Siganus artica

<400> SEQUENCE: 106
```

-continued

```
Lys Tyr Lys Gly
1

<210> SEQ ID NO 107
<211> LENGTH: 4
<212> TYPE: PRT
<213> ORGANISM: Artificial
<220> FEATURE:
<223> OTHER INFORMATION: mutated sequence

<400> SEQUENCE: 107

Lys Tyr Lys Gly
1

<210> SEQ ID NO 108
<211> LENGTH: 4
<212> TYPE: PRT
<213> ORGANISM: Artificial
<220> FEATURE:
<223> OTHER INFORMATION: mutated sequence

<400> SEQUENCE: 108

Arg Trp Tyr Leu
1

<210> SEQ ID NO 109
<211> LENGTH: 4
<212> TYPE: PRT
<213> ORGANISM: Artificial
<220> FEATURE:
<223> OTHER INFORMATION: mutated sequence

<400> SEQUENCE: 109

Arg Trp Glu Leu
1

<210> SEQ ID NO 110
<211> LENGTH: 4
<212> TYPE: PRT
<213> ORGANISM: Artificial
<220> FEATURE:
<223> OTHER INFORMATION: mutated sequence

<400> SEQUENCE: 110

Arg Trp Tyr Gly
1

<210> SEQ ID NO 111
<211> LENGTH: 4
<212> TYPE: PRT
<213> ORGANISM: Artificial
<220> FEATURE:
<223> OTHER INFORMATION: mutated sequence

<400> SEQUENCE: 111

Arg Leu Tyr Gly
1

<210> SEQ ID NO 112
<211> LENGTH: 4
<212> TYPE: PRT
<213> ORGANISM: Artificial
<220> FEATURE:
<223> OTHER INFORMATION: mutated sequence

<400> SEQUENCE: 112

Arg Leu Glu Leu
```

<210> SEQ ID NO 113
<211> LENGTH: 4
<212> TYPE: PRT
<213> ORGANISM: Artificial
<220> FEATURE:
<223> OTHER INFORMATION: mutated sequence

<400> SEQUENCE: 113

Thr Leu Tyr Leu
1

<210> SEQ ID NO 114
<211> LENGTH: 4
<212> TYPE: PRT
<213> ORGANISM: Artificial
<220> FEATURE:
<223> OTHER INFORMATION: mutated sequence

<400> SEQUENCE: 114

Lys Leu Tyr Leu
1

<210> SEQ ID NO 115
<211> LENGTH: 4
<212> TYPE: PRT
<213> ORGANISM: Artificial
<220> FEATURE:
<223> OTHER INFORMATION: mutated sequence

<400> SEQUENCE: 115

Lys Tyr Tyr Leu
1

<210> SEQ ID NO 116
<211> LENGTH: 4
<212> TYPE: PRT
<213> ORGANISM: Artificial
<220> FEATURE:
<223> OTHER INFORMATION: mutated sequence

<400> SEQUENCE: 116

Lys Tyr Lys Leu
1

<210> SEQ ID NO 117
<211> LENGTH: 4
<212> TYPE: PRT
<213> ORGANISM: Artificial
<220> FEATURE:
<223> OTHER INFORMATION: mutated sequence

<400> SEQUENCE: 117

Lys Leu Lys Leu
1

<210> SEQ ID NO 118
<211> LENGTH: 4
<212> TYPE: PRT
<213> ORGANISM: Artificial
<220> FEATURE:
<223> OTHER INFORMATION: mutated sequence

<400> SEQUENCE: 118

Lys Leu Tyr Gly
1

```
<210> SEQ ID NO 119
<211> LENGTH: 4
<212> TYPE: PRT
<213> ORGANISM: Artificial
<220> FEATURE:
<223> OTHER INFORMATION: mutated sequence

<400> SEQUENCE: 119

Lys Leu Lys Gly
1

<210> SEQ ID NO 120
<211> LENGTH: 4
<212> TYPE: PRT
<213> ORGANISM: Artificial
<220> FEATURE:
<223> OTHER INFORMATION: mutated sequence

<400> SEQUENCE: 120

Thr Tyr Tyr Leu
1

<210> SEQ ID NO 121
<211> LENGTH: 4
<212> TYPE: PRT
<213> ORGANISM: Artificial
<220> FEATURE:
<223> OTHER INFORMATION: mutated sequence

<400> SEQUENCE: 121

Thr Tyr Lys Leu
1

<210> SEQ ID NO 122
<211> LENGTH: 4
<212> TYPE: PRT
<213> ORGANISM: Artificial
<220> FEATURE:
<223> OTHER INFORMATION: mutated sequence

<400> SEQUENCE: 122

Thr Tyr Lys Gly
1

<210> SEQ ID NO 123
<211> LENGTH: 4
<212> TYPE: PRT
<213> ORGANISM: Artificial
<220> FEATURE:
<223> OTHER INFORMATION: mutated sequence

<400> SEQUENCE: 123

Thr Leu Lys Leu
1

<210> SEQ ID NO 124
<211> LENGTH: 4
<212> TYPE: PRT
<213> ORGANISM: Artificial
<220> FEATURE:
<223> OTHER INFORMATION: mutated sequence

<400> SEQUENCE: 124

Thr Leu Lys Leu
1
```

```
<210> SEQ ID NO 125
<211> LENGTH: 5
<212> TYPE: PRT
<213> ORGANISM: Thraustochytrium sp.

<400> SEQUENCE: 125

Thr Leu Tyr Leu His
1               5

<210> SEQ ID NO 126
<211> LENGTH: 5
<212> TYPE: PRT
<213> ORGANISM: Pavlova lutherii

<400> SEQUENCE: 126

Arg Trp Glu Gly Glu
1               5

<210> SEQ ID NO 127
<211> LENGTH: 5
<212> TYPE: PRT
<213> ORGANISM: Pavlova salina

<400> SEQUENCE: 127

Arg Trp Glu Gly Glu
1               5

<210> SEQ ID NO 128
<211> LENGTH: 5
<212> TYPE: PRT
<213> ORGANISM: Thraustochytrium sp.

<400> SEQUENCE: 128

Arg Trp Glu Gly Glu
1               5

<210> SEQ ID NO 129
<211> LENGTH: 43
<212> TYPE: PRT
<213> ORGANISM: Thraustochytrium sp.

<400> SEQUENCE: 129

Ile Gly Leu Gly Trp Thr Leu Tyr Leu His Pro Arg Tyr Met Leu Arg
1               5                   10                  15

Thr Lys Arg His Met Glu Phe Val Trp Ile Phe Ala Arg Tyr Ile Gly
            20                  25                  30

Trp Phe Ser Leu Met Gly Ala Leu Gly Tyr Ser
        35                  40

<210> SEQ ID NO 130
<211> LENGTH: 43
<212> TYPE: PRT
<213> ORGANISM: Pavlova lutherii

<400> SEQUENCE: 130

Glu Leu Leu Ala Trp Arg Trp Glu Gly Glu Lys Ile Ser Pro Leu Ala
1               5                   10                  15

Arg Ala Leu Phe Ala Pro Ala Val Ala Cys Lys Leu Gly Phe Trp Ala
            20                  25                  30

Arg Phe Val Ala Leu Pro Leu Trp Leu Gln Pro
        35                  40
```

<210> SEQ ID NO 131
<211> LENGTH: 21
<212> TYPE: PRT
<213> ORGANISM: Thraustochytrium sp.

<400> SEQUENCE: 131

Phe Val Trp Ile Phe Ala Arg Tyr Ile Gly Trp Phe Ser Leu Met Gly
1               5                   10                  15

Ala Leu Gly Tyr Ser
            20

<210> SEQ ID NO 132
<211> LENGTH: 21
<212> TYPE: PRT
<213> ORGANISM: Pavlova lutherii

<400> SEQUENCE: 132

Ala Val Ala Cys Lys Leu Gly Phe Trp Ala Arg Phe Val Ala Leu Pro
1               5                   10                  15

Leu Trp Leu Gln Pro
            20

<210> SEQ ID NO 133
<211> LENGTH: 21
<212> TYPE: PRT
<213> ORGANISM: Pavlova salina

<400> SEQUENCE: 133

Ser Leu Leu Leu Lys Leu Thr Phe Trp Ala Arg Phe Val Ala Leu Pro
1               5                   10                  15

Leu Tyr Leu Ala Pro
            20

<210> SEQ ID NO 134
<211> LENGTH: 21
<212> TYPE: PRT
<213> ORGANISM: Saginus artica

<400> SEQUENCE: 134

Ala Ile Gly Leu Arg Val Phe Phe Phe Ile Arg Lys Phe Val Val Pro
1               5                   10                  15

Phe Ala Leu His Phe
            20

<210> SEQ ID NO 135
<211> LENGTH: 21
<212> TYPE: PRT
<213> ORGANISM: Pavlova lutherii

<400> SEQUENCE: 135

Arg Ala Leu Phe Ala Pro Ala Val Ala Cys Lys Leu Gly Phe Trp Ala
1               5                   10                  15

Arg Phe Val Ala Leu
            20

<210> SEQ ID NO 136
<211> LENGTH: 21
<212> TYPE: PRT
<213> ORGANISM: Pavlova salina

<400> SEQUENCE: 136

Leu Leu Leu Lys Leu Thr Phe Trp Ala Arg Phe Val Ala Leu Pro Leu
1               5                   10                  15

Tyr Leu Ala Pro Ser
            20

<210> SEQ ID NO 137
<211> LENGTH: 21
<212> TYPE: PRT
<213> ORGANISM: Saginus arctica

<400> SEQUENCE: 137

Leu Arg Val Phe Phe Phe Ile Arg Lys Phe Val Val Pro Phe Ala Leu
1               5                   10                  15

His Phe Ser Trp Tyr
            20

<210> SEQ ID NO 138
<211> LENGTH: 4
<212> TYPE: PRT
<213> ORGANISM: Thraustochytrium sp.

<400> SEQUENCE: 138

Gly Ala Leu Gly
1

<210> SEQ ID NO 139
<211> LENGTH: 4
<212> TYPE: PRT
<213> ORGANISM: Pavlova lutherii

<400> SEQUENCE: 139

Pro Leu Trp Leu
1

<210> SEQ ID NO 140
<211> LENGTH: 4
<212> TYPE: PRT
<213> ORGANISM: Pavlova salina

<400> SEQUENCE: 140

Pro Leu Tyr Leu
1

<210> SEQ ID NO 141
<211> LENGTH: 4
<212> TYPE: PRT
<213> ORGANISM: Saginus artica

<400> SEQUENCE: 141

Pro Phe Ala Leu
1

<210> SEQ ID NO 142
<211> LENGTH: 4
<212> TYPE: PRT
<213> ORGANISM: Pavlova lutherii

<400> SEQUENCE: 142

Ala Arg Phe Val
1

<210> SEQ ID NO 143
<211> LENGTH: 4
<212> TYPE: PRT
<213> ORGANISM: Pavlova salina

```
<400> SEQUENCE: 143

Leu Tyr Leu Ala
1

<210> SEQ ID NO 144
<211> LENGTH: 4
<212> TYPE: PRT
<213> ORGANISM: Saginus artica

<400> SEQUENCE: 144

Leu His Phe Ser
1

<210> SEQ ID NO 145
<211> LENGTH: 3
<212> TYPE: PRT
<213> ORGANISM: P. irregulare

<400> SEQUENCE: 145

Ala Gln Ser
1

<210> SEQ ID NO 146
<211> LENGTH: 4
<212> TYPE: PRT
<213> ORGANISM: Pavlova salina

<400> SEQUENCE: 146

Phe Leu Asp Ile
1

<210> SEQ ID NO 147
<211> LENGTH: 4
<212> TYPE: PRT
<213> ORGANISM: Pavlova lutherii

<400> SEQUENCE: 147

Phe Leu Asp Ala
1

<210> SEQ ID NO 148
<211> LENGTH: 4
<212> TYPE: PRT
<213> ORGANISM: Saginus artica

<400> SEQUENCE: 148

Phe Leu Gly Leu
1

<210> SEQ ID NO 149
<211> LENGTH: 4
<212> TYPE: PRT
<213> ORGANISM: M. brevicollis

<400> SEQUENCE: 149

Ile Gly Asp Trp
1

<210> SEQ ID NO 150
<211> LENGTH: 4
<212> TYPE: PRT
<213> ORGANISM: E. huxleyi

<400> SEQUENCE: 150
```

-continued

```
Phe Thr Ile Arg
1

<210> SEQ ID NO 151
<211> LENGTH: 4
<212> TYPE: PRT
<213> ORGANISM: T. pseudonana

<400> SEQUENCE: 151

Phe Gln Gln Asp
1

<210> SEQ ID NO 152
<211> LENGTH: 4
<212> TYPE: PRT
<213> ORGANISM: Thraustochytrium sp.

<400> SEQUENCE: 152

Val Thr Gln Asp
1

<210> SEQ ID NO 153
<211> LENGTH: 21
<212> TYPE: PRT
<213> ORGANISM: P. irregulare

<400> SEQUENCE: 153

Ala Gly Leu Ile Val His Tyr Ile Trp Gln Leu Ala Ile Pro Tyr Phe
1               5                   10                  15

Cys Asn Met Ser Leu
            20

<210> SEQ ID NO 154
<211> LENGTH: 21
<212> TYPE: PRT
<213> ORGANISM: Pavlova lutherii

<400> SEQUENCE: 154

Val Ala Cys Lys Leu Gly Phe Trp Ala Arg Phe Val Ala Leu Pro Leu
1               5                   10                  15

Trp Leu Gln Pro Thr
            20

<210> SEQ ID NO 155
<211> LENGTH: 21
<212> TYPE: PRT
<213> ORGANISM: Pavlova salina

<400> SEQUENCE: 155

Leu Leu Leu Lys Leu Thr Phe Trp Ala Arg Phe Val Ala Leu Pro Leu
1               5                   10                  15

Tyr Leu Ala Pro Ser
            20

<210> SEQ ID NO 156
<211> LENGTH: 21
<212> TYPE: PRT
<213> ORGANISM: S. artica

<400> SEQUENCE: 156

Ile Gly Leu Arg Val Phe Phe Phe Ile Arg Lys Phe Val Val Pro Phe
1               5                   10                  15

Ala Leu His Phe Ser
```

-continued

```
<210> SEQ ID NO 157
<211> LENGTH: 21
<212> TYPE: PRT
<213> ORGANISM: Thraustochytrium sp.

<400> SEQUENCE: 157

Trp Ile Met Lys Ala Leu Thr Val Leu Tyr Met Val Ala Leu Pro Cys
1               5                   10                  15

Tyr Met Gln Gly Pro
            20

<210> SEQ ID NO 158
<211> LENGTH: 21
<212> TYPE: PRT
<213> ORGANISM: M. brevicollis

<400> SEQUENCE: 158

Val Leu Ala Arg Ile Cys Trp Leu Val Arg Leu Val Ala Ile Pro Val
1               5                   10                  15

Tyr Leu His Gly Trp
            20

<210> SEQ ID NO 159
<211> LENGTH: 21
<212> TYPE: PRT
<213> ORGANISM: Pavlova lutherii

<400> SEQUENCE: 159

Arg Ala Leu Phe Ala Pro Ala Val Ala Cys Lys Leu Gly Phe Trp Ala
1               5                   10                  15

Arg Phe Val Ala Leu
            20

<210> SEQ ID NO 160
<211> LENGTH: 21
<212> TYPE: PRT
<213> ORGANISM: Pavlova salina

<400> SEQUENCE: 160

Leu Leu Leu Lys Leu Thr Phe Trp Ala Arg Phe Val Ala Leu Pro Leu
1               5                   10                  15

Tyr Leu Ala Pro Ser
            20

<210> SEQ ID NO 161
<211> LENGTH: 21
<212> TYPE: PRT
<213> ORGANISM: S.arctica

<400> SEQUENCE: 161

Leu Arg Val Phe Phe Phe Ile Arg Lys Phe Val Val Pro Phe Ala Leu
1               5                   10                  15

His Phe Ser Trp Tyr
            20

<210> SEQ ID NO 162
<211> LENGTH: 4
<212> TYPE: PRT
<213> ORGANISM: P. irregulare

<400> SEQUENCE: 162
```

```
Phe Cys Asn Met
1

<210> SEQ ID NO 163
<211> LENGTH: 4
<212> TYPE: PRT
<213> ORGANISM: Pavlova lutherii

<400> SEQUENCE: 163

Leu Trp Leu Gln
1

<210> SEQ ID NO 164
<211> LENGTH: 4
<212> TYPE: PRT
<213> ORGANISM: Pavlova salina

<400> SEQUENCE: 164

Leu Tyr Leu Ala
1

<210> SEQ ID NO 165
<211> LENGTH: 4
<212> TYPE: PRT
<213> ORGANISM: Siganus artica

<400> SEQUENCE: 165

Phe Ala Leu His
1

<210> SEQ ID NO 166
<211> LENGTH: 4
<212> TYPE: PRT
<213> ORGANISM: Thraustochytrium sp.

<400> SEQUENCE: 166

Cys Tyr Met Gln
1

<210> SEQ ID NO 167
<211> LENGTH: 4
<212> TYPE: PRT
<213> ORGANISM: Pavlova lutherii

<400> SEQUENCE: 167

Ala Arg Phe Val
1

<210> SEQ ID NO 168
<211> LENGTH: 4
<212> TYPE: PRT
<213> ORGANISM: Pavlova salina

<400> SEQUENCE: 168

Leu Tyr Leu Ala
1

<210> SEQ ID NO 169
<211> LENGTH: 4
<212> TYPE: PRT
<213> ORGANISM: Siganus artica

<400> SEQUENCE: 169

Leu His Phe Ser
```

<210> SEQ ID NO 170
<211> LENGTH: 4
<212> TYPE: PRT
<213> ORGANISM: Thraustochytrium sp.

<400> SEQUENCE: 170

Ala Leu Pro Cys
1

<210> SEQ ID NO 171
<211> LENGTH: 1872
<212> TYPE: DNA
<213> ORGANISM: Siganus canaliculatus

<400> SEQUENCE: 171

```
gaaactattt gaggaggatg gggatgtgag taggtgaact cgaatgtgga cggagcacgg      60
tcaacgtgac cacaggaaag cagacaacgt ttgcaaataa gtggatctaa agcagagaca     120
gcagtgaaga tgggaggtgg aggtcagccg agggagtcag gggagcccgg cagcagtcca     180
gctgtgtaca cctgggagga ggtgcagcac cactcttcca ggaatgacca gtggttggtg     240
atcgatcgaa aagtttataa catctctcag tgggccaaac ggcacccagg agggtaccgg     300
gtgattggcc attatgctgg ggaggatgct acggaagcat tcactgcttt ccaccctgac     360
ttgaaatttg tgcaaaagtt cctcaagcct tgctgatag gagagctggc agccacagag     420
cccagccagg accgaaacaa aaatgccgca ctcatacagg atttccacac tttacgtcag     480
caagcggaga gtgagggtct gtttcaagct cgccctttgt tcttcctcct tcatttgggt     540
cacatcctgt tgctggaggc tctggcccct ctgatggtct ggcactgggg aacgggctgg     600
ctacagacgt tactatgtgc cgttatgctg gcaactgctc agtctcaggc cggctggctt     660
cagcacgact ttggacacct gtctgtcttc aagaaatccc gctggaatca cttggttcac     720
cactttgtca tcggccattt aaagggagct tctgccaact ggtggaatca tcgtcatttc     780
cagcatcacg ctaaacccaa catcttcaag aaggatcctg acatcaacat ggtggacctt     840
tttgtacttg gagagactca acctgtggag tatggcgtaa agaagatcaa attaatgccc     900
tacaaccacc agcaccagta cttccatctc attggaccac gcttctcat tccagttttt     960
ttccactacc agttgctgaa aatcatgatt tctcaccgct actggctgga tctggtgtgg    1020
tgcttgtcct tctaccttcg gtacatgtgc tgctatgtgc cggtctacgg ccttttttgga   1080
tctgtggtac tcattgtatt tacaaggttt ttggagagcc actggttcgt gtgggtgacg    1140
cagatgaatc atctgccgat ggacatcaac tatgagaacc acaacgactg gctgtccatg    1200
cagttgcaag ccacctgtaa tgttgagcag tctctcttca acgactggtt cagtggacat    1260
ctcaactttc aaatcgaaca ccatttgttt cccaccatgc cgcgccacaa ctaccacctg    1320
gtggttccac gggtccgtgc actctgtgag aaacatgaga taccatacca ggtgaagaca    1380
ctgccgcagg ccttcgctga tatcatcagg tcactgaaaa actcagggga gctctggctt    1440
gatgcatatc tccataaatg aactctataa tttagtcttg atgctgcatg taacaggaat    1500
gattgtttct cctctatgct gatttatgaa ttgtttgtat caatttttaa tcccactgaa    1560
tttgtgaaaa tgatcttttc taattattgg ttttatgcac ccttgttttt actgtgcgtc    1620
ctggacagga ttttttagcac tcactggaac ctgcccacat ggttttatag gaccttaagc    1680
aatagtggtg ttttgataca aatacagcag ctgtaaatga tgtgtcatga gttttttgtct  1740
```

-continued

```
ttatcttgtg atacagtttg cactgtctga gaatgaattg ttttttttcc gacagacttc    1800
tttgctggct actcttctga tctctccatg cctattaaat tttgtggatt aaaaaaaaaa    1860
aaaaaaaaaa aa                                                       1872
```

<210> SEQ ID NO 172
<211> LENGTH: 443
<212> TYPE: PRT
<213> ORGANISM: Siganus canaliculatus

<400> SEQUENCE: 172

```
Met Gly Gly Gly Gln Pro Arg Glu Ser Gly Glu Pro Gly Ser Ser
1               5                   10                  15

Pro Ala Val Tyr Thr Trp Glu Glu Val Gln His His Ser Ser Arg Asn
            20                  25                  30

Asp Gln Trp Leu Val Ile Asp Arg Lys Val Tyr Asn Ile Ser Gln Trp
        35                  40                  45

Ala Lys Arg His Pro Gly Gly Tyr Arg Val Ile Gly His Tyr Ala Gly
    50                  55                  60

Glu Asp Ala Thr Glu Ala Phe Thr Ala Phe His Pro Asp Leu Lys Phe
65                  70                  75                  80

Val Gln Lys Phe Leu Lys Pro Leu Leu Ile Gly Glu Leu Ala Ala Thr
                85                  90                  95

Glu Pro Ser Gln Asp Arg Asn Lys Asn Ala Ala Leu Ile Gln Asp Phe
            100                 105                 110

His Thr Leu Arg Gln Gln Ala Glu Ser Glu Gly Leu Phe Gln Ala Arg
        115                 120                 125

Pro Leu Phe Phe Leu Leu His Leu Gly His Ile Leu Leu Leu Glu Ala
    130                 135                 140

Leu Ala Leu Leu Met Val Trp His Trp Gly Thr Gly Trp Leu Gln Thr
145                 150                 155                 160

Leu Leu Cys Ala Val Met Leu Ala Thr Ala Gln Ser Gln Ala Gly Trp
                165                 170                 175

Leu Gln His Asp Phe Gly His Leu Ser Val Phe Lys Lys Ser Arg Trp
            180                 185                 190

Asn His Leu Val His His Phe Val Ile Gly His Leu Lys Gly Ala Ser
        195                 200                 205

Ala Asn Trp Trp Asn His Arg His Phe Gln His Ala Lys Pro Asn
    210                 215                 220

Ile Phe Lys Lys Asp Pro Asp Ile Asn Met Val Asp Leu Phe Val Leu
225                 230                 235                 240

Gly Glu Thr Gln Pro Val Glu Tyr Gly Val Lys Lys Ile Lys Leu Met
                245                 250                 255

Pro Tyr Asn His Gln His Gln Tyr Phe His Leu Ile Gly Pro Pro Leu
            260                 265                 270

Leu Ile Pro Val Phe Phe His Tyr Gln Leu Leu Lys Ile Met Ile Ser
        275                 280                 285

His Arg Tyr Trp Leu Asp Leu Val Trp Cys Leu Ser Phe Tyr Leu Arg
    290                 295                 300

Tyr Met Cys Cys Tyr Val Pro Val Tyr Gly Leu Phe Gly Ser Val Val
305                 310                 315                 320

Leu Ile Val Phe Thr Arg Phe Leu Glu Ser His Trp Phe Val Trp Val
                325                 330                 335

Thr Gln Met Asn His Leu Pro Met Asp Ile Asn Tyr Glu Asn His Asn
            340                 345                 350
```

```
Asp Trp Leu Ser Met Gln Leu Gln Ala Thr Cys Asn Val Glu Gln Ser
        355                 360                 365
Leu Phe Asn Asp Trp Phe Ser Gly His Leu Asn Phe Gln Ile Glu His
    370                 375                 380
His Leu Phe Pro Thr Met Pro Arg His Asn Tyr His Leu Val Val Pro
385                 390                 395                 400
Arg Val Arg Ala Leu Cys Glu Lys His Glu Ile Pro Tyr Gln Val Lys
                405                 410                 415
Thr Leu Pro Gln Ala Phe Ala Asp Ile Ile Arg Ser Leu Lys Asn Ser
            420                 425                 430
Gly Glu Leu Trp Leu Asp Ala Tyr Leu His Lys
        435                 440

<210> SEQ ID NO 173
<211> LENGTH: 1854
<212> TYPE: DNA
<213> ORGANISM: Siganus canaliculatus

<400> SEQUENCE: 173
gagaagacgg aggatgagga tgttgactgt ttaaactgga tgtgaaagga gatccgttaa     60
tgtgactgca aacccgaggg gatctgaagc cggaaatctg gattttgtgg atctcgagca    120
gagacagcag tgaggatggg aggtggaggt cagctggggg agtcagggga gaatggctgc    180
aagtcagctg ctggtgtgta cacttgggag gaggtgcagc accacagcaa caggaatgac    240
cagtggttgg tcattgatcg caaggtttat aatgtcaccc agtgggccaa gagacaccca    300
ggagggtttc gggtcctcaa ccactatgct ggagaggatg ctacggaggc attcactgct    360
tttcaccccg acataaaatt tgtacaaaag tatatgaagc ctttgctggt aggagagctg    420
gctgcaacgg agcccagtca ggatcaagac aaaaatgccg cactcataca ggatttccac    480
actttacgtc agcaagcgga gagtgagggt ctgtttcaag ctcgcccttt gttcttcctc    540
cttcatttgg gtcacatcct gttgctggag gctctggccc ttctgatggt ctggcactgg    600
ggaacgggct ggctacagac gttactatgt gccgttatgc tggcaactgc tcagtctcag    660
gccggctggc ttcagcacga cttttggaca ctgtctgtct tcaagaaatc ccgctggaat    720
cacttggttc acaagtttgt catcggccat ttaaagggag cttctgccaa ctggtggaat    780
catcgtcatt ccagcatca cgctaaaccc aacatcttca agaaggatcc tgacatcaac    840
atggtggacc tttttgtact tggagagact caacctgtgg agtatggcat aaagaagatt    900
aaaaatatgc cctataacca ccagcacaag tatttctttt tggttgcgcc accacttctt    960
attccagttt tctacaacta taacataatg atgaccatga ttactcgccg tgactatgtg   1020
gatctgtctt gggccatgac gttttacatt cgctacatgt tgtgctatgt gccggtctat   1080 ggccttttg gatcactggc gctcatgatg tttgccaggt ttttggagag ccactggttc   1140
gtgtgggtaa ctcagatgag tcatctgccc atggacatcg acaatgacaa acgccgtgac   1200
tggctgtcca tgcagttaca agccaccctgt aacattgaga gtctttttt caacgactgg   1260 ttcagtggac acctcaactt ccaaattgaa caccatttgt tcccgaggat gccgcgccac   1320
aactaccacc tggtggctcc acaggtccag acactgtgtg agaaacatgg gattccatac   1380
gaagtgaaaa cgctgtggaa aggcatggtt gacgtcgtca gggcactgaa aaaatcagga   1440
gacctctggc ttgatgcata tctccataaa tgacctgttt tggcctcaga gctgcaccta   1500
acaggagtca cgtttagtct cctcttcact tgtatcagta caatttagaa ttaagttgat   1560
```

```
tgcgtaggtt cggtcttttc taattgcctg tgtagagttc agtgtttttg catcttgtat    1620
aagacgtttg tgcctacttt gccttacagt atccttaacc atagtgatac tattaataaa    1680
taatccagtt aaaatgtttt tcattgtcat gtgatagcat aacataattt cacaaataaa    1740
gaatgtttat ttgttacgta ctcaatcctg tgctgagcat tttcactttg aacttctgtt    1800
ccagacaata caataaaaac atgaagagta caaaaaaaaa aaaaaaaaaa aaaa           1854
```

<210> SEQ ID NO 174
<211> LENGTH: 445
<212> TYPE: PRT
<213> ORGANISM: Siganus canaliculatus

<400> SEQUENCE: 174

```
Met Gly Gly Gly Gly Gln Leu Gly Glu Ser Gly Glu Asn Gly Cys Lys
1               5                   10                  15

Ser Ala Ala Gly Val Tyr Thr Trp Glu Glu Val Gln His His Ser Asn
            20                  25                  30

Arg Asn Asp Gln Trp Leu Val Ile Asp Arg Lys Val Tyr Asn Val Thr
        35                  40                  45

Gln Trp Ala Lys Arg His Pro Gly Gly Phe Arg Val Leu Asn His Tyr
    50                  55                  60

Ala Gly Glu Asp Ala Thr Glu Ala Phe Thr Ala Phe His Pro Asp Ile
65                  70                  75                  80

Lys Phe Val Gln Lys Tyr Met Lys Pro Leu Leu Val Gly Glu Leu Ala
                85                  90                  95

Ala Thr Glu Pro Ser Gln Asp Gln Asp Lys Asn Ala Ala Leu Ile Gln
            100                 105                 110

Asp Phe His Thr Leu Arg Gln Gln Ala Glu Ser Glu Gly Leu Phe Gln
        115                 120                 125

Ala Arg Pro Leu Phe Phe Leu Leu His Leu Gly His Ile Leu Leu Leu
    130                 135                 140

Glu Ala Leu Ala Leu Leu Met Val Trp His Trp Gly Thr Gly Trp Leu
145                 150                 155                 160

Gln Thr Leu Leu Cys Ala Val Met Leu Ala Thr Ala Gln Ser Gln Ala
                165                 170                 175

Gly Trp Leu Gln His Asp Phe Gly His Leu Ser Val Phe Lys Lys Ser
            180                 185                 190

Arg Trp Asn His Leu Val His Lys Phe Val Ile Gly His Leu Lys Gly
        195                 200                 205

Ala Ser Ala Asn Trp Trp Asn His Arg His Phe Gln His His Ala Lys
    210                 215                 220

Pro Asn Ile Phe Lys Lys Asp Pro Asp Ile Asn Met Val Asp Leu Phe
225                 230                 235                 240

Val Leu Gly Glu Thr Gln Pro Val Glu Tyr Gly Ile Lys Lys Ile Lys
                245                 250                 255

Asn Met Pro Tyr Asn His Gln His Lys Tyr Phe Phe Leu Val Ala Pro
            260                 265                 270

Pro Leu Leu Ile Pro Val Phe Tyr Asn Tyr Asn Ile Met Met Thr Met
        275                 280                 285

Ile Thr Arg Arg Asp Tyr Val Asp Leu Ser Trp Ala Met Thr Phe Tyr
    290                 295                 300

Ile Arg Tyr Met Leu Cys Tyr Val Pro Val Tyr Gly Leu Phe Gly Ser
305                 310                 315                 320

Leu Ala Leu Met Met Phe Ala Arg Phe Leu Glu Ser His Trp Phe Val
```

-continued

```
                    325                 330                 335
Trp Val Thr Gln Met Ser His Leu Pro Met Asp Ile Asp Asn Asp Lys
            340                 345                 350

Arg Arg Asp Trp Leu Ser Met Gln Leu Gln Ala Thr Cys Asn Ile Glu
            355                 360                 365

Lys Ser Phe Phe Asn Asp Trp Phe Ser Gly His Leu Asn Phe Gln Ile
            370                 375                 380

Glu His His Leu Phe Pro Arg Met Pro Arg His Asn Tyr His Leu Val
385                 390                 395                 400

Ala Pro Gln Val Gln Thr Leu Cys Glu Lys His Gly Ile Pro Tyr Glu
            405                 410                 415

Val Lys Thr Leu Trp Lys Gly Met Val Asp Val Val Arg Ala Leu Lys
            420                 425                 430

Lys Ser Gly Asp Leu Trp Leu Asp Ala Tyr Leu His Lys
            435                 440                 445
```